(12) United States Patent
Samson et al.

(10) Patent No.: US 9,938,587 B2
(45) Date of Patent: Apr. 10, 2018

(54) METHODS AND KITS FOR DETERMINING DNA REPAIR CAPACITY

(71) Applicant: Massachusetts Institute of Technology, Cambridge, MA (US)

(72) Inventors: Leona D. Samson, Newton, MA (US); Zachary David Nagel, Cambridge, MA (US); Carrie Thompson, Cambridge, MA (US); Isaac Alexander Chaim, Boston, MA (US); Anwaar Ahmad, North Easton, MA (US); Anthony L. Forget, Charlton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/346,183

(22) PCT Filed: Sep. 20, 2012

(86) PCT No.: PCT/US2012/056433
§ 371 (c)(1),
(2) Date: Mar. 20, 2014

(87) PCT Pub. No.: WO2013/043936
PCT Pub. Date: Mar. 28, 2013

(65) Prior Publication Data
US 2014/0227701 A1    Aug. 14, 2014

Related U.S. Application Data

(60) Provisional application No. 61/536,659, filed on Sep. 20, 2011.

(51) Int. Cl.
| | |
|---|---|
| C12Q 1/68 | (2006.01) |
| C12N 15/10 | (2006.01) |
| C12N 15/09 | (2006.01) |
| C12N 15/64 | (2006.01) |
| C12N 15/85 | (2006.01) |

(52) U.S. Cl.
CPC ....... *C12Q 1/6897* (2013.01); *C12N 15/1086* (2013.01); *C12Q 1/6886* (2013.01)

(58) Field of Classification Search
None
See application file for complete search history.

(56) References Cited

U.S. PATENT DOCUMENTS

| | | | |
|---|---|---|---|
| 4,975,365 A | 12/1990 | Grossman et al. | |
| 2001/0031739 A1 | 10/2001 | Dare | |
| 2003/0003454 A1 | 1/2003 | Livneh et al. | |
| 2006/0160108 A1* | 7/2006 | Romanov et al. | 435/6 |
| 2009/0272657 A1 | 11/2009 | Bhatia et al. | |
| 2010/0285456 A1 | 11/2010 | Matta | |

FOREIGN PATENT DOCUMENTS

EP    2123770 A1    11/2009

OTHER PUBLICATIONS

Baesecke et al., "A Host Cell Reactivation Assay for DNA Repair System Analysis in Primary Hematopoietic Cells" 104 Blood Abstract 4475 (2004).*
Pietras et al., "Monoclonal Antibody to HER-2/neuReceptor Modulates Repair of Radiation-induced DNA Damage and Enhances Radiosensitivity of Human Breast Cancer Cells Overexpressing This Oncogene" 59 Cancer Research 1347-1355 (1999).*
Igoucheva et al., "Differential cellular responses to exogenous DNA in mammalian cells and its effect on oligonucleotide-directed gene modification" 13 Gene Therapy 266-275 (2006).*
Rastogi et al., "Molecular Mechanisms of Ultraviolet Radiation-Induced DNA Damage and Repair" 2010 Journal of Nucleic Acids Art . 592980 1-32 (2010).*
Fu et al., "Balancing repair and tolerance of DNA damage caused by alkylating agents" 12 Nature Reviews | Cancer 104-120 (2012).*
[No Author Listed], Glyco-SPOT DNA repair assay kit. Bertin pharma. Jun. 2013.
Ang et al., Preparation of mammalian expression vectors incorporating site-specifically platinated-DNA lesions. Bioconjug Chem. May 20, 2009;20(5):1058-63. doi: 10.1021/bc900031a.
Athas et al., Development and field-test validation of an assay for DNA repair in circulating human lymphocytes. Cancer Res. Nov. 1, 1991;51(21):5786-93.
Bolt, Gansewendt B. Mechanisms of carcinogenicity of methyl halides. Crit Rev Toxicol. 1993;23(3):237-53.
Brégeon et al., Assays for transcriptional mutagenesis in active genes. Methods Enzymol. 2006;409:345-57.
Brégeon et al., Transcriptional mutagenesis: causes and involvement in tumour development. Nat Rev Cancer. Mar. 2011;11(3):218-27. doi: 10.1038/nrc3006.
Burger et al., A modified fluorimetric host cell reactivation assay to determine the repair capacity of primary keratinocytes, melanocytes and fibroblasts. BMC Biotechnol. Jun. 22, 2010;10:46. doi: 10.1186/1472-6750-10-46.
Caramori et al., Unbalanced oxidant-induced DNA damage and repair in COPD: a link towards lung cancer. Thorax. Jun. 2011;66(6):521-7. doi: 10.1136/thx.2010.156448. Epub Apr. 2, 2011.
Chin et al., Translating insights from the cancer genome into clinical practice. Nature. Apr. 3, 2008;452(7187):553-63. doi: 10.1038/nature06914.
Choy et al., Genetic analysis of human traits in vitro: drug response and gene expression in lymphoblastoid cell lines. PloS Genet. Nov. 2008;4(11):e1000287. doi: 10.1371/journal.pgen.1000287. Epub Nov. 28, 2008.
Cole, Psoralen monoadducts and interstrand cross-links in DNA. Biochim Biophys Acta. Nov. 29, 1971;254(1):30-9.

(Continued)

*Primary Examiner* — Nancy J Leith
(74) *Attorney, Agent, or Firm* — Wolf, Greenfield & Sacks, P.C.

(57) ABSTRACT

In one aspect, the disclosure provides methods, compositions, vectors and kits for determining DNA repair capacity in cells or a subject.

30 Claims, 49 Drawing Sheets

(56) References Cited

OTHER PUBLICATIONS

Cooke et al., Oxidative DNA damage: mechanisms, mutation, and disease. FASEB J. Jul. 2003;17(10):1195-214.
Davis et al., Expression differences by continent of origin point to the immortalization process. Hum Mol Genet. Oct. 15, 2009;18(20):3864-75. doi: 10.1093/hmg/ddp330. Epub Jul. 23, 2009.
Decordier et al., Phenotyping for DNA repair capacity. Mutat Res. Oct. 2010;705(2):107-29. doi: 10.1016/j.mrrev.2010.05.002. Epub May 15, 2010.
Dimitri et al., Transcription elongation past O6-methylguanine by human RNA polymerase II and bacteriophage T7 RNA polymerase. Nucleic Acids Res. Nov. 2008;36(20):6459-71. doi: 10.1093/nar/gkn657. Epub Oct. 14, 2008.
Essigmann et al., Structural identification of the major DNA adduct formed by aflatoxin B1 in vitro. Proc Natl Acad Sci U S A. May 1977;74(5):1870-4.
Fry et al., Genomic predictors of interindividual differences in response to DNA damaging agents. Genes Dev. Oct. 1, 2008;22(19):2621-6. doi: 10.1101/gad.1688508. Epub Sep. 19, 2008.
Hofseth et al., The adaptive imbalance in base excision-repair enzymes generates microsatellite instability in chronic inflammation. J Clin Invest. Dec. 2003;112(12):1887-94. Erratum in: J Clin.Invest. Feb. 2004;113(3):490.
Huefner et al., Breadth by depth: expanding our understanding of the repair of transposon-induced DNA double strand breaks via deep-sequencing. DNA Repair (Amst). Oct. 10, 2011;10(10):1023-33. doi:10.1016/j.dnarep.2011.07.011. Epub Sep. 1, 2011.
Iliakis, The role of DNA double strand breaks in ionizing radiation-induced killing of eukaryotic cells. Bioessays. Dec. 1991;13(12):641-8.
Johnson et al., Analysis of DNA repair using transfection-based host cell reactivation. Methods Mol Biol. 2005;291:321-35.
Kamileri et al., Nucleotide excision repair: new tricks with old bricks. Trends Genet. Nov. 2012;28(11):566-73. doi: 10.1016/j.tig.2012.06.004. Epub Jul. 22, 2012.
Kim et al., Overview of base excision repair biochemistry. Curr Mol Pharmacol. Jan. 2012;5(1):3-13.
Kitsera et al., 8-Oxo-7,8-dihydroguanine in DNA does not constitute a barrier to transcription, but is converted into transcription-blocking damage by OGG1. Nucleic Acids Res. Aug. 2011;39(14):5926-34. doi: 10.1093/nar/gkr163. Epub Mar. 25, 2011.
Kiziltepe et al., Delineation of the chemical pathways underlying nitric oxide-induced homologous recombination in mammalian cells. Chem Biol. Mar. 2005;12(3):357-69.
Koboldt et al., VarScan 2: somatic mutation and copy number alteration discovery in cancer by exome sequencing. Genome Res. Mar. 2012;22(3):568-76. doi: 10.1101/gr.129684.111. Epub Feb. 2, 2012.
Kraemer et al., DNA repair protects against cutaneous and internal neoplasia: evidence from xeroderma pigmentosum. Carcinogenesis. Apr. 1984;5(4):511-4.
Marietta et al., Transcriptional bypass of bulky DNA lesions causes new mutant RNA transcripts in human cells. EMBO Rep. Apr. 2007;8(4):388-93. Epub Mar. 16, 2007.
Marnett, Oxyradicals and DNA damage. Carcinogenesis. Mar. 2000;21(3):361-70.
Mendez et al., A modified host-cell reactivation assay to quantify DNA repair capacity in cryopreserved peripheral lymphocytes. DNA Repair (Amst). Jun. 10, 2011;10(6):603-10. doi: 10.1016/j.dnarep.2011.04.001. Epub May 5, 2011.
Nagel et al., High-throughput assay to assess the global DNA repair capacity of human cells. Poster. 2012.
Perlow et al., DNA adducts from a tumorigenic metabolite of benzo[a]pyrene block human RNA polymerase II elongation in a sequence- and stereochemistry-dependent manner. J Mol Biol. Aug. 2, 2002;321(1):29-47.
Posnick et al., Imbalanced base excision repair increases spontaneous mutation and alkylation sensitivity in *Escherichia coli*. J Bacteriol. Nov. 1999;181(21):6763-71.
Qiao et al., Rapid assessment of repair of ultraviolet DNA damage with a modified host-cell reactivation assay using a luciferase reporter gene and correlation with polymorphisms of DNA repair genes in normal human lymphocytes. Mutat Res. Nov. 30, 2002;509(1-2):165-74.
Ralhan et al., Links between DNA double strand break repair and breast cancer: accumulating evidence from both familial and nonfamilial cases. Cancer Lett. Apr. 8, 2007;248(1):1-17. Epub Jul. 18, 2006.
Ramos et al., DNA repair and breast carcinoma susceptibility in women. Cancer. Apr. 1, 2004;100(7):1352-7.
Satokata et al., Identification of splicing mutations of the last nucleotides of exons, a nonsense mutation, and a missense mutation of the XPAC gene as causes of group a xeroderma pigmentosum. Mutat Res. Mar. 1992;273(2):203-12.
Schut et al., DNA adducts of heterocyclic amine food mutagens: implications for mutagenesis and carcinogenesis. Carcinogenesis. Mar. 1999;20(3):353-68.
Setlow et al., Pyrimidine dimers in ultraviolet-irradiated DNA's. J Mol Biol. May 1966;17(1):237-54.
Shrivastav et al., Chemical biology of mutagenesis and DNA repair: cellular responses to DNA alkylation. Carcinogenesis. Jan. 2010;31(1):59-70. doi: 10.1093/carcin/bgp262. Epub Oct. 29, 2009.
Slebos et al., A novel host cell reactivation assay to assess homologous recombination capacity in human cancer cell lines. Biochem Biophys Res Commun. Feb. 16, 2001;281(1):212-9.
Stark et al., Heritable and non-genetic factors as variables of pharmacologic phenotypes in lymphoblastoid cell lines. Pharmacogenomics J. Dec. 2010;10(6):505-12. doi: 10.1038/tpj.2010.3. Epub Feb. 9, 2010.
Svilar et al., Base excision repair and lesion-dependent subpathways for repair of oxidative DNA damage. Antioxid Redox Signal. Jun. 15, 2011;14(12):2491-507. doi: 10.1089/ars.2010.3466. Epub Oct. 28, 2010.
Touati et al., Deficiency in OGG1 protects against inflammation and mutagenic effects associated with H. pylori infection in mouse. Helicobacter. Oct. 2006;11(5):494-505.
Trapnell et al., Differential gene and transcript expression analysis of RNA-seq experiments with TopHat and Cufflinks. Nat Protoc. Mar. 1, 2012;7(3):562-78. doi: 10.1038/nprot.2012.016.
Van't Veer et al., Enabling personalized cancer medicine through analysis of gene-expression patterns. Nature. Apr. 3, 2008;452(7187):564-70. doi: 10.1038/nature06915.
Viswanathan et al., Phenotypic change caused by transcriptional bypass of uracil in nondividing cells. Science. Apr. 2, 1999;284(5411):159-62.
Walmacq et al., Mechanism of translesion transcription by RNA polymerase II and its role in cellular resistance to DNA damage. Mol Cell. Apr. 13, 2012;46(1):18-29. doi: 10.1016/j.molcel.2012.02.006. Epub Mar. 8, 2012.
Westra et al., Identification of the persistently bound form of the carcinogen N-acetyl-2-aminofluorene to rat liver DNA in vivo. Chem Biol Interact. Oct. 2, 1976;15(2):149-64.
Wilson et al., Variation in base excision repair capacity. Mutat Res. Jun. 3, 2011;711(1-2):100-12. doi: 10.1016/j.mrfmmm.2010.12.004. Epub Dec. 15, 2010.
Wood et al., Single cell trapping and DNA damage analysis using microwell arrays. Proc Natl Acad Sci USA. Jun. 1, 2010;107(22):10008-13. doi: 10.1073/pnas.1004056107. Epub May 13, 2010.
Zhou et al., Preparation of heteroduplex enhanced green fluorescent protein plasmid for in vivo mismatch repair activity assay. Anal Biochem. May 1, 2009;388(1):167-9. doi: 10.1016/j.ab.2009.02.020. Epub Feb. 25, 2009. Erratum in: Anal. Biochem. Feb. 15, 2010;397(2):265.
International Search Report and Written Opinion for PCT/US2012/056433 dated Nov. 29, 2012.
International Preliminary Report on Patentability for PCT/US2012/056433 dated Apr. 3, 2014.

(56) References Cited

OTHER PUBLICATIONS

Li et al., DNA repair phenotype and cancer susceptibility—a mini review. Int J Cancer. Mar. 1, 2009;124(5):999-1007. doi: 10.1002/ijc.24126.

* cited by examiner a) RNAseq

ACCCAATCCGCCCT
ACCCGATCCGCCCT b) RNAseq

ACCCAATCCGCCCT
A(6-8bp del)CT c) DNAseq d) DNAseq

*Reduction in size between amplified plasmid and amplified cDNA is due to loss of chimeric intron (136 basepairs)

Multiple lesions in a Single Plasmid:

```
MUT:---CCC---
    ---GGG---(transcribed DNA strand)
       |
       Me

---CCC---(mRNA) - 75% Pro
  &    ---UCC---(mRNA) - 25% Ser
```

FIGURE 43

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
ttgctaacgc agtcagtgct                                                    20

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
gcattctagt tgtggtttgt cc                                                 22

<210> SEQ ID NO 3
<211> LENGTH: 102
<212> TYPE: DNA
<213> ORGANISM: Artificial Sequence
<220> FEATURE:
<223> OTHER INFORMATION: Synthetic Oligonucleotide

<400> SEQUENCE: 3
ggtaccgcca tcatgaagtt taaacaagct tgaattctct agagatatcc tgcagagatc        60
tggatccctc gaggctagcg cggccgcgtt taaacagagc tc                          102

<210> SEQ ID NO 4
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 4
atcgtgcgaa gcattacgca ctaacc                                             26

<210> SEQ ID NO 5
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 5
atcgtgcgaa gcattactca ctaacc                                             26

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 6
tcagggcgga ttgggtgc                                                      18

<210> SEQ ID NO 7
<211> LENGTH: 18
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (11)..(12)
<223> OTHER INFORMATION: thymine-thymine cis-syn cyclobutane dimer

<400> SEQUENCE: 7
tcagggcgga ttgggtgc                                              18

<210> SEQ ID NO 8
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 8
acccaatccg ccct                                                  14

<210> SEQ ID NO 9
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 9
acccgatccg ccct                                                  14
```

METHODS AND KITS FOR DETERMINING DNA REPAIR CAPACITY

RELATED APPLICATIONS

This application is a national stage filing under U.S.C. § 371 of PCT International Application PCT/US2012/056433, filed Sep. 20, 2012. Application PCT/US2012/056433 claims priority under 35 U.S.C. § 119(e) of U.S. provisional application Ser. No. 61/536,659, entitled "DNA REPAIR CAPACITY KIT" filed Sep. 20, 2011, the disclosure of which is incorporated by reference herein in its entirety.

GOVERNMENT SUPPORT

This invention was made with government support under Grant No. OD006422 awarded by the National Institutes of Health. The government has certain rights in the invention.

FIELD OF THE INVENTION

The field of invention relates to methods, compositions, vectors and kits for determining DNA repair capacity.

BACKGROUND OF THE INVENTION

DNA is under constant assault from damaging agents that produce a complex array of lesions. Left unrepaired, these lesions have the potential to result in cell death, or may lead to mutations that alter the biology of the cell and compromise the health of the organism, leading to degenerative diseases, cancer, and death. Consequently, inter-individual variation in the ability to respond to DNA damage is a critical component in answering a central question in biology: why do some people develop disease, while others do not?

Numerous human diseases are associated with mutations in DNA repair genes, and genetic tests are now available for a subset of highly penetrant mutations. Oncologists have begun to use these tests to tailor medical treatment and prevention to individual needs, for example by recommending specific cancer screening programs to patients based on their genetic susceptibility. Despite the enormous insight that has been gained from genetic screens, robust predictions of phenotype and disease susceptibility are hindered by epigenetic complexity, tissue-specific variability in gene expression, uncharacterized mutations, and variability in lifestyle and environmental exposure. Consequently, phenotypic screens are needed to complement genetic screens.

SUMMARY OF THE INVENTION

In one aspect, the disclosure provides methods, compositions, vectors and kits for determining DNA repair capacity.

In one aspect, the disclosure provides methods of determining DNA repair capacity in a cell. In some embodiments, the method of determining DNA repair capacity in a cell comprises introducing one or more DNA repair reporter vectors into a cell, and determining the capacity of the cell to process the one or more DNA repair reporter vectors thereby determining the DNA repair capacity in the cell.

In one aspect, the disclosure provides methods of determining DNA repair capacity of a subject. In some embodiments, the method of determining DNA repair capacity of a subject comprises introducing one or more DNA repair reporter vectors into cells obtained from a subject, and determining the capacity of the cells to process the one or more DNA repair reporter vectors thereby determining the DNA repair capacity of the subject. In some embodiments, the cells obtained from the subject are blood cells.

In one aspect, the disclosure provides methods of determining the propensity of a subject to respond to a cancer treatment regimen. In some embodiments, the method determining the propensity of a subject to respond to a cancer treatment regimen comprises introducing one or more DNA repair reporter vectors into cells obtained from a subject, wherein the one or more DNA repair reporter vectors comprise one or more lesions that are representative of a cancer treatment regimen, and determining the capacity of the cells to process the one or more DNA repair reporter vectors thereby determining the propensity of the subject to respond to the cancer treatment regimen. In some embodiments, the cells obtained from the subject are cancer cells. In some embodiments, the method further comprises comparing the capacity of the cancer cells to process the one or more DNA repair reporter vectors to the capacity of non-cancer cells to process the one or more DNA repair reporter vectors. In some embodiments, the lesions that are representative of a cancer treatment regimen comprise DNA-crosslinks. In some embodiments, the lesions that are representative of a cancer treatment regimen comprise DNA lesions that block transcription. In some embodiments, the lesions that are representative of a cancer treatment regimen comprise DNA lesions that induce transcription errors. In some embodiments, the lesions that are representative of a cancer treatment regimen comprise DNA alkylation damage. In some embodiments, the lesions that are representative of a cancer treatment regimen comprise $O^6$-methyl-guanine. In some embodiments, the lesions that are representative of a cancer treatment regimen comprise $N^7$-methylguanine.

In one aspect, the disclosure provides methods of determining the susceptibility of a subject to an environmental condition. In some embodiments, the method of determining the susceptibility of a subject to an environmental condition comprises introducing one or more DNA repair reporter vectors into cells obtained from a subject, wherein the one or more DNA repair reporter vectors comprise lesions that are representative of an environmental condition, and determining the capacity of the cells to process the one or more DNA repair reporter vectors thereby determining the susceptibility of the subject to the environmental condition. In some embodiments, the environmental condition is sunlight exposure. In some embodiments, the lesions that are representative of sunlight exposure comprise thymine dimers. In some embodiments, the environmental condition is ionizing radiation. In some embodiments, the lesions that are representative of ionizing radiation comprise DNA double strand breaks. In some embodiments, the environmental condition is exposure to a carcinogenic compound. In some embodiments, the environmental condition is exposure to one of more of the conditions of Table A.

In some embodiments of any of the methods provided herein, processing the one or more DNA repair reporter vectors comprises modifying a DNA lesion present in the one or more DNA repair reporter vectors.

In some embodiments of any of the methods provided herein, processing is detected by a change in a fluorescence signal.

In some embodiments of any of the methods provided herein, processing is detected by a change in the transcribed sequence of the one or more DNA repair reporter vectors.

In some embodiments of any of the methods provided herein, processing is detected by a change in the amount of transcribed sequence of the one or more DNA repair reporter vectors.

In some embodiments of any of the methods provided herein, DNA repair is nucleotide excision repair, homologous recombination, non-homologous end joining, microhomology mediated end joining, direct reversal, base excision repair, mismatch repair or interstrand crosslink repair.

In one aspect, the disclosure provides methods of determining multiple DNA repair capacities in a cell. In some embodiments, the method the method of determining multiple DNA repair capacities in a cell comprises introducing multiple DNA repair reporter vectors into a cell, and determining the capacity of the cell to process the multiple DNA repair reporter vectors thereby determining multiple DNA repair capacities in the cell. In some embodiments, the multiple DNA repair reporter vectors comprises at least two DNA repair reporter vectors. In some embodiments, the multiple DNA repair reporter vectors comprises at least four DNA repair reporter vectors. In some embodiments, each DNA repair reporter vector of the multiple DNA repair reporter vectors comprises a unique DNA lesion. In some embodiments, each DNA repair reporter vector of the multiple DNA repair reporter vectors comprises a specific number of DNA lesions. In some embodiments, each DNA repair reporter vector of the multiple DNA repair reporter vectors comprises a number of DNA lesions corresponding to a specific dose of damaging agent. In some embodiments, the multiple DNA repair reporter vectors comprise lesions susceptible to processing by nucleotide excision repair, homologous recombination, non-homologous end joining, microhomology mediated end joining, direct reversal, base excision repair, mismatch repair or interstrand crosslink repair.

In one aspect, the disclosure provides kits comprising one or more DNA repair reporter vectors and instructions for use of the one or more DNA repair reporter vectors. In some embodiments, the kit comprises at least two DNA repair reporter vectors. In some embodiments, the kit comprises at least four DNA repair reporter vectors. In some embodiments, each DNA repair reporter vector of the kit comprises a unique DNA lesion. In some embodiments, the DNA repair reporter vectors of the kit comprise lesions susceptible to processing by nucleotide excision repair, homologous recombination, non-homologous end joining, microhomology mediated end joining, direct reversal, base excision repair, mismatch repair or interstrand crosslink repair. In some embodiments, the kit further comprises a cell line with a known DNA repair capacity.

In one aspect, the disclosure provides kits for determining the propensity of a subject to respond to a cancer treatment regimen comprising one or more DNA repair reporter vectors, wherein the one or more DNA repair reporter vectors comprise lesions representative of a cancer treatment regimen, and instructions for use of the one or more DNA repair reporter vectors. In some embodiments, the kit comprises at least two DNA repair reporter vectors. In some embodiments, the kit comprises at least four DNA repair reporter vectors. In some embodiments, each DNA repair reporter vector of the kit comprises a unique DNA lesion. In some embodiments, the kit further comprises a cell line with a known DNA repair capacity.

In one aspect, the disclosure provides kits for determining the susceptibility of a subject to an environmental condition comprising one or more DNA repair reporter vectors, wherein the one or more DNA repair reporter vectors comprise lesions representative of an environmental condition, and instructions for use of the one or more DNA repair reporter vectors. In some embodiments, the kit comprises at least two DNA repair reporter vectors. In some embodiments, the kit comprises at least four DNA repair reporter vectors. In some embodiments, each DNA repair reporter vector of the kit comprises a unique DNA lesion. In some embodiments, the kit further comprises a cell line with a known DNA repair capacity.

In one aspect, the disclosure provides kits for determining the repair capacity of a cell line comprising one or more DNA repair reporter vectors, wherein the one or more DNA repair reporter vectors allow for the determination of the repair capacity of the cell line, and instructions for use of the one or more DNA repair reporter vectors. In some embodiments, the kit comprises at least two DNA repair reporter vectors. In some embodiments, the kit comprises at least four DNA repair reporter vectors. In some embodiments, each DNA repair reporter vector of the kit comprises a unique DNA lesion. In some embodiments, the kit further comprises a cell line with a known DNA repair capacity.

In one aspect, the disclosure provides a DNA repair reporter vector comprising a DNA lesion and a fluorescence reporter gene. In one aspect, the disclosure provides a DNA lesion and a first nucleic acid sequence allowing for the identification of the DNA lesion. In one aspect, the disclosure provides a DNA repair reporter vector comprising a DNA lesion and a first nucleic acid sequence allowing for the identification of the DNA lesion further comprising a fluorescence reporter gene. In some embodiments, the DNA repair reporter vector further comprises a second nucleic acid sequence allowing for the identification of the DNA repair reporter vector. In some embodiments, the first nucleic acid sequence allows for the determination of the processing of the DNA lesion. In some embodiments, the processing is detected by a change in the transcribed sequence of the nucleic acid sequence. In some embodiments, the processing is detected by a change in the amount of transcribed sequence of the nucleic acid sequence. In some embodiments, the DNA lesion is susceptible to processing by nucleotide excision repair, homologous recombination, non-homologous end joining, microhomology mediated end joining, direct reversal, base excision repair, mismatch repair or interstrand crosslink repair. In some embodiments, the DNA lesion is representative of a cancer treatment regimen. In some embodiments, the DNA lesion is representative of an environmental condition.

These and other aspects and embodiments of the invention are described in greater detail below.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 43 is an illustration showing that when $O^6$MeG is present in the transcribed strand, some mRNA will contain U, and will be translated into wild type mPlum protein.

DETAILED DESCRIPTION OF THE INVENTION

Figure 1:
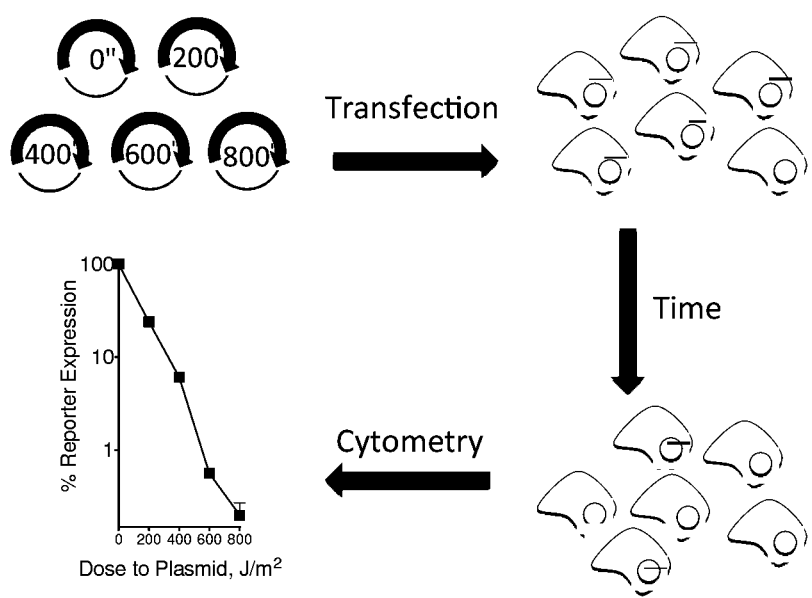
FIG. 1 is an illustration showing an overview of the HT-HCR methodology. DNA lesions are introduced into fluorescent reporter plasmids in vitro. Numbers labeling the plasmids represent the dose (in $J/m^2$) of UV radiation. Following treatment, plasmids were combined and co-transfected into cells. After 18 or 40 hours incubation, cells were assayed for fluorescence by flow cytometry. Comparison of fluorescence signals to those from cells transfected with undamaged plasmids yields a dose-response curve (experimental data for GM02344 with plasmid combination #1 in Table 2).

In one aspect, the disclosure provides methods, vectors, compositions and kits for determining DNA repair capacity in a cell or a subject.

In one aspect, the disclosure provides methods of determining DNA repair capacity in a cell. In some embodiments, the disclosure provides methods of determining DNA repair capacity in a cell, the method comprising introducing one or more DNA repair vectors into a cell, and determining the capacity of the cell to process the one or more DNA repair vectors thereby determining the DNA repair capacity of the cell.

DNA is constantly bombarded by both endogenous and environmental DNA damaging agents. Failure to repair this damage is a risk factor for disease, and the available data point to a wide range of capacity to repair DNA damage in the human population. However, prior to methods provided in the instant disclosure, the complexity and multitude of DNA repair pathways have thus far precluded large-scale comprehensive investigations of inter-individual differences in DNA repair capacity.

In one aspect, the disclosure provides multiplexed, high-throughput, quantitative assays for DNA repair capacity. In some embodiments, the DNA repair capacity is evaluated through fluorescence reporters. In some embodiments, a high throughput flow cytometric host cell reactivation assay (HT-HCR) with six fluorescent reporters is provided (Also referred to herein as "Lumens"). Unexpectedly, it was found that a system with the multiple reporters could be used to evaluate one or more aspects of the DNA repair capacity in a cell or subject. In some embodiments, the HT-HCR assay has been used to measure simultaneously host cell reactivation of multiple plasmid DNA reporters treated with several doses of UVC.

In one aspect, the disclosure provides sequencing based methods to determine the DNA repair capacity in a cell. In some embodiments, the sequence based method is a next generation sequencing based host cell reactivation assay (HCR-Seq; Also referred to herein as "Sequens"). It was surprisingly found that sequencing based methods allow for the multiplex detection of the DNA repair of any DNA repair pathway. As provided herein, in some embodiments, in a single DNA sequencing lane 40 reporters or more could be detected simultaneously and independently. Thus, for the first time a method is provided that allows for the independent detection of multiple reporters (up to 4000, or more), allowing for studies of DNA repair capacity in large populations. The single nucleotide resolution of the HCR-Seq data permits discovery and quantitation of rare transcriptional mutagenesis events due to lesion bypass by RNA polymerase, and thus allows for the detection of DNA repair of any DNA repair pathway acting on a lesion that changes the transcribed sequence or the amount of transcript produced. Such lesions exist for all of the major DNA repair pathways. The methods provided herein allow for a synthesis of gene expression patterns and protein biomarkers that can help to personalize the prevention, diagnosis and treatment of cancer in a single assay. The hurdles of molecular complexity and heterogeneity among individuals and across disease states can be addressed by determining the DNA repair capacity according to the methods provided herein.

Direct evidence of a relationship between DNA repair capacity and cancer susceptibility comes from several studies of nucleotide excision repair (NER) [5]. Individuals with Xeroderma Pigmentosum (XP) are highly deficient for NER, and suffer an estimated 2000-fold increased risk of developing cancer in sun-exposed skin [6]. Epidemiological studies in apparently healthy individuals demonstrated a wide range of NER capacity, and an apparent link between NER capacity and cancer susceptibility [5, 7-9]. Additional studies have examined links between other repair pathways and cancer [10, 11].

Despite a clear relationship between DNA repair capacity and human health, the majority of these epidemiological studies have been relatively small, and most have been focused on the NER pathway. A major barrier to larger studies that encompass additional pathways is the lack of a high throughput assay for DNA repair capacity in multiple DNA repair pathways.

In one aspect, the disclosure provided host cell reactivation (HCR) assay. Host cell reactivation (HCR) assays allow for the measuring DNA repair capacity in intact cells by using DNA repair reporter vectors. In some embodiments, in a typical HCR assay, a plasmid that expresses a reporter gene is exposed to a DNA damaging agent that generates transcription-blocking lesions, and then the plasmid is transfected into living cells. In the absence of repair, expression of the reporter gene is inhibited. However, if the cells are able to repair the damage, the transcription blocking lesions are removed, and expression of the reporter is reactivated.

Prior to the instant disclosure a high throughput assay system for determining DNA repair capacity was not available. Up to now, the standard reporter used to determine DNA repair capacity is chloroamphenicol acetyl transferase (CAT). A major limitation of this reporter is the need to lyse cells following transfection with subsequent liquid scintillation or thin layer chromatography analysis, and the requirement of radiolabeled substrates. A further limitation is the inability to control for transfection efficiency. The need for radiolabels and the inability to control for transfection efficiency have been overcome through the use of a dual luciferase reporter [16], however this methodology retains the need to lyse cells and depends on exogenous reagents that must be added to lysates to assay for the reporter. While fluorescent reporters have become available [17], it has not been possible to multiplex such assays. Prior to the methods provided herein multiplex determination of DNA repair capacity could not be achieved because of (i) the inability to measure more than one DNA repair signal at a time, (ii) the lack of a general method of detecting repair of lesions that can be bypassed by RNA polymerase and (iii) the lack of a thorough validation of fluorescent reporter systems against the standard CAT reporter systems.

In one aspect, the disclosure provides multiplex methods for determining DNA repair capacity in a cell. In some embodiments, the multiplex assay is a fluorescence based assay. In some embodiments, the multiplex assay is a high throughput host cell reactivation assay (HT-HCR) that makes use of multiple fluorescent reporter proteins in a single assay to measure multiple separate repair processes. In some embodiments, the multiplex assay is a sequence based assay. In some embodiments, the multiplex assay is HCR-Seq, a method that provides the ability to measure thousands of independent repair processes in a single assay.

Determining DNA Repair Capacity

The genetic material of cells is continually challenged by intracellular and extracellular conditions, such as cell metabolites, radiation and exposure to environmental agents. Exposure to these conditions can lead to DNA damage. DNA damage is unwanted because it can lead to the blocking of replication, which would result in the death of the cell, blocking of transcription which may lead to the cell death if essential proteins are involved, and mutagenesis. Mutagenesis may be lethal if the function of an essential protein is compromised or, can result in uncontrolled cell growth (e.g. carcinogenesis) if the activity of a tumor suppressor gene is compromised. Cells have evolved a variety of DNA repair mechanisms to remove or suppress DNA damage. These mechanisms include nucleotide excision repair, which is generally directed against multi base pair lesions, base excision repair, which is generally directed against single base lesion, mismatch repair, which removes mismatched base pairs, end joining, which is directed against double strand breaks, direct reversal, which generally removes chemical modifications from DNA bases, and recombinational repair, which removes a variety of lesions including deletions and replication blocking lesions (An overview of the various DNA repair pathways can be found for instance in *DNA Repair and Mutagenesis*, Friedberg et al., ASM Press). Each repair pathway uses a variety of DNA repair enzymes that act on and process the DNA lesion. The importance of DNA repair is exemplified in people who are deficient for a particular repair mechanism. For instance, subjects suffering from Xeroderma Pigmentosum are deficient in one of the proteins of the nucleotide excision repair pathway. These subjects have only a very limited ability to process cyclobutane pyrimidine dimer DNA lesions (such as thymine dimers) and (6-4) photoproducts that are caused by exposure to sunlight, and they are at high risk for developing skin cancers. Similarly, people with mutations in genes coding for enzymes involved in mismatch repair have been shown to be at increased risk for colorectal cancer.

In one aspect, the disclosure provides a method of determining the DNA repair capacity of a subject. In some embodiments, the method of determining the DNA repair capacity of a subject comprises introducing one or more DNA repair reporter vectors into cells obtained from a subject, and determining the capacity of the cells to process the one or more DNA repair reporter vectors thereby determining the DNA repair capacity of the subject. In some embodiments, the cells obtained from the subject are blood cells.

In one aspect, the disclosure provides a method of determining the propensity of a subject to respond to a cancer treatment regimen. In some embodiments, the method of determining the propensity of a subject to respond to a cancer treatment regimen comprises introducing one or more DNA repair reporter vectors into cells obtained from a subject, wherein the one or more DNA repair reporter vectors comprise one or more lesions that are representative of a cancer treatment regimen, and determining the capacity of the cells to process the one or more DNA repair reporter vectors thereby determining the propensity of the subject to respond to the cancer treatment regimen. In some embodiments, the cells obtained from the subject are cancer cells. In some embodiments, the method of determining the propensity of a subject to respond to a cancer treatment regimen further comprises comparing the capacity of the cancer cells to process the one or more DNA repair reporter vectors to the capacity of non-cancer cells to process the one or more DNA repair reporter vectors.

Every person has a unique DNA repair capacity profile which is correlated to the activity of specific DNA repair pathways (See e.g., Fry, R. C. et al. Genomic predictors of inter-individual differences in response to DNA damaging agents. *Genes Dev.* 22, 2621-262). Thus, for instance, a first person may have a very active nucleotide excision repair but may have low base excision repair activity. A second person may have both low activity for nucleotide excision repair and base excision repair but may have a high recombinational repair activity. Some people may have more activity in all DNA repair pathways compared to other people. When a person is exposed to a DNA damaging event, such as cancer chemotherapy, sunlight or a different environmental condition, resulting in DNA lesions, the response to these lesions will vary from person to person depending on their DNA repair capacity profile. The disclosure provides methods to assess how a person will respond to a variety of DNA damaging events.

In one aspect, the disclosure provides methods of determining DNA repair capacity in a cell. In some embodiments, the method of determining DNA repair capacity in a cell comprises introducing one or more DNA repair reporter vectors into a cell, and determining the capacity of the cell to process the one or more DNA repair reporter vectors thereby determining the DNA repair capacity in the cell. The methods of the disclosure are not limited to a particular cell type and any cell into which DNA repair vectors can be introduced can be evaluated according to the methods of the invention. Cells of interest, for instance, are cells of which the DNA repair capacity is unknown or cells that are to be challenged with one or more conditions that can cause DNA damage. Cells in which the DNA repair capacity is to be determined can be cells obtained from subjects, including humans and animals. Cells obtained from a subject include blood cells, skin cells and cancerous cells (e.g., through biopsy). Cells in which the DNA repair capacity is to be determined can be transformed cells that can divide indefinitely, or primary cells that are expected to divide only a limited number of times. In some embodiments, the cells in which the DNA repair capacity is to be determined are cancer cells. Determining the DNA repair capacity in a cancer cell provides insight into therapeutic treatment options for the particular cancer regimen. Thus, established cancer cell lines can be assayed for their repair capacities. For instance, a colon cancer cell line can be investigated for its proficiency in base excision repair and nucleotide excision repair. If the cancer cell line shows to be more proficient in base excision repair than in nucleotide excision repair the cancer could be treated with a chemotherapeutic agent (e.g., cisplatin), which results in DNA damage which is normally processed by nucleotide excision repair. Because the cancer is less proficient in repairing lesions processed by nucleotide excision repair, subjecting the cell to such lesions should offer a preferred way of killing the cell. Knowing the repair capacity of the cancer cell line in multiple DNA repair pathways helps to refine the chemotherapeutic window. If the cancer cell line is deficient in direct reversal of $O^6$-methylguanine lesions, but is proficient in all other pathways, the cancer could be treated with a chemotherapeutic agent (e.g., temozolomide) that induces $O^6$-methylguanine. If however the cancer cell line is deficient in both direct reversal of $O^6$-methylguanine and mismatch repair, the cells will not be sensitive to chemotherapeutic agents that induce $O^6$-methylguanine, and a different route of treatment should be sought. In some embodiments, the DNA repair profile of a cancer obtained from a subject can be evaluated prior to chemotherapeutic treatment. Thus, a cancer cell can be obtained from a subject and the DNA repair profile of the cancer cell evaluated. The subsequent chemotherapy can take into account the DNA repair profile of the cancer cell. In some embodiments, the DNA repair profile of the cancer cell of a subject can be compared to the DNA repair profile of non-cancerous cells from the subject. Thus, a therapeutic window can be developed by comparing the DNA repair profile of a cancer cell of a subject to the DNA repair of a non-cancerous cell in subject. This method of maximizing the efficacy of treatment while minimizing side effects to the patient avoids the still common practice of determining the best chemotherapy regimen by trial-and-error.

In some embodiments, one or more cell types can be obtained from a subject and the DNA repair profile of the cells determined. In some embodiments, the DNA repair profile of subject is determined by determining the DNA repair profile of one or more cell types obtained from the subject. In some embodiments, the DNA repair profile of a subject can be determined by determining the DNA repair profile of a representative cell type. In some embodiments, the representative cell type is a blood cell. Knowing the DNA repair profile of subject allows for the development of the therapeutic window and of the tailoring of cancer chemotherapy. Thus, a person classified as being highly proficient in DNA base excision repair can be given an appropriate dose (e.g., increased dose) of cancer chemotherapy that induces DNA lesions that are processed by base excision repair. The healthy cells of a subject as being highly proficient in DNA base excision repair are expected to process the increased number of DNA lesions caused by the chemotherapeutic agent because of the increased proficiency in base excision repair.

In some embodiments, the DNA repair profile of a person is compared to the DNA repair profile of a cancer cell line. For instance, the DNA repair profile of a particular cancer cell may be known from previous experiments. For instance, it may be known that melanoma is particularly susceptible to ionizing radiation in general, and the susceptibility of the cancer cell may be correlated against the DNA repair profile of the person, e.g., as determined by evaluating the DNA repair profile of a representative cell line of that person. An appropriate chemotherapeutic regimen may be decided on based on the DNA repair capacity of the subject and the DNA repair profile of the cancer cell.

In one aspect, the disclosure provides methods of determining the susceptibility of a subject to an environmental condition. In some embodiments, the method of determining the susceptibility of a subject to an environmental condition comprises introducing one or more DNA repair reporter vectors into cells obtained from a subject, wherein the one or more DNA repair reporter vectors comprise lesions that are representative of an environmental condition, and determining the capacity of the cells to process the one or more DNA repair reporter vectors thereby determining the susceptibility of the subject to the environmental condition. In some embodiments, the environmental condition is sunlight exposure. In some embodiments, the lesions that are representative of sunlight exposure include thymine dimers. In some embodiments, the environmental condition is ionizing radiation. In some embodiments, the lesions that are representative of ionizing radiation include DNA double strand breaks. In some embodiments, the environmental condition is exposure to a carcinogenic compound.

In one aspect, the disclosure provides methods of determining the susceptibility of a subject to an environmental condition. Cells and subjects are constantly challenged by conditions that can damage DNA. Exposure to some of these conditions cannot be avoided, e.g., oxidative damage from cell metabolism. However, exposure to some of these conditions that can damage DNA can be avoided or minimized (e.g., ionizing radiation, sunlight). In one aspect, the disclosure provides methods for providing subjects with information allowing the subjects to modify their behavior accordingly. For instance, the methods provided herein allow for the determination of a subject's susceptibility to sunlight. A representative cell from a subject (e.g. skin cell or blood cell) can be investigated for its ability to process DNA damage caused by sunlight. If a person has only a low ability to process DNA lesions caused by sunlight that person should avoid sunlight in order to minimize the chance of developing skin cancer. If a subject has cells that are highly proficient in repairing DNA lesions caused by sunlight that person does not need to be extremely diligent in avoiding sunlight. According to the methods provided herein subjects can be evaluated for their susceptibility to a variety of environmental conditions. For instance, a subject can be investigated for its susceptibility to ionizing radiation, an environmental carcinogen, etc. Once a subject knows its susceptibility to a particular environmental condition, that person can alter its lifestyle and try to minimize exposure to the environmental condition.

Lesions

In one aspect, the disclosure provides methods, compositions, vectors and kits for determining the DNA repair capacity in a cell or a subject. In one aspect, the disclosure provides DNA repair reporter vectors for determining the DNA repair capacity in a cell or a subject. In some embodiments, the DNA repair reporter vectors include one or more lesions. A "lesion", or "DNA lesion", as used herein, refers to any structural modification of the DNA that distinguishes the DNA from correctly base-paired DNA, DNA lesion include DNA base modifications, mutations, deletions, DNA cross-links, uracil incorporation, modifications of the phosphodiester backbone etc. (See also Tables A-D below). For instance, lesions include DNA alkylation lesions (See e.g., Shrivastav et al., Carcinogenesis 31, 2010, p 59-70), oxidative DNA damage (Cooke et al., FASEB J 17, 195-1214), and mismatches between natural and non-natural DNA base pairs.

In one aspect, the lesions used in the methods, compositions, vectors and kits provided herein are representative of a cancer chemotherapy regimen. That is, the lesion is generated by exposing cells and/or a subject to cancer chemotherapy. For instance, alkylating agents such as nitrosoureas are commonly used in cancer chemotherapy. Exposure of cells to nitrosourea results in a variety of DNA lesions including $O^6$-methyl-guanine. Thus, the lesion $O^6$-methyl-guanine is representative of a cancer chemotherapy regime using nitrosoureas, and such lesions can be used according to the methods provided herein to determine the susceptibility of a cell or subject to that particular cancer chemotherapy regimen. Similarly, an MNNG (N-methyl-N'-nitro-N nitrosoguanidine) based cancer chemotherapy regimen would result in $N^7$-methylguanine lesions in the DNA. DNA repair reporter vectors comprising $N^7$-methylguanine can therefore be used to determine the susceptibility of a cell or subject to a cancer chemotherapy regimen that includes MNNG. Analogously, cancer chemotherapy that includes ionizing radiation will result in oxidative lesions and DNA strand breaks and oxidative lesions and DNA strand breaks can are therefore representative of cancer chemotherapy regimen that includes ionizing radiation. It should be appreciated that lesions can be representative for more than one cancer chemotherapy regimen, and that more than one lesion may be necessary to fully represent a chemotherapy regimen. For instance, a DNA strand break can be generated by exposure to a variety of lesions, and MNNG generates $O^6$-methyl-guanine in addition to $N^7$-methylguanine. A person of skill in the art can rely on the literature to provide others lesions that representative of a particular cancer chemotherapy regimen.

In some embodiments of the methods, compositions, vectors and kits provided herein the lesions that are representative of a cancer treatment regimen comprise DNA-crosslinks. In some embodiments, the lesions that are representative of a cancer treatment regimen comprise DNA lesions that block transcription. In some embodiments, the lesions that are representative of a cancer treatment regimen comprise DNA lesions that induce transcription errors. In some embodiments the lesions that are representative of a cancer treatment regimen comprise DNA alkylation damage. In some embodiments, the DNA alkylation damage comprises $O^6$-methyl-guanine. In some embodiments, the DNA alkylation damage comprises $N^7$-methylguanine.

In one aspect, the lesions used in the methods, compositions, vectors and kits provided herein are representative of environmental conditions. Similarly to the cancer treatment regimens discussed above, certain environmental conditions will result in specific DNA lesions. For instance, sunlight exposure will result in the formation of thymine dimers in cells, which are therefore representative of exposure to sunlight. It should be appreciated that lesions can be representative for one or more environmental conditions and that more than one lesion may be necessary to fully represent an environmental condition. It should also be appreciated that lesions can be representative for one or more environmental conditions and one/or more cancer treatment regimens. In some embodiments, the environmental condition is sunlight exposure. In some embodiments, the lesion that is representative of sunlight exposure is a thymine dimer. In some embodiments, the environmental condition is ionizing radiation. In some embodiments, the lesion that is representative of ionizing radiation is a DNA double strand breaks. In some embodiments, the environmental condition is a carcinogenic compound. Embodiments of additional environmental conditions and representative DNA lesions are provided in Table A. In addition, a person of ordinary skill in the art can rely on the literature to provide information on additional lesions that are representative of environmental conditions.

TABLE A

Environmental conditions and representative DNA lesions

| Exposure Condition | Representative damaging agent | Route of exposure | Types of Lesions | A Representative Lesion | References |
|---|---|---|---|---|---|
| Sunlight | UV light | Skin | Cyclobutane pyrimidine dimers and (6-4) photoproducts | thymine-thymine cis-syn cyclobutane dimer | [1] |
| Ionizing Radiation | X-rays, free radicals | Ambient radon gas, X-irradiation | Strand breaks, free radical induced damage | Double strand break | [2] |
| Tobacco smoke | Polycyclic aromatic hydrocarbons | Inhalation | Benzo[a]pyrene adducts | (+)-anti-benzo[a]pyrene diol epoxide -$N^2$-dG | [3] |
| *Aspergillus* (fungus) | Aflatoxin | Ingestion | Aflatoxin adducts | 8,9-dihydro-8-(N7-guanyl)-9-hydroxyaflatoxin $B_1$ | [4] |
| Drugs | Psoralen | Topical, ingestion, injection | DNA cross-links (various drug dependent lesions) | Psoralen Interstrand cross-link | [5] |
| Carcinogens in food | Heterocyclic Amines | Ingestion | amino-imidazoazaarene adducts | N-(deoxyguanosin-8-yl)- 2-amino-3-methylimidazo[4,5-f]quinoline | [6] |
| Air pollution | Reactive oxygen, nitrogen and free radicals | Inhalation | Hydrogen peroxide | 1-$N^6$-ethenoadenine | [7] |
| Exhaust Fumes | Polycyclic aromatic hydrocarbons | Inhalation | Benzo[a]pyrene adducts | (+)-anti-benzo[a]pyrene diol epoxide -$N^2$-dG | [3] |
| Industrial Chemicals | N-2-Acetyl-2-Aminofluorene | Skin, eye, ingestion | Aromatic amines (various chemical dependent lesions) | N-(2'-deoxyguanosin-8-yl)-N-acetyl-2-aminofluorene | [8] |
| Helicobacter Pylori | Reactive oxygen, nitrogen and free radicals | Infection | Oxidative DNA damage | 8-oxo-guanine | [9] |
| Irritants in food | Reactive oxygen, nitrogen and free radicals | Inflammatory response to ingestion (eg gluten in coeliacs) | Oxidative and free radical induced damage | Thymine glycol | [10] |

TABLE A-continued

Environmental conditions and representative DNA lesions

| Exposure Condition | Representative damaging agent | Route of exposure | Types of Lesions | A Representative Lesion | References |
|---|---|---|---|---|---|
| Burning of biomass | Methyl halides | Inhalation | Alkylation damage of DNA bases | $O^6$-methylguanine | [11] |

1. Setlow, R.B. and W.L. Carrier, Pyrimidine dimers in ultraviolet-irradiated DNAs. Journal of Molecular Biology, 1966. 17(1): p. 237-&.
2. Iliakis, G., The role of DNA double strand breaks in ionizing radiation-induced killing of eukaryotic cells Bioessays, 1991. 13(12): p. 641-648.
3. Perlow, R.A., et al., DNA adducts from a tumorigenic metabolite of benzo a pyrene block human RNA polymerase II elongation in a sequence- and stereochemistry-dependent manner. Journal of Molecular Biology, 2002. 321(1): p. 29-47.
4. Essigmann, J.M., et al., Structural identification of major DNA adduct formed by aflatoxin-B1 in vitro. Proceedings of the National Academy of Sciences of the United States of America, 1977. 74(5): p. 1870-1874.
5. Cole, R.S., Psoralen monoadducts and interstrand cross-links in DNA. Biochimica Et Biophysica Acta, 1971. 254(1): p. 30-&.
6. Schut, H.A.J. and E.G. Snyderwine, DNA adducts of heterocyclic amine food mutagens: implications for mutagenesis and carcinogenesis. Carcinogenesis, 1999. 20(3): p. 353-368.
7. Marnett, L.J., Oxyradicals and DNA damage. Carcinogenesis, 2000. 21(3): p. 361-370.
8. Westra, J.G., E. Kriek, and H. Hittenhausen, Identification of persistently bound form of carcinogen N-acetyl-2-aminofluorene to rat liver DNA in vivo Chemico-Biological Interactions, 1976. 15(2): p. 149-164.
9. Touati, E., et al., Deficiency in OGG1 protects against inflammation and mutagenic effects associated with H-Pylori infection in mouse. Helicobacter, 2006. 11(5): p. 494-505.
10. Svilar, D., et al., Base Excision Repair and Lesion-Dependent Subpathways for Repair of Oxidative DNA Damage. Antioxidants & Redox Signaling, 2011. 14(12): p. 2491-2507.
11. Bolt, H.M. and B. Gansewendt, MECHANISMS OF CARCINOGENICITY OF METHYL HALIDES. Critical Reviews in Toxicology, 1993. 23(3): p. 237-253.

In one aspect, the disclosure provides methods of determining the DNA repair capacity in a cell or subject. In order to determine the DNA repair capacity in a cell or subject it may be desirable to determine the proficiency of one or more DNA repair pathways. In some embodiments, the disclosure provides methods allowing the determination of the proficiency of one or more DNA repair pathways in a cell or subject. Prior to the methods provided herein, it was not possible to adequately determine the proficiency of more than one DNA repair pathway in a cell using a single assay. In some embodiments, the disclosure provides methods using lesions that are susceptible to processing by one more DNA repair mechanisms to evaluate the DNA repair capacity. In some embodiments, the lesions are susceptible to processing by nucleotide excision repair, homologous recombination, non-homologous end joining, microhomology mediated end joining, direct reversal, base excision repair, mismatch repair or interstrand crosslink repair. In one aspect, the disclosure provides DNA repair reporter vectors comprising lesions that are susceptible to processing by one more DNA repair mechanisms that are used to evaluate the DNA repair capacity. In some embodiments, the lesions are susceptible to processing by nucleotide excision repair, homologous recombination, non-homologous end joining, microhomology mediated end joining, direct reversal, base excision repair, mismatch repair or interstrand crosslink repair.

In one aspect, the lesions used in the methods, compositions, vectors and kits provided herein are susceptible to processing by a specific DNA repair pathway. Thus, lesions can be parsed with a particular DNA repair pathway that acts on the lesion. Representative lesions that can be used to evaluate the proficiency of a DNA repair pathway are provided in Table B. For instance, nucleotide excision repair acts on thymine dimers and a thymine dimer lesion can therefore be used to determine the proficiency of nucleotide excision repair capacity in the cell and/or subject. It should be appreciated that more than one kind of lesion can be used to determine the strength of a DNA repair pathway in a cell. Thus, for instance, both a thymine dimer and cisplatin adducts can be used to evaluate the proficiency of nucleotide excision repair. It should also be appreciated that one lesion can be repaired by more than one DNA repair pathway (See e.g., Table C).

TABLE B

DNA repair pathways, representative lesions, and model cell lines useful in establishing repair assays.

| Repair Pathway | Representative Lesions | Example of Deficient Cell Line | Genotype | Corresponding Proficient Cell Line | Organism | Cell Type |
|---|---|---|---|---|---|---|
| Nucleotide Excision Repair (NER) | cys-syn thymine-thynine cyclobutane pyrimidine dimer | GM02344 | XPA mutant | GM01953 | Human | Lymphoblastoid |
| Homologous Recombination (HR) | double strand break, when a separate, intact homologous sequence is available | irs1 | XRCC3 mutant | irs1 + pXRCC3 | Hamster | Fibroblast |

TABLE B-continued

DNA repair pathways, representative lesions, and model cell lines useful in establishing repair assays.

| Repair Pathway | Representative Lesions | Example of Deficient Cell Line | Genotype | Corresponding Proficient Cell Line | Organism | Cell Type |
|---|---|---|---|---|---|---|
| Non Homologous End Joining (NHEJ) | double strand break in absence of homologous sequences | XR-C1 | DNA PKcs mutant | XR-C1 + Human Chromosome #8 | Hamster | Epithelial |
| Microhomology Mediated End Joining (MMEJ) | double strand break between microhomologies | BRCA1−/− MEFs | BRCA1−/− | Wild type MEFs | Mouse | Embryonic Fibroblasts |
| Direct Reversal (DR) | O6-methylguanine | TK6 | MGMT−/− | TK6 + MGMT | Human | Lymphoblastoid |
| Base Excision Repair (BER) | ethenoadenine | Aag−/− MEFs | Aag−/− | Aag−/− + Aag (complemented) | Mouse | Embryonic Fibroblasts |
| Mismatch Repair | G:G mismatch | HCT116 | MLH1 mutant | HCT116 + Human Chromosome #3 | Human | Colon carcinoma |
| Interstrand Crosslink Repair | Psoralen Crosslink | XP42RO | XPF mutant | C5RO | Human | Immortalized Fibroblasts |

TABLE C

Representative lesions and their associated DNA repair pathway

| Lesion | Main Repair Pathways |
|---|---|
| Cys-Syn Thymine-Thymine cyclobutane pyrimidine dimer | NER |
| Double strand break | HR, NHEJ, MMEJ |
| Single strand break | BER |
| Base mismatches | MMR, BER |
| Single base insertion loops | MMR |
| $O^6$-methylguanine | DR, NER, MMR |
| 1,$N^6$-ethenoadenine | BER, DR |
| 3,$N^4$-ethenocytosine | BER, DR |
| cisplatin adducts | Cross-link repair, NER, HR |
| abasic sites | BER |
| UV irradiation (Cyclobutane Pyrimidine Dimers and (6-4) photoproducts) | NER |
| Incubation with MNNG (methylated bases) | BER, DR |
| Incubation with Chloroacetaldehyde (etheno bases) | BER, DR |
| Incubation with psoralen + UVA irradiation | Cross-link repair, HR, NER |
| Incubation with BCNU | Cross-link repair, HR, NER |
| 7,8-Dihydro-8-oxoguanine (8-oxo-G) | BER |
| 7,8-Dihydro-8-oxoguanine (8-oxo-A) | BER |
| thymine glycol | BER |
| uracil | BER |
| hypoxanthine | BER |
| xanthine | BER |
| N7-methylguanine | BER |
| N3-methyladenine | BER |
| N1-methyladenine | BER, DR |
| N1-methylguanine | BER, DR |
| N3-methylcytosine | BER, DR |
| N7-methyladenine | BER |
| 8-methylguanine | BER |
| N3-methylguanine | BER |
| $O^2$-methylcytosine | BER |
| N3-methylthymine | DR |
| $O^2$-methylthymine | BER |
| $O^4$-methylthymine | DR, NER |
| 2,6-Diamino-4-hydroxy-5-formamidopyrimidine (FaPy-G) | BER |
| 4,6-Diamino-5-formamidopyrimidine (FaPy-A) | BER |
| $M_1A$ (malondialdehyde adduct of adenine) | NER |
| $M_1C$ (malondialdehyde adduct of cytosine) | NER |
| $M_1G$ (malondialdehyde adduct of guanine) | NER |
| 5,6-Dihydrothymine | BER |
| 5-Hydroxy-5,6-dihydroxythymine | BER |
| 5-Hydroxymethyluracil | BER |
| 5-Hydroxy-5-methylhydantoin | BER |
| 5-Hydroxy-5,6-dihydrocytosine | BER |

TABLE C-continued

Representative lesions and their associated DNA repair pathway

| Lesion | Main Repair Pathways |
|---|---|
| Cytosine glycol | BER |
| 5,6-dihydroxycytosine | BER |
| 5-Hydroxyhydantoin | BER |
| Methyltartonylurea | BER |
| 8,5'-Cyclodeoxyguanosine | NER |
| Urea | BER |
| C(5)-C(5) thymidine dihydrodimer | ? |
| N-formamidourea | ? |
| N-(deoxyguanosin-8-yl)-2-aminofluorene | NER |
| 3-(deoxyguanosin-$N^2$-yl)-N-acetyl-2-aminofluorene | NER |
| N-(Deoxyguanosin-8-yl)-N-acetyl-2-aminofluorene | NER |
| (+)-anti-benzo[a]pyrene diol epoxide-$N^2$-dG | NER |
| 8,9-dihydro-8-(N7-guanyl)-9-hydroxyaflatoxin $B_1$ | NER |
| N-(deoxyguanosin-8-yl)-2-amino-3-methylimidazo[4,5-f]quinoline | NER |
| 3-(deoxyguanosin-$N^2$-yl)-4-aminoquinoline-1-oxide | NER |
| N-(deoxyguanosin-C8-yl)-4-aminoquinoline-1-oxide | NER |
| 3-(deoxyadenosin-$N^6$-yl)-4-aminoquinoline-1-oxide | NER |
| Methylphosphotriester (DNA backbone modification) | ? |
| $O^6$-ethylguanine | DR, NER, MMR |
| ethanoadenine | BER |
| 1,2-ethenoguanine | ? |
| 2,3-ethenoguanine | ? |
| T opposite $O^6$-methylguanine | BER |
| A opposite 8-oxo-G | BER |
| Double strand breaks with variable overhangs and homologies | NHEJ, MMEJ, HR |
| Additional isomers of cyclobutane pyrimidine dimers and (6-4) photoproducts | NER |
| Protein DNA adducts | NER, ? |
| All permutations of mismatches | MMR |
| DNA lesions in the non-transcribed strand | Various (mixed lesions) |
| Normal bases opposite lesions | Various (mixed lesions) |
| DNA incubated with temozolomide | Various (mixed lesions) |
| DNA incubated with other chemotherapeutic drugs | Various (mixed lesions) |
| DNA treated with ionizing radiation | Various (mixed lesions) |

Processing

In one aspect, the disclosure provides methods of determining DNA repair capacity in a cell. In some embodiments, the disclosure provides methods of determining DNA repair capacity in a cell, the method comprising introducing one or more DNA repair vectors into a cell, and determining the capacity of the cell to process the one or more DNA repair vectors thereby determining the DNA repair capacity of the cell.

In some embodiments, processing the one or more DNA repair reporter vectors comprises modifying a DNA lesion present in the one or more DNA repair reporter vectors. In some embodiments, processing is detected by a change in a fluorescence signal. In some embodiments, processing is detected by a change in the transcribed sequence of the one or more DNA repair reporter vectors. In some embodiments, processing is detected by a change in the amount of transcribed sequence of the one or more DNA repair reporter vectors.

In some embodiments, the DNA repair pathway that processes the lesion is nucleotide excision repair, homologous recombination, non-homologous end joining, microhomology mediated end joining, direct reversal, base excision repair, mismatch repair or interstrand crosslink repair.

In some embodiments, the lesions that are processed comprise DNA-crosslinks. In some embodiments, the lesions that are processed comprise DNA alkylation damage. In some embodiments, the lesions that are processed block transcription. In some embodiments, the lesions that are processed induce transcription errors.

DNA repair enzymes process DNA lesions, which results in the removal or modification of the lesion. However, in some instances the lesions are not repaired before they are encountered by a DNA or RNA polymerase. One of three scenarios occurs when a polymerase runs into damage. In a first scenario the polymerase is not hindered by the lesions and continues transcription or replication and inserts the correct ribonucleotide or deoxyribonucleotide in the growing nucleic acid chain. In a second scenario, the polymerase is blocked from proceeding further, resulting in the stalling of either transcription (in case of an RNA polymerase) or replication (in case of a DNA polymerase). In a third scenario, the polymerase is not stalled by the lesion but incorporates an incorrect ribonucleotide or deoxyribonucleotide resulting in mutations. Lesions that result in DNA mutations and transcriptional mutagenesis are described for instance in Bregeon et al. (Nature Reviews Cancer 11, 2011, p 218).

In some embodiments, the disclosure provides methods of determining DNA repair capacity in a cell, the method comprising introducing one or more DNA repair reporter vectors into a cell, and determining the capacity of the cell to process the one or more DNA repair reporter vectors thereby determining the DNA repair capacity of the cell. In some embodiments, the processing is detected by the change in signal of a reporter gene. Thus, in some embodiments, the DNA repair reporter vectors that are introduced in the cell comprise a lesion and reporter gene. If the lesion does not block transcription the reporter gene is transcribed resulting in expression of the reporter gene. In some embodiments, the reporter gene encodes a non-fluorescent protein, and the propensity of a DNA lesion to induce transcriptional mutagenesis is detected as an increase in fluorescent signal. If the cell is able to repair the DNA lesion, a decrease in this fluorescence is observed. If the lesion blocks transcription or slows down transcription the amount of expressed reporter gene is reduced. In some embodiments, the reporter gene is a fluorescent protein and the propensity of a lesion to bock transcription can be assessed by a decrease in fluorescence signal. Examples of lesions that the change the signal of fluorescent reporter gene after processing of the DNA repair reporter vectors by the cell are provides in Table D. The lesions that lead to a change is reporter signal are presumed to partly or completely block transcription

TABLE D

Change in fluorescence of selected lesions

| Lesion | Main Repair Pathways | Changes in Fluorescence |
|---|---|---|
| Cys-Syn Thymine-Thymine cyclobutane pyrimidine dimer | NER | Yes |
| Double strand break | HR, NHEJ, MMEJ | Yes |
| Single strand break | BER | No |
| Base mismatches | MMR, BER | Yes |
| Single base insertion loops | MMR | Yes |
| $O^6$-methylguanine | DR, NER, MMR | Yes |
| $1,N^6$-ethenoadenine | BER, DR | No |
| $3,N^4$-ethenocytosine | BER, DR | No |
| cisplatin adducts | Cross-link repair, NER, HR | Yes |
| abasic sites | BER | Yes |
| UV irradiation (Cyclobutane Pyrimidine Dimers and (6-4) photoproducts) | NER | Yes |
| Incubation with MNNG (methylated bases) | BER, DR | Yes |
| Incubation with Chloroacetaldehyde (etheno bases) | BER, DR | Yes |
| Incubation with psoralen + UVA irradiation | Cross-link repair, HR, NER | Yes |
| Incubation with BCNU | Cross-link repair, HR, NER | Yes |

In some embodiments, the disclosure provides methods of determining DNA repair capacity in a cell, the method comprising introducing one or more DNA repair reporter vectors into a cell, and determining the capacity of the cell to process the one or more DNA repair reporter vectors thereby determining the DNA repair capacity of the cell. In some embodiments, the processing is detected by sequencing part or all of the transcripts produced from the DNA repair reporter vectors. Sequencing the transcripts allows for the determination if an incorrect nucleotide is inserted when RNA polymerase bypasses the lesion. Ribonucleotide sequences may be translated into deoxynucleotide sequences to facilitate sequencing.

DNA Repair Reporter Vectors

In some embodiments, the disclosure provides methods of determining DNA repair capacity in a cell, the method comprising introducing one or more DNA repair reporter vectors into a cell, and determining the capacity of the cell to process the one or more DNA repair reporter vectors thereby determining the DNA repair capacity of the cell. DNA repair reporter vectors comprise one or more lesions and a means for determining if the lesion has been processed. In some embodiments, the means for determining if a lesion has been processed is expression of a fluorescent reporter gene. In some embodiments, the fluorescent reporter gene is a green fluorescent protein. The placement of the lesion and the gene on the vector should be such that the blocking of transcription would prevent the gene from being expressed. In some embodiments, the lesion is in the reporter gene. In some embodiments, the lesion is located directly upstream of the reporter gene.

It should be appreciated that a reporter gene can also be used to evaluate the mutational aspect of the repair of the DNA lesion. For instance, a mutation can be introduced opposite a lesion in a reporter gene (e.g., a fluorescent gene) that inactivates the fluorescent ability of the protein. If a lesion is acted on, a new mutation may be introduced into the reporter gene restoring its ability to "report" (e.g., show a fluorescent signal).

The lesion can be introduced into the vector through any means. In some embodiments, the lesion is introduced through site specific engineering of a vector (See e.g., Shrivastav et al., Carcinogenesis 31, 2010, p 59). The site specific engineering allows for the introduction of a lesion at any desired position in the DNA repair reporter vector. In some embodiments, multiple site specific lesions are incorporated in the vector (e.g., 2, 3, 4, 5, 6, 7, 8, 9, 10 lesions or more). If more than one lesion is incorporated they can be the same lesion or different lesions (e.g., both $O^6$-methyl guanine or $O^6$-methylguanine and $N^7$-methylguanine). In some embodiments, multiple lesions that are representative for a particular environmental condition or cancer chemotherapy regimen are introduced into the vector. In some embodiments, multiple lesions that are susceptible to processing by the same DNA repair pathway are introduced into the same vector. In some embodiments lesions are introduced by treating the vector with a DNA damaging agent (e.g., UV light, cisplatin, or MNNG), resulting in a vector with a number of lesions corresponding to the damaging agent. In general, treating the vector with an increased dose and/or increasing the time of exposure will result in a higher number of lesions on the vector. It should be appreciated that some DNA damaging agents may induce more than one lesion (e.g., DNA alkylation agent will likely induce a number of different alkylated DNA lesions).

In one aspect, DNA repair reporter vectors comprise one or more lesions and means for determining if the lesion has been processed. In some embodiments, the means for determining if a lesion has been processed is a first nucleic acid sequence that can be sequenced. By sequencing a nucleic acid sequence at the site of the lesion or, in some instances, immediately upstream of the lesion, the presence of transcriptional mutations can be determined. Determining of the sequence allows for the determination of the lesion that has been processed by DNA repair. In some embodiments, the DNA repair reporter vector has both a reporter gene (e.g., a fluorescent gene) and a first nucleic acid sequence to be sequenced. By assaying both the amount of reporter gene and the sequence of the first nucleic acid, the DNA repair of the lesion can be evaluated both in the context of the blocking of transcription and the incorporation of mutations.

In some embodiments, the DNA repair reporter gene also comprises a second nucleic acid sequence (or additional nucleic acid sequences). The second (or additional) nucleic acid sequences allow for the coding of the DNA reporter repair vector. For instance, the second (or additional) nucleic acid sequences can code for the lesion that was introduced on the vector and/or the cell-line into which the vector was introduced, and/or the subject from whom the cell originated and/or the particular experiment or experimental condition.

In some embodiments, the DNA repair reporter vector comprises an origin allowing for replication of the vector inside the cell. Having an origin on the vector allows for the study of DNA repair in the context of replication.

In one aspect, the disclosure provides DNA repair reporter vectors for the methods, compositions, and kits for determining DNA repair capacity in a cell. In some embodiments, the DNA repair reporter vector comprises a DNA lesion and a fluorescence reporter gene. In some embodiments, the DNA repair reporter vector comprises a DNA lesion and a first nucleic acid sequence allowing for the identification of the DNA lesion. In some embodiments, the DNA repair reporter vector comprises a DNA lesion and a first nucleic acid sequence allowing for the identification of the DNA lesion and a fluorescence reporter gene. In some embodiments, the DNA repair reporter vector further comprises a second nucleic acid sequence allowing for the identification of the DNA repair reporter vector. In some embodiments, the first nucleic acid sequence allows for the determination of the processing of the DNA lesion. In some embodiments, the processing is detected by a change in the transcribed sequence of the nucleic acid sequence. In some embodiments, the processing is detected by a change in the amount of transcribed sequence of the nucleic acid sequence.

In some embodiments, the DNA repair reporter vectors comprise a DNA lesion that is susceptible to processing by nucleotide excision repair, homologous recombination, non-homologous end joining, microhomology mediated end joining, direct reversal, base excision repair, mismatch repair or interstrand crosslink repair. In some embodiments, the DNA repair reporter vector comprises a DNA lesion that is representative of a cancer treatment regimen. In some embodiments, the DNA repair reporter vector comprises a DNA lesion that is representative of an environmental condition.

A DNA repair reporter vector as used herein refers to a nucleic acid vector that can be introduced into a cell to determine the DNA repair capacity of the cell. As used herein, a "vector" may be any of a number of nucleic acids into which a desired sequence may be inserted. Vectors are typically composed of DNA. Vectors include, but are not limited to, plasmids. A desired DNA sequence, such as a reporter gene, may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells. The DNA repair reporter vector may be introduced into an appropriate host cell by any of a variety of suitable means, e.g., transformation, transfection, conjugation, protoplast fusion, electroporation, calcium phosphate-precipitation, direct microinjection, and the like.

Multiplexing

In one aspect, the disclosure provides methods, compositions and kits for determining the activity of multiple DNA repair pathways in multiple cells or subjects in one assay. Prior to the instant disclosure it was not possible to adequately determine the activity of multiple DNA repair pathways. Prior to the instant disclosure it was not possible to adequately determine the activity of multiple DNA repair pathways in multiple cells or subjects. In some embodiments, the multiple DNA repair reporter vectors comprise lesions susceptible to processing by nucleotide excision repair, homologous recombination, non-homologous end joining, microhomology mediated end joining, direct reversal, base excision repair, mismatch repair or interstrand crosslink repair.

In one aspect, the disclosure provides a method of determining multiple DNA repair capacities in a cell, the method comprising introducing multiple DNA repair reporter vectors into a cell, and determining the capacity of the cell to process the multiple DNA repair reporter vectors thereby determining multiple DNA repair capacities in the cell. In some embodiments, the multiple DNA repair reporter vectors comprises at least two, at least three, at least four, at least five, at least six, at least seven, at least eight, at least nine, at least ten or more DNA repair reporter vectors. In some embodiments, the multiple DNA repair reporter vectors comprise at least two DNA repair reporter vectors. In some embodiments, the multiple DNA repair reporter vectors comprises at least four DNA repair reporter vectors.

In some embodiments, if multiple DNA repair reporter vectors are introduced into a cell, they will each have a unique identifier. Thus, for instance, each DNA repair reporter vector may have a different fluorescent vector (Such as DsRed, EGFP, EYFP, SCFP, EBDP). Alternatively, or in addition, each DNA repair reporter vector may have a unique nucleic acid sequence to identify the DNA repair reporter vector (e.g., by sequencing).

In some embodiments, each DNA repair reporter vector of the multiple DNA repair reporter vectors comprises a unique DNA lesion. In some embodiments, the multiple unique DNA lesions are representative of a specific cancer treatment regimen. Thus, for instance, multiple unique lesions caused by an alkylating agent can be introduced is a cell to assess the ability of the cell to repair such lesions. In some embodiments, the multiple unique DNA lesions are representative of a multiple cancer treatment regimen. Thus, for instance, DNA repair reporter vector with lesions representative of alkylating agent therapy, cisplatin therapy and radiation therapy can be introduce in a cell to evaluate how the cell would respond to these different cancer treatment regimens.

In some embodiments each DNA repair reporter vector of the multiple DNA repair reporter vectors comprises a specific number of DNA lesions. In some embodiments, it may be desired to know how a cell line would responds with increasing doses of DNA damaging agents, such as in the case of cancer chemotherapy. Dose responses can be evaluated by assessing multiple DNA repair reporter vectors comprising a specific number of DNA lesions. Different number of lesions can be introduced in the vector, for instance, by exposing the vector to a DNA damaging agent for different amounts of time. In some embodiments, each DNA repair reporter vector of the multiple DNA repair reporter vectors comprises a number of DNA lesions corresponding to a specific dose of damaging agent. In some embodiments, each DNA repair reporter vector of the multiple DNA repair reporter vectors comprises a unique identifier.

Kits

In one aspect, the disclosure provides kits for determining the DNA repair capacity in a cell or multiple cells. In some embodiments, the kit comprises one or more DNA repair reporter vectors and instructions for use of the one or more DNA repair reporter vectors. Instructions for use in the kits include instructions for any aspect of the methods described herein, such as transfection of the plasmids into the cells, reporter assays and sequencing of the DNA repair reporter transcripts. In some embodiments, the kit comprises at least two, at least three, at least four, at least five, at least six, at least seven, at least eight, at least nine, at least ten or more DNA repair reporter vectors. In some embodiments, the kit comprises at least two DNA repair reporter vectors. In some embodiments, the kit comprises at least four DNA repair reporter vectors. In some embodiments, each DNA repair reporter vector of the kit comprises a unique DNA lesion. In some embodiments, each DNA repair reporter vector of the kit comprises a unique number of DNA lesions. In some embodiments, each DNA repair reporter vector of the kit comprises lesions susceptible to processing by nucleotide excision repair, homologous recombination, non-homologous end joining, microhomology mediated end joining, direct reversal, base excision repair, mismatch repair or interstrand crosslink repair.

In one aspect, the disclosure provides kits for determining the DNA repair capacity of a particular DNA repair pathway in a cell or multiple cells. In some embodiments, the DNA repair pathway is nucleotide excision repair, homologous recombination, non-homologous end joining, microhomology mediated end joining, direct reversal, base excision repair, mismatch repair or interstrand crosslink repair.

In one aspect, the disclosure provides kits for determining the propensity of a subject to respond to a cancer treatment regimen comprising one or more DNA repair reporter vectors, wherein the one or more DNA repair reporter vectors comprise lesions representative of a cancer treatment regimen, and instructions for use of the one or more DNA repair reporter vectors.

In one aspect, the disclosure provides kits for determining the susceptibility of a subject to an environmental condition comprising one or more DNA repair reporter vectors, wherein the one or more DNA repair reporter vectors comprise lesions representative of an environmental condition, and instructions for use of the one or more DNA repair reporter vectors.

In one aspect, the disclosure provides kits for determining the repair capacity of a cell line comprising one or more DNA repair reporter vectors, wherein the one or more DNA repair reporter vectors allow for the determination of the repair capacity of the cell line, and instructions for use of the one or more DNA repair reporter vectors.

In some embodiments, the kit further comprises a cell line with a known DNA repair capacity. The kit may also include additional components, such as vials, solutions, buffers, plates, and reagents to perform the methods disclosed herein.

In one aspect, the kits allow for a high throughput, comprehensive, and quantitative assessment of the capacity of cells to repair DNA damage via a large number pathways in a single assay. DNA repair capacity varies among individuals, and deficiencies are associated with a large number of diseases. The kits serve as a diagnostic for such deficiencies. Sensitivity to DNA damaging agents (including chemotherapeutic and other drugs, sunlight, ionizing radiation, cigarette smoke, as well as endogenous sources of DNA damage) varies significantly among healthy individuals. These differences are, at least in part, a consequence of inter-individual differences in DNA repair capacity. The kit also provides a means of offering personalized disease prevention to individual patients with particular DNA repair deficiencies or abnormalities. In addition, the kit can be used to optimize treatment of known diseases. For example, an ideal chemotherapy could be tailored to an individual patient based on differences in the DNA repair capacity of the cancer patient's healthy normal tissues, as compared with that of the tumor.

Figure 15:
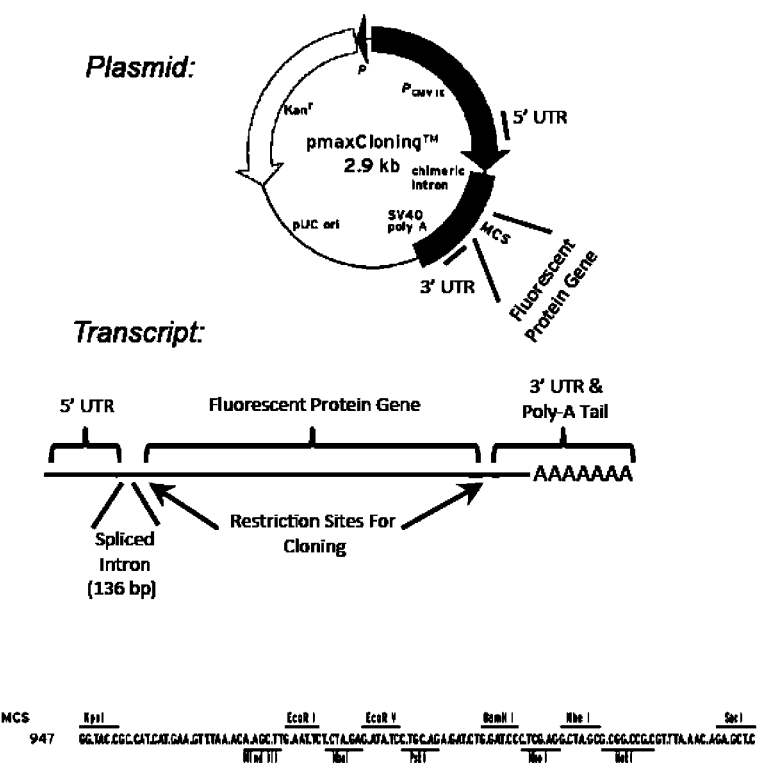
FIG. 15 is a sequence (SEQ ID NO:3) showing the construction of reporter constructs.

In some embodiments, measurements of DNA repair capacity are based on the transient transfection of cells with a library of plasmid DNA reporters containing different types or doses of DNA damage. An embodiment of a DNA repair reporter vector is provided in FIG. 15.

Detection of reporters is achieved by a number of methods. In a first method of detection, repair capacity is measured in intact cells via fluorescence-based host cell reactivation technology, wherein repair of transcription blocking DNA damage results in measurable reactivation of otherwise inhibited fluorescent protein expression. Fluorescence in two or more channels is measured, for instance, by flow cytometry, or laser scanning cytometry. Each fluorescent reporter color corresponds to repair of a different DNA lesion, or a different dose of DNA damage. One fluorescent reporter is used as a transfection control. A fluorescent viability stain can be used to exclude dead cells, or a fluorescent nuclear stain can be used to analyze repair in a cell cycle dependent manner. An example of how the "Lumens" technology can be applied to human cells is illustrated in FIGS. 16-19).

The given method of measuring DNA repair capacity combines the efficiency of high throughput transfection with the speed, sensitivity, and multiplexing capability of flow cytometric analysis to yield a rapid, high throughput, multiplexed host cell reactivation assay.

Figure 14:
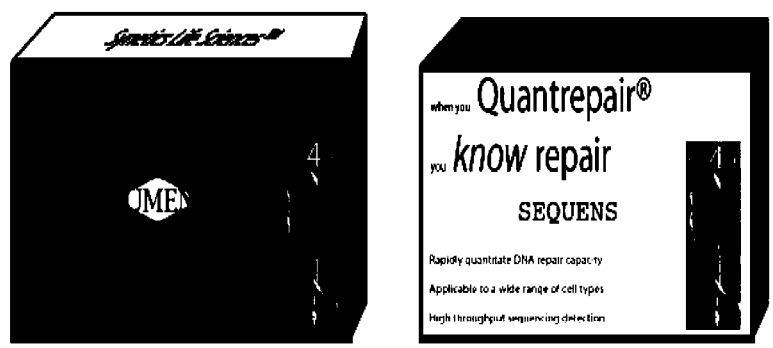
FIG. 14 is a drawing showing embodiments of kits for DNA repair capacity measurements. One kit uses reporters with fluorescence based detection (Lumens) and one kit uses next generation sequencing based detection (Sequens).

In a second method of detection instead of measuring fluorescent translation products of transcription reporters, mRNA transcripts themselves are measured and analyzed. (A kit according this technology is called "Sequens" in FIG. 14. The two methods are complimentary, with each having unique advantages (Table E).

TABLE E comparison of fluorescent and sequencing methods

| | Flourescence | Sequencing |
|---|---|---|
| Advantages | Straight-forward procedure (electroporation, plasmid preparation) and analysis<br>Single-cell resolution<br>Binary Results<br>Inexpensive | Can 'count' relative numbers of flourescent protein transcripts<br>Data on transcription errors/deletions/frameshift mutations<br>Applicable to most DNA lesions<br>Can compare results to FACS data |

TABLE E-continued comparison of fluorescent and sequencing methods

| | Flourescence | Sequencing |
|---|---|---|
| Disadvantages | Not all damage inhibits RNA polymerase<br>Lose information about transcription errors<br>(deletions, RNA base misincorporation,<br>frameshifts) and aborted or improperly-folded<br>transcripts | No single-cell resolution<br>Longer sample preparation without immediate results<br>More expensive<br>Works better with site-specific lesions<br>Potentially more difficult data analysis |

An experiment analogous to that described for fluorescent reporters above includes reporter transcription measured directly by counting transcripts produced when cells are transfected with either damaged or undamaged plasmids. Direct detection of transcripts provides additional information on the DNA repair capacity of the cell or subject. Whereas the optical properties of fluorescent reporters currently limit the number that can be simultaneously and independently detected to 5 or 6, thousands of unique reporter transcripts (or more) can be measured simultaneously using high throughput DNA sequencing. A sequencing based assay for DNA repair capacity is provided in FIGS. 20 and 21 (See also Table F).

TABLE F

Sequencing HCR.

| Sample cDNA | Number of Colonies Sequenced | Number of EGFP Colonies | Number of RFP Colonies |
|---|---|---|---|
| RFP Undamaged | 20 | 14 | 6 |
| RFP at 800 J/m2 | 12 | 11 | 1 |

In a low-throughput sequencing HCR, sequences from reporters damaged with UV radiation were represented less often among cDNA clones, consistent with reduced transcription relative to the undamaged controls. Next generation sequencing of the same materials provides the statistical power needed to resolve differences in repair capacity.

Although sequencing based repair assays can in principle be approached using randomly damaged plasmids, knowing the exact location of the lesions in advance greatly increases signal to noise and focuses the analysis to a short region of the reporter gene. An example of how site specifically introduced lesions are applied in a DNA repair assay is given in FIG. 23, and the methodology developing for the production of the necessary reporters is presented in FIG. 24.

In one aspect, the sequencing based DNA repair capacity kit provides a new technology (FIGS. 20-26) for a new method for measuring DNA repair capacity. In some embodiments, a library of site-specific reporters in close proximity to the identifying bar code that corresponds to each respective DNA lesion is provided. This proximity is constrained by the maximum read length of the high throughput sequencing equipment, currently about 150 nucleotides on most instruments. The scope of the substrates in the Sequens kit is described in FIG. 27.

Existing technology restricts measurements of DNA repair capacity to a single type of DNA damage in each assay. The most direct comparisons can be made to HCR assays that are done with chloramphenicol acetyltransferase reporters. However CAT based assays require cell lysis, several hours of manual sample processing, one-at-a-time, involve radioactive tracers, and there is no way to control for transfection efficiency. Luciferase has also been used as a reporter in HCR assays, however this method is limited to only two colors, and also requires cell lysis. Fluorescent reporters have been described in a few papers in the literature, however only two colors at a time have been used, and no rigorous method of detection with appropriate controls and careful calibration against previously characterized methods has been reported. The examples in the literature also do not describe methods of scaling up the procedure for high throughput 96-well formats. The kits provided herein enable repair of at least 4 (Lumens) and up to 100s or even 1000s or more (Sequens) types of damage or doses of damage to be assayed simultaneously. The use of next generation sequencing to detect reporter transcripts as reporters for DNA repair capacity has not been previously reported. Site specific DNA damage has not been used in a massively parallel analysis as provided herein. Previous methods generally require samples to be handled and analyzed one at a time, whereas the methods provided herein enable one to assay multiple samples simultaneously and automatically using robotics (in the case of flow cytometry) or bar codes and software (for sequencing based detection). Previous methods make use of variable reporter constructs, readouts and methods of transfection, potentially confounding comparisons among experiments conducted in different laboratories. Rigorous controls for these confounding variables are generally not carried out. Inter-laboratory variability, together with the cumbersome standard approaches to measuring DNA repair capacity make them low throughput, and thus refractory to large scale epidemiological studies and clinical applications. The high-throughput kits provided herein establish rigorous controls for transfection efficiency, variability in reporter expression, and possible inter-laboratory variability (using a control cell line against which samples can be compared). A particular advantage of the sequencing-based detection system is the possibility of shipping nucleic acid samples to an off-site location for analysis by a third party; existing methods require the analysis of intact cells or fresh cell lysates. Previous methods also require significant background on the part of the user. The methods provided herein make DNA repair capacity measurements accessible to scientists with basic laboratory training. The Lumens kit provides a comprehensive spectrum of DNA repair capacity for any cell culture amenable to transient transfection in about 24 hours. Embodiments of kits of the invention are provided below QUANTREPAIR® "Lumens" (Cytometry Based Approach)
    A library of 5 or more undamaged fluorescent reporter encoding plasmids
    A library of 4 or more fluorescent reporter encoding plasmids that contain DNA lesions
    Buffers
    8 peak fluorescent beads to calibrate flow cytometers A control cell line against which to validate and compare results Data analysis templates A manual describing how to use the kit and analyze data QUANTREPAIR® "Sequens" (Sequencing Based Approach)

A library of 10 or more undamaged reporter plasmids

A library of 10 or more bar-coded reporter plasmids bearing site-specifically incorporated lesions Buffers Primers for cDNA synthesis and amplification A control cell line against which to validate and compare results Data analysis templates A manual describing how to use the kit and analyze data The kit may be provided either as a research tool or as a clinical test. In the research laboratory, the kit may provide a rapid and reliable way to measure DNA repair capacity/deficiency in previously uncharacterized cell lines. It may also be used in conjunction with previously uncharacterized types of DNA damage to determine whether they are repaired in cells. In the clinical setting, the assay may be used as a routine blood test for an individual's repair capacity spectrum, and the data used to advance personalized prevention and treatment of disease.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1: HT-HCR and HCR-Seq: High Throughput Tools for DNA Repair Capacity Measurements Materials and Methods
Human Cells A total of 19 human cell cultures representative of 12 individuals were obtained from the Coriell Institute (Table 1). Epstein Barr virus transformed lymphoblastoid cell lines were maintained in log phase in GIBCO RPMI 1640 supplemented with 15% fetal bovine serum (FBS), in the presence of 2 mM L-glutamine, penicillin and streptomycin. Primary skin fibroblasts were cultured in GIBCO DMEM/F12 media supplemented with 15% FBS and, in the presence of 2 mM L-glutamine and antibiotics. Fibroblasts were subcultured by trypsinization.

Plasmids

Plasmids containing genes encoding the fluorescent proteins AmCyan, EGFP, mOrange, and mPlum were purchased from Clontech, and a plasmid encoding tagBFP was purchased from Axxora. Reporter genes were subcloned into the pmax cloning vector (Lonza) between the KpnI and SacI restriction sites in the multiple cloning site. The Kozak translation initiation consensus sequence and an additional NheI restriction site were introduced at the 5' end of each reporter, and a HindIII restriction site was added to the 3' end. The pmax cloning vector places reporter genes under a CMV Intermediate-Early promoter. Plasmids were amplified using *E. coli* DH5-alpha, and purified using Qiagen endotoxin-free giga kits. Constructs were confirmed by DNA sequencing and restriction digests.

UV-Irradiation

Plasmids were irradiated at a concentration of 50 ng/uL in a volume of 1.5 mL in 10 cm polystyrene petri dishes (without lids) with UVC light generated by a STRATA-LINKER® 2000 box. Following treatment, reporter plasmids were combined in the following ratio: 1 part tagBFP, 10 parts AmCyan, 1 part GFP, 2 parts mOrange, and 4 parts mPlum. Increased amounts were used to compensate for the weaker fluorescence intensities observed for some of the reporters. Corresponding mixtures of plasmids without UV irradiation were prepared from the same solutions, except without treatment. Although experiments performed with the mixture containing irradiated plasmids have been labeled "damaged", and those containing untreated plasmids have been labeled "undamaged", every transfection included a transfection reporter, which always remained undamaged. The transfection reporter was used to normalize for potential variation in transfection efficiency. Further details regarding the dose delivered to each plasmid are available in Table 2. Plasmid mixtures were ethanol precipitated, and washed with 70% ethanol. Pellets were dissolved in TE buffer for 30 minutes at room temperature, to a final concentration of approximately 1.5 micrograms per microliter. The damaged and undamaged solutions were adjusted to the same final concentration. DNA concentrations were verified using a Nanodrop spectrophotometer.

Transfection

Lymphoblastoid cells at a concentration of $2 \times 10^7$/mL (total volume, 100 uL) in complete media were combined with 9 micrograms of reporter plasmid mixtures using the cocktails described above. The mixtures were electroporated using a Bio-rad MXCELL™ gene pulser, with an exponential waveform at 260V and 950 uF. Following electroporation, cells were diluted 5-fold in fresh culture media, and divided into three 96-well plates. Cells were incubated at 37° C., 5% $CO_2$, and one plate was removed for analysis at each time point (18 and 40 hours). The third plate was reserved as a backup. Each transfection was performed in duplicate, on three separate days. The same procedures were used for the samples that were analyzed by sequencing, however each transfection was performed in quadruplicate, the quadruplicate transfections were diluted into a single 2 mL culture.

Flow Cytometry

Live cells suspended in culture media were analyzed for fluorescence on a BD LSRII cytometer, running FAC-SDIVA™ software. Cell debris, doublets and aggregates were excluded based on their side scatter and forward scatter properties. TOPRO®-3 was added to cells 5-10 minutes prior to analysis, and used to exclude dead cells from the analysis. The following fluorophores and their corresponding detectors (parentheses) were used: tagBFP (Pacific Blue), AmCyan (AmCyan), EGFP (FITC), mOrange (PE), mPlum (PE-Cy5-5), and TOPRO-3 (APC). The linear range for the corresponding photomultiplier tubes was determined using BD Rainbow fluorescent beads and unlabeled polystyrene beads based on the signal to noise ratio, % CV, and M1/M2 parameters as previously described (REF). Compensation was set using single color controls. Regions corresponding to cells positive for each of the 5 fluorescent proteins were established using single color dropout controls.

Fluorescence signal (F) was computed using equation 1:

$$F = \frac{N \times MFI}{S} \quad (1)$$

Where N is the total number of cells appearing in the positive region for that fluorophore, MFI is the mean fluorescence intensity of the N cells, and S is the total number of live cells measured in the experiment. The fluorescence signal of an undamaged plasmid included in all transfections to control for transfection efficiency was designated $F^E$. The normalized fluorescence signal for a given reporter $F^O$ was calculated using equation 2:

$$F^O = \frac{F}{F^E} \qquad (2)$$

Normalized reporter expression from a damaged reporter plasmid, $F^O_{dam}$, and that from the same reporter plasmid in the absence of damage, $F^O_{un}$, were used to compute the percent reporter expression (% R.E.) using equation 3:

$$\% \ R.E. = \frac{F^O_{dam}}{F^O_{un}} \qquad (3)$$

Preparation of Plasmids Containing a Site-Specific Thymine Dimer

A site-specific thymine dimer was introduced into the GFP reporter plasmid using methods described previously [21]. Briefly, two nicking sites for the enzyme Nb.Bpu10I in the GFP reporter gene near the 3' end were used to excise a single stranded oligonucleotide of 18 bp in length: 5'-TCA-GGGCGGATTGGGTGC-3' (SEQ ID NO: 6). The nicking sites flank a silent mutation that has been introduced to generate a TpT sequence in the transcribed strand of the plasmid. A synthetic oligonucleotide 5'-TCA-GGGCGGAT<>TGGGTGC-3' (SEQ ID NO: 7), containing a thymine-thymine cis-syn cyclobutane dimer (indicated by T<>T) and synthesized by TriLink BioTechnologies using a cis-syn thymine dimer phosphoramidite (Glenn Research) was ligated into the gapped plasmid. The incorporation of the site-specific thymine dimer in the plasmid was confirmed by an endonucleolytic digest with the bifunctional enzyme thymine dimer specific glycosylase/AP lyase (T4 PDG).

Isolation of Total RNA for RNAseq

At 18 hours, transfected cells were harvested by centrifugation, washed three times with fresh media, and resuspended in 1 mL TRIZOL® reagent. The suspension was extracted with 200 µL chloroform. The aqueous phase was removed, combined with one volume of absolute ethanol, and applied to a Qiagen RNEASY® mini-prep spin column. The column was then washed two times with 500 µL buffer RPE (Qiagen), and finally eluted in 40 µL diethylpyrocarbonate (DEPC) treated water. From this point forward, RNA was handled in Eppendorf DNA LoBind tubes to minimize loss of material. The quality of the RNA preparation was determined using a bioanalyzer to confirm a RIN of at least 9.0. 1 µg of total RNA was stored in TE Buffer at −80° C. until submission for RNAseq.

Isolation of mRNA and Synthesis of cDNA

From the remaining total RNA, mRNA was isolated using a Qiagen Oligotex kit, using the manufacturer's protocol, but substituting Eppendorf DNA LoBind tubes for those provided with the kit. In the final step, mRNA was eluted in 20 uL buffer OEB preheated to 70° C. 5 µL of the eluate was transferred to a LoBind tube, combined with 1 µL of DNAse buffer and 1 unit of DNAseI (Invitrogen). The mixture was brought up to a 10 µL volume with DEPC treated water, and incubated for 15 minutes at room temperature. DNAse was inactivated by addition of 1 µL of 25 mM EDTA, followed by incubation at 65° C. for 10 minutes. A cocktail comprised of 2×RT buffer (Qiagen), oligo-dT(12-18) (125 ng/uL; invitrogen), 4 units of RNAse inhibitor (Qiagen), 5 mM dNTPs, and 4 units of reverse transcriptase (Omniscript; Qiagen) was prepared, and 8 µL added to the DNAse digest. The reaction was incubated for 1 hour at 37° C. No-RT controls were performed identically, except for the exclusion of the reverse transcriptase.

Specific Amplification of Reporter cDNA by PCR cDNA samples were amplified with primers specific to the 3' and 5' UTR regions of the pMax vector. The following primers were synthesized for specific amplification of reporter cDNA:

```
                                       (SEQ ID NO: 1)
5UTR:   5'-TTG CTA ACG CAG TCA GTG CT-3'

(SEQ ID NO: 2)
3UTR:   5'-GCA TTC TAG TTG TGG TTT GTC C-3'
```

1.5 µL of cDNA was PCR amplified in a 25 µL reaction volume with 1×PCR buffer (Denville), 0.5 µM primers, 0.2 mM dNTPs, and 1 unit Taq polymerase (Denville). Specific amplification was confirmed by gel electrophoresis and analysis on a bioanalyzer chip. Water and EGFP encoded plasmids were used as negative and positive controls, respectively. Finally, reactions were cleaned up using a Qiagen PCR cleanup kit according to the manufacturer's protocol, and eluted in 50 uL of TE.

Fragmentation of DNA 250 ng of PCR product was diluted to a total volume of 130 uL in TE buffer. The DNA was fragmented in a Covaris microTUBE using a Covaris S2 sonicator (Duty Cycle 10%, Intensity 5, 200 cycles per burst, 180 seconds. Fragmentation to a target base pair peak of 150 bp was checked using a Agilent BioAnalyzer.

Next Generation Sequencing

Total RNA and fragmented DNA samples were submitted to the MIT biomicrocenter core facility for preparation and sequencing. Briefly, total RNA was poly-A purified and converted to cDNA DNA using the Illumina Tru-Seq protocol. Library construction from cDNA and fragmented DNA was performed using the Beckman Coulter SPRIworks system (REF). During library amplification, a unique bar-code was introduced for each of 8 samples corresponding to the four transfections (#1953 undam, #1953 dam, #2344 undam, #2344 dam), from which both total RNA and PCR amplified reporter cDNA were generated. Samples were clustered on a sequencing lane and run on an Illumina HISEQ™ 2000 instrument. Image analysis, base calling and sequence alignment to a synthetic genome consisting of the human genome and the five fluorescent reporter genes were performed using the Illumina Pipeline.

Next Generation Sequencing Data Analysis

Both RNAseq and DNAseq data were analyzed using the Tuxedo software suite. Reads were aligned to the human genome and the five reporter gene sequences, and junction reads determined. Additional details of all analyses including input parameters are available in supplemental Table S1. Cufflinks was run to quantify reads in terms reads per kilobase of exon model per million mapped reads (RPKM) [18]. Single nucleotide mutations, as well as insertions and deletions (indels) present in the RNAseq and DNAseq data were identified using the software package VarScan [19]. The software required a minimum read depth of 8, and at least 2 reads supporting a mutation at a given position. Variants were reported if they were detected in at least 1% of all reads covering a given position, or at least 2 unique reads after removal of duplicates. Variants appearing in the first 168 nucleotides were excluded from further analysis because this region includes the chimeric intron and the binding site of the 5' UTR primer. Likewise, the variants appearing in the terminal 22 nucleotides were excluded because this sequence derives from the 3' UTR primer. Variants observed at the position corresponding to the site-specific thymine dimer prompted a targeted search for similar variants in transcripts expressed from randomly damaged reporters. Scripts were used to generate a list of all deletions 6 bases or longer and spanning an ApA sequence, and appearing at a frequency of at least 0.01% of all reads. The global frequency of the most commonly observed base substitutions opposite the thymine dimer (5'A→G) and (3'A→T), as well as the dinucleotide mutation (AA→GT), was determined for all ApA sequences for each sample.

Results

Figure 8:
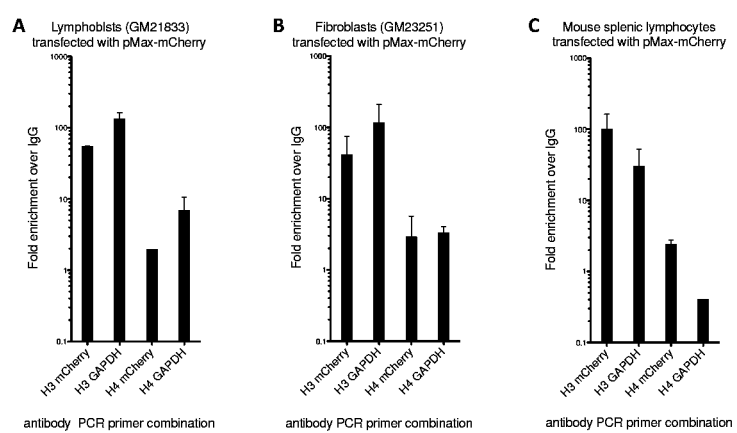
FIG. 8 shows chromatin immunoprecipitation from three types of cells transfected with pmax:mCherry A) lymphoblasts, B) fibroblasts, C) mouse splenic lymphocytes.

A high throughput multicolor host cell reactivation assay (HT-HCR) was successfully deployed in 19 cell lines from 12 individuals (Table 1). Because multiple cell types were studied from some individuals, Greek letters (α-η) have been assigned to refer to the individuals from whom the cells were derived. Electroporation yielded consistently high transfection efficiency ranging between 10 and 50% in all cells studied. Chromatin immunoprecipitation of DNA isolated from transfected cells using antibodies to histone H3 or H4 confirmed the chromatinization of reporter plasmids (FIG. 8). Expression levels of five fluorescent reporter proteins were quantitated simultaneously and independently using flow cytometry. In addition, a dead cell stain (TO-PRO®-3) was successfully used to exclude dead cells from flow cytometric analysis. Use of 96-well electroporation plates reduced the time required for transfection to less than one minute per sample, and use of a BD High Throughput Sampler permitted data acquisition in less than 10 minutes active time.

In vitro treatment of plasmids with UVC light resulted in a dose-dependent reduction in reporter expression. When each of the five fluorescent reporter plasmids was treated with a unique dose of UVC (Plasmid combination #1 in Table 2), and subsequently co-transfected into cells, a dose-response curve was generated from a single experiment that requires only two transfections (FIG. 1). Dose-response curves spanning up to 3 decades of percent reporter expression (% R.E.) were obtained for 7 lymphoblastoid cell lines (FIG. 2), chosen because they have been characterized for their capacity to repair UV-irradiated DNA previously by another method [8]. Two cell lines were derived from healthy individuals, and five from xeroderma pigmentosum patients with known genetic defects in the NER pathway (Table 1). Differences in repair capacity were most pronounced at the highest dose to plasmid (800 J/m$^2$), with % R.E. values varying over a range of about 100-fold among the cell lines. As expected, the highest repair capacity was observed for lymphoblastoid cell lines derived from apparently healthy individuals. Moderately reduced repair was observed for two XPC cell lines, and a severe defect was evident for XPA and XPD cell lines. Between 18 and 40 hours, % R.E. increased for most cell lines (FIG. 2), consistent with time-dependent repair of transcription blocking lesions.

Figure 2:
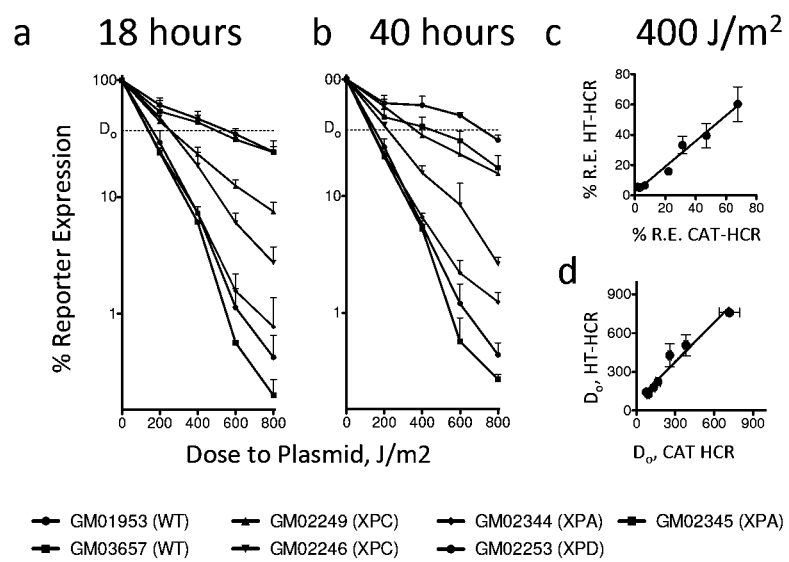
FIG. 2 shows the validation of HT-HCR against literature data. a) Dose-response curves for seven cell lines 18 hours after transfection with plasmid combination #1 (Table 2). Error bars represent the standard deviation calculated from biological triplicates. b) Dose response curves at 40 hours. c) Comparison of % reporter expression as measured by HT-HCR at 400 $J/m^2$ is plotted against % CAT as measured by conventional HCR for the same cell lines at 300 $J/m^2$. d) $D_o$ values calculated from HT-HCR data plotted against those reported in the literature.

The HT-HCR data presented in FIG. 2 reproduce those from literature [8]. In that study, chloramphenicol acetyl transferase (CAT) expression was used as the reporter. Two complementary methods were used to compare our data to those in the literature. First, the percent CAT expression (% CAT) reported at a single dose of UV irradiation (300 J/m$^2$ in the Athas et al. study) was found to be highly correlated with % R.E. at a single dose (400 J/m$^2$) in the present study ($R^2$=0.92, p=0.0006). The relative repair capacity of multiple cell lines has also been compared by calculating the parameter $D_o$, which corresponds to the dose at which the HCR dose response curve falls below 37% reporter expression [20]. $D_o$ was calculated from our experimental data and was also found to be highly correlated with the literature values ($R^2$=0.92, p<0.0001).

Figure 3:
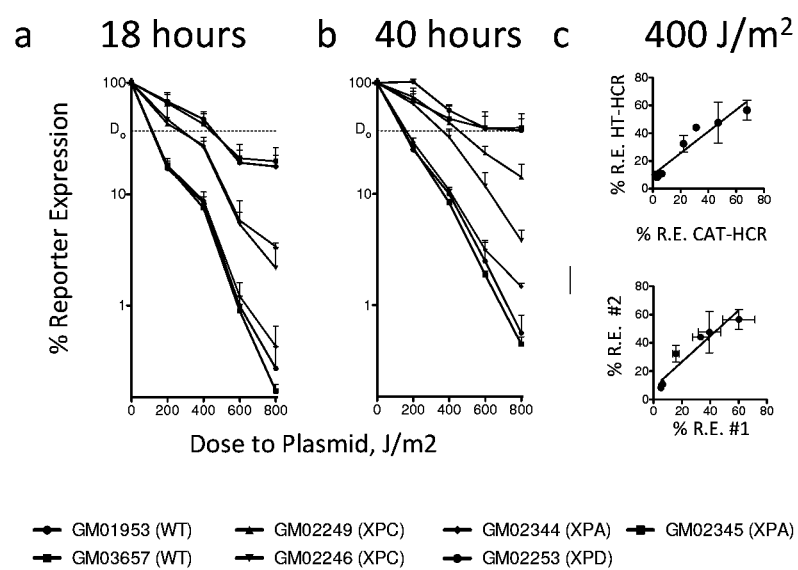
FIG. 3 shows the reproducibility of the HT-HCR. a) Dose-response curves for seven cell lines 18 hours after transfection with plasmid combination #2 (Table 2). b) Dose response curves at 18 hours. Error bars represent the standard deviation calculated from biological triplicates. c) Dose response curves at 40 hours. c) Comparison of % reporter expression as measured by HT-HCR at 400 $J/m^2$ is plotted against % CAT as measured by conventional HCR for the same cell lines at 300 $J/m^2$. d) Comparison of HT-HCR data for plasmids treated at 400 $J/m^2$ in experiments #1 and #2.

To confirm that the dose response curves in FIG. 2 could be obtained independent of the choice of fluorescent reporters, the experiment was repeated with the plasmids shuffled so that each received a different dose (Plasmid combination #2 in Table 2). The pattern of dose response curves and the relationship to the data in FIG. 2 are presented FIG. 3. Once again, repair capacity measured in % R.E. at the highest dose to plasmid (800 J/m$^2$) varied over a range of about 100-fold among the cell lines, and % R.E. increased between 18 and 40 hours (FIGS. 3a and 3b). Our assay again reproduces the literature data (FIG. 3c). Repair capacity measurements from the two combinations of reporter plasmids were highly correlated (FIG. 3d).

Figure 4:
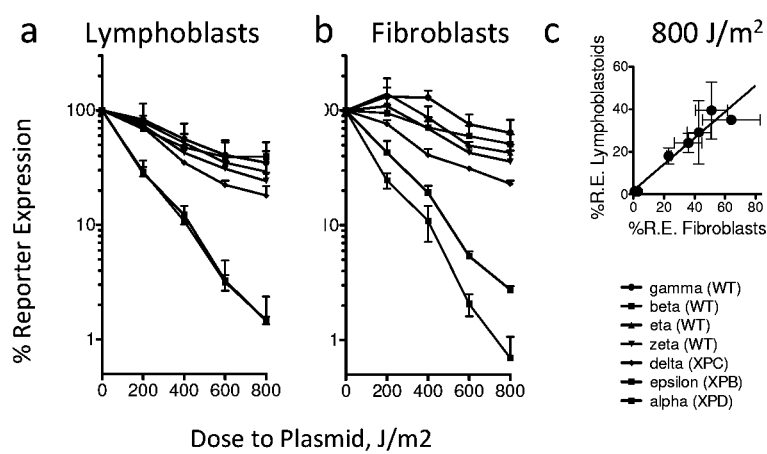
FIG. 4 shows measurements of DNA repair capacity in two cell types from each of seven individuals. a) Dose response curves generated by HT-HCR for lymphoblastoid cell lines 40 hours after transfection with plasmid combination #2 (Table 2). Error bars represent the standard deviation calculated from biological triplicates. b) Corresponding dose response curves for primary skin fibroblasts from the same seven individuals. c) Correlation between % reporter expression in the two cell types at 800 $J/m^2$.

HT-HCR assays were also carried out on 7 primary untransformed skin fibroblasts and Eppstein-Barr virus transformed lymphoblastoid cell lines derived from the same individuals (represented as α-η in Table 1). These experiments included cells from 4 apparently healthy individuals, and 3 XP patients. A similar pattern of dose response curves was obtained for both fibroblasts and lymphoblastoid cells (FIG. 4). Overall, absolute NER capacity measured in fibroblasts appeared to be somewhat higher than that in the lymphoblastoid cell lines, however the relative differences in repair capacity among individuals were largely preserved in the two cell types. Comparison of repair capacity measured at 800 J/m$^2$ indicated that NER phenotype is strongly correlated between the two cell types ($R^2$=0.94, p=0.0003).

Figure 5:
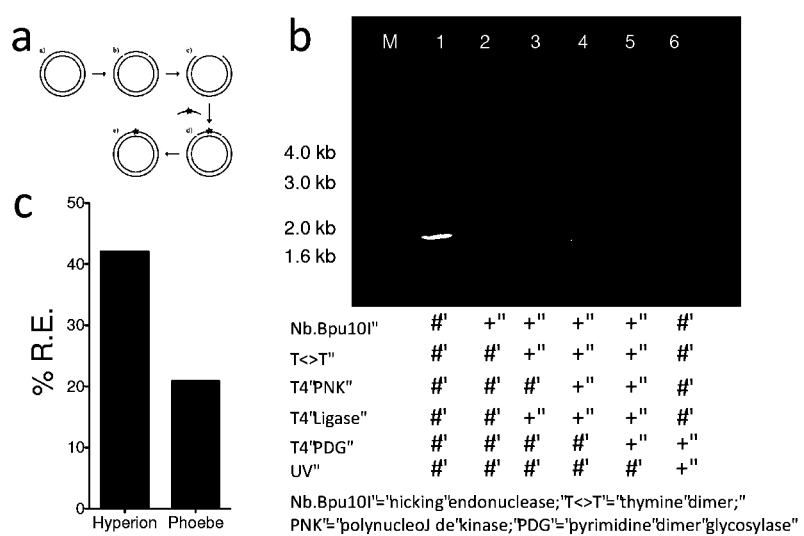
FIG. 5 shows the construction and validation of a plasmid containing a site-specific thymine dimer. a) A synthetic oligonucleotide bearing a site-specific thymine dimer is ligated into a gapped plasmid according to the methods of Kitsera et al. (a). b) Gel electrophoresis of synthetic intermediates and product (lanes 1-4) and assay for site specific or randomly introduced pyrimidine dimers in reporter plasmids (lanes 5-6). c) NER-dependent reduction in fluorescent reporter expression from plasmids containing the site-specific thymine dimer.

A site-specific thymine dimer spanning positions 614-615 of the GFP sequence was successfully introduced into transcribed strand of the pmax GFP reporter plasmid using previously described methods [21]. Most of the plasmids were nicked upon incubation with the bifunctional thymine dimer specific DNA glycosylase/AP lyase, T4 PDG (FIG. 5), indicating that nearly all of the material contained the lesion. Following transfection into cells, GFP expression from the lesion-containing plasmid was reduced relative to that from an undamaged reporter. As expected, the largest inhibition of reporter expression was observed in NER deficient cells.

Figure 11:
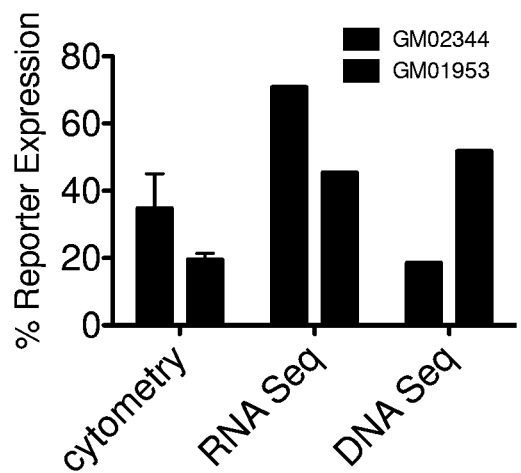
FIG. 11 shows expression of GFP from reporter plasmid containing a site specific thymine dimer in the transcribed strand, assayed by flow cytometry, RNAseq, or DNAseq. Error bars represent the standard deviation of two biological replicates

Two cell lines exhibiting a large difference in their NER capacity (GM02344 and GM01953) were selected for comparative repair capacity measurements by HT-HCR and HCRseq. The two cell lines were transfected with plasmid combination #3 in Table 2. An aliquot of cells was removed from the transfection at 18 hours for flow cytometric analysis, and the remaining cells were solubilized in Trizol reagent for subsequent analysis by HCRseq (see below). GFP expression from the thymine dimer containing reporter plasmid was successfully measured following co-transfection with additional reporter plasmids that had been randomly damaged with several doses of UV radiation (FIG. 11). The dose response curves generated from the randomly damaged plasmids are presented in FIG. 6b.

Figure 9:
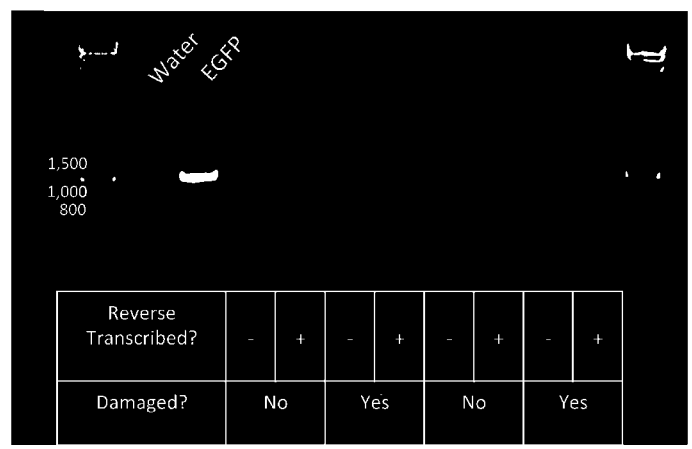
FIG. 9 shows gel electrophoresis of amplicons generated from reporter cDNAs by PCR.

For HCRseq analysis, total RNA was isolated from the aliquot of cells that was reserved in TRIZOL®. The quality of the RNA was checked using a bioanalyzer, and the RNA Integrity Number was found to be at least 9.0 for all samples. Two separate experiments were then performed. First, an aliquot of total RNA was submitted directly for RNAseq analysis. In the second experiment, reporter transcripts were enriched by selective PCR amplification. Because these samples were submitted as DNA, this experiment and the resulting data are referred to as "DNAseq". For the DNAseq experiment, total RNA was purified to mRNA and reverse transcribed. PCR amplification of cDNA using primers specific for the 5' and 3' UTR of the reporter genes generated the expected single ~800 bp amplicon (FIG. 9). PCR amplification was dependent upon reverse transcription, confirming that the mRNA was free from plasmid contamination. In both agarose gels and bioanalyzer traces, amplicons generated from cDNA templates were found to migrate slightly ahead of those generated from plasmid templates. This was expected based on the presence of a 136 bp chimeric intron present in the reporter plasmid, and provides further confirmation that mRNA was isolated without plasmid contamination. Sonication successfully fragmented PCR amplicons to a peak size of approximately 150 bp, as recommended for Illumina TruSeq sample processing.

A total of 180,216,333 reads were generated for 8 multiplexed samples in a single HISEQ™ lane (Table 3). Using the barcode sequences that were introduced during sample prep, 92,111,949 (51.1%) of the reads were assigned to the four samples (A, B, C and D) from the RNAseq experiment, and 88,104,384 (48.9%) were assigned to the DNAseq experiment (E, F, G, and H). Between 15 and 25 million reads were assigned to each of the 8 samples. Additional alignment statistics are available in supplemental Tables S2-S5.

Figure 10:
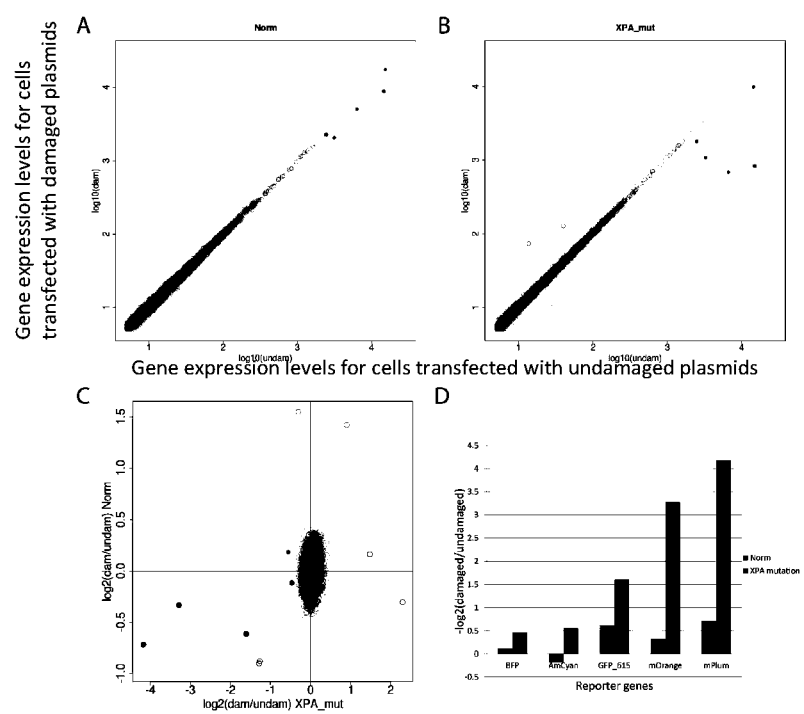
FIG. 10 shows genes expression profile of cells transfected with damaged or undamaged reporter plasmids. In panels A and B, levels of expression are plotted for all transcripts. Levels of expression in cells that were transfected with damaged plasmids are plotted on the vertical axis, and expression levels in cells transfected with the undamaged (control) plasmids are plotted on the horizontal. Genes expressed at the same level under both conditions appear on the diagonal, and this is overwhelmingly the case for endogenous transcripts (black and gray circles), indicating no major changes in transcription in cells in response to the presence of damaged plasmid DNA. Reporter transcripts are colored in blue, cyan, orange, green, and magenta. These reporters are seen to be among the most highly expressed in all samples. Reduced expression in the presence of DNA damage (due to transcription blocking lesions) is reflected in these points falling below the diagonal

Relative expression levels were determined for both endogenous and reporter transcripts using the RNAseq data. (Results of the DNAseq experiment are discussed below). Reporter transcripts were found to be among the most highly expressed genes (FIG. 10), representing approximately 1.7% of the total reads. As expected, reporter expression from UV-treated plasmids was reduced in a dose-dependent manner (FIG. 6c). The dose response for the XPA cell line (GM02344) was more pronounced than that for the cell line derived from an apparently healthy individual (GM01953), mirroring the pattern of dose response curves obtained when reporter expression for the same samples was estimated using flow cytometry (FIG. 6b). Reporter expression from plasmids containing a site-specific CPD in the transcribed strand was likewise reduced in an NER-dependent manner (FIG. 11). Very few endogenous transcripts showed a significant (greater than 2-fold) change in expression in the presence of UV treated plasmids, and those that were detected are not known to play an important role in DNA repair (Supplemental Table S6).

Figure 7:
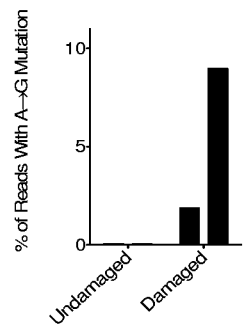
FIG. 7 shows transcriptional mutagenesis opposite a site-specific thymine dimer. a) Percentage of reads containing a deletion that spans the site of the thymine dimer, as measured by RNAseq (the sequences, from top to bottom, correspond to SEQ ID NOs.: 8 and 9) or b) DNAseq (the sequence corresponds to SEQ ID NO: 8). c) Percentage of reads in which guanine has been misincorporated in place of the expected 3' adenine in the sequence opposite the thymine dimer, measured by RNAseq or d) DNAseq.
Figure 7:
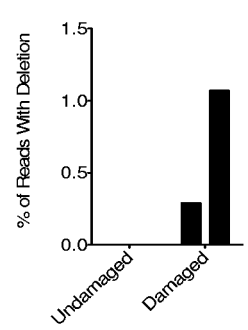
Figure 7:
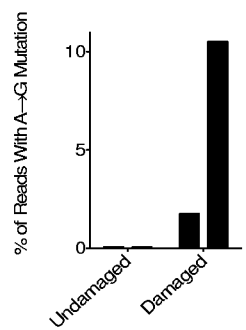
Figure 7:
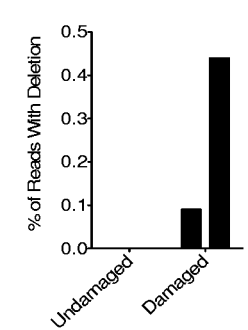
Figure 12:
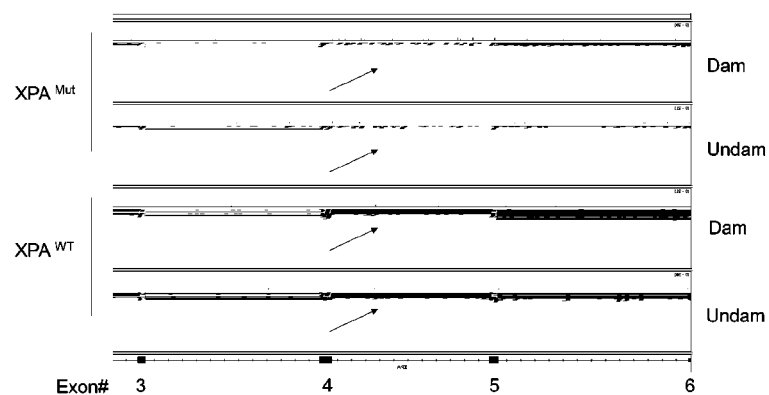
FIG. 12 shows read coverage and junction reads for GM02344 "$XPA^{mut}$" and GM01953 "$XPA^{WT}$". Reads are aligned to the region of the genome that encodes the XPA gene (diagrammed at the bottom of the figure). The majority of reads in GM01953 align, as expected, to the exons (3, 4, and 5 are shown). Read coverage is overall higher and the expected intron-spanning reads (indicated as light blue lines that run between exons) are abundant. By contrast, read coverage is lower, intron spanning reads are nearly absent, and a significant number of reads within the introns all support an elevated frequency of splicing errors in the XPA gene in GM02344.

Sequence-level analysis of transcripts confirmed a previously reported miss-splice in intron 4 of the XPA transcript for cell line GM02344, and revealed changes in reporter transcripts at the position corresponding to the site-specific CPD in the transcribed strand for both cell lines. Base substitutions and rare deletions were detected in reporter transcripts at the position corresponding to the site-specific CPD (FIG. 7). The most frequently observed base change, an A→G mutation at the 3' Adenine in the ApA sequence opposite the CPD, was detected at a frequency of about 1.5% of reads in cells with no known repair defect (GM01953), and at an elevated rate of about 10% of reads in the repair deficient cells from GM02344 (FIG. 7a). In transcripts expressed from the undamaged plasmid, the frequency of the A→G mutation was less than 0.1%. Rare deletions spanning the ApA sequence were detected at a frequency of 0.37% for GM01953, and 1% for GM02344 (FIG. 7b). Deletions were not observed at this position in transcripts expressed from the undamaged reporter plasmid. Frequencies for additional sequence changes observed opposite the site-specific CPD are provided in Supplemental Table S7. Turning to endogenous transcripts, reduced expression and an expected lack of regular junction reads spanning intron 4 of the XPA gene from GM02344 was observed (FIG. 12), confirming a previously reported missplice in XPA transcripts due to the homozygous 555G>C mutation [22].

Figure 13:
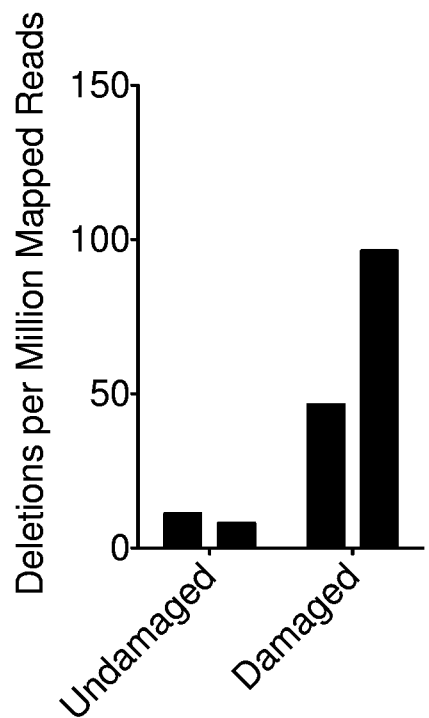
FIG. 13 shows the frequency of deletions of 3 or more base pairs and spanning ApA sites in reads aligning to randomly damaged reporter sequences. Dark grey bars represent GM01953 (WT) and light grey represents GM02344 (XPA mutant). In the absence of UV irradiation, a background frequency of about 10 per million reads is observed. The frequency rises to about 50 reads per million in GM01953, and still higher to about 100 reads per million in GM02344. This pattern is similar to that observed for the frequency of deletions at the position of the site specific lesion, providing additional evidence that the deletions are due to error-prone transcriptional bypass of unrepaired bulky DNA adducts.

Selective amplification of cDNA derived from reporter transcripts yielded a 50-fold enrichment of reads aligning to reporter sequences, and corroborated results obtained from the RNAseq analysis. Among reads associated with the DNAseq samples, 74,621,260 (84.7%) aligned to at least one of the five reporter genes. In order to compare data from the DNAseq experiment directly with those from the RNAseq experiment, RPKM values were calculated for both data sets. Dose response curves generated from the DNAseq data recapitulated the trends observed in those generated from both RNAseq and flow cytometry data (FIG. 6d). Unexpectedly, expression from the reporter containing a site-specific CPD appeared to be higher in the XPA deficient cell line (GM02344) than in the one derived from an apparently healthy individual (GM01953). The pattern of sequence level changes in transcripts at the position corresponding to the site-specific CPD was similar to that detected in the RNAseq data (FIG. 7), however the frequency of deletions was reduced slightly relative to that estimated from the RNAseq data (FIG. 7d). Rare deletions spanning ApA sequences in reporters from the randomly UV-damaged reporters were also detected (FIG. 13), with the highest frequency again observed in reporter isolated from Phoebe. Frequencies for additional sequence changes observed opposite the site-specific CPD are provided in Supplemental Table S8.

Discussion

Despite the critical role of DNA repair in preventing disease, methods of measuring DNA repair capacity have so far lagged behind the demands that must be met if such a metric is to be used to personalize the prevention and treatment of cancer and other diseases caused by inefficient repair of DNA damage. We present several new tools that enable rapid, high throughput measurements of DNA repair capacity for any lesion that affects either the level or the sequence of reporter transcripts.

The flow cytometric HT-HCR method reproduced data collected previously for the same cell lines [8]. By using multiple fluorescent reporters, a 96-well format, and automated sample processing, the method is much faster and less labor intensive than the standard CAT-based HCR assay. Flow cytometers equipped with a high throughput sampler enable collection of multiple time points from a single transfection without the requirement for significant additional labor. Furthermore, experimental errors are reduced by co-transfection of reporters, with normalization to an undamaged control plasmid that is included in every transfection. Because standard oncology labs are equipped with flow cytometers, the assay can readily be used in a clinical setting. Thus, the HT-HCR removes a major barrier to epidemiological studies of DNA repair capacity that include large populations, and potentially more than one repair pathway.

We demonstrated an application of the HT-HCR to the question of whether NER capacity in human lymphoblastoid cells is representative of repair capacity in other tissues.

Lymphoblastoid cells provide a convenient source of large numbers of cells for use in human variability studies, however the extent to which they represent a faithful surrogate for other cells in primary tissues has been called into question [23-25]. The present data indicate a strong correlation between NER capacity in primary human fibroblasts and the transformed B-lymphoblastoid cells (FIG. 4). The strong correlation further illustrates that the assay can be carried out reproducibly in cells with disparate morphology.

Figure 6:
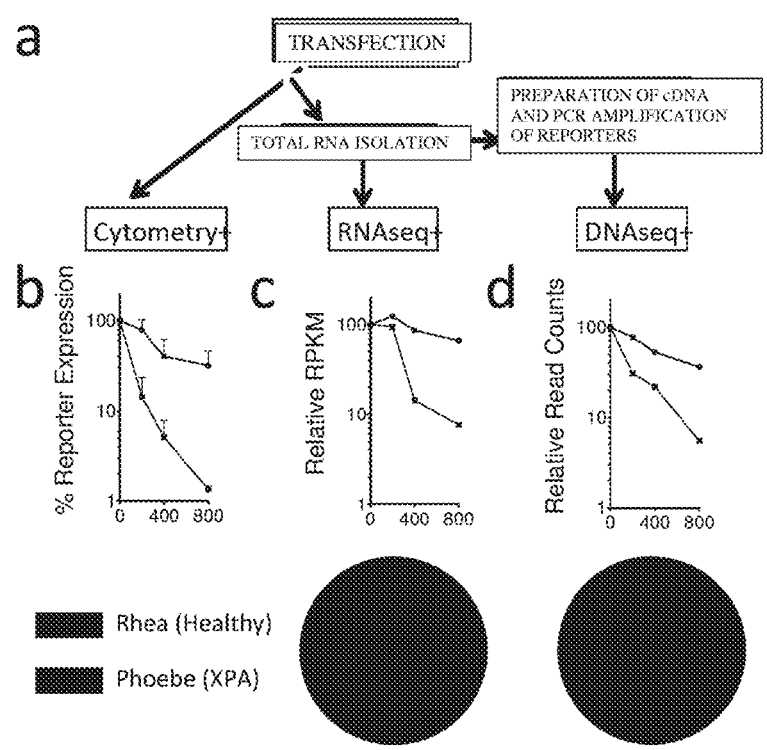
FIG. 6 shows the validation of HCR-Seq against HT-HCR. a) workflow for experiments comparing three methods of quantifying reporter expression. b) Dose response curves generated for cells transfected with plasmid combination #3 from Table 2, and assayed by HT-HCR. Error bars represent the standard deviation of biological duplicates. c) Corresponding dose-response curves generated from RNAseq data. In the pie chart, the fraction of mapped reads aligning to reporter transcripts is represented in black, and all other reads are represented in gray. d) Dose response curves generated from DNAseq data. Reads aligning to reporters are again represented in black, and all others are represented in gray.

The use of next generation sequencing to detect reporter transcripts themselves (HCR-seq), in place of their fluorescent translation products, allows for an increase in throughput, and to measure repair events that are not readily detected using flow cytometric approaches. We have validated the HCR-seq approach by showing that a similar pattern of dose-response curves is obtained for HCR of UV-irradiated plasmids as detected by three methods (FIG. 6). Whereas HT-HCR allowed for the simultaneous detection of 5 independent repair reporters, the HCR-seq permitted the measurement of 40 reporters (5 reporter genes×8 bar-codes). In the context of the RNAseq data, 20 of these reporters were detected at a sufficient coverage to obtain dose response curves (FIG. 6). As these represented less than 1% of the total mapped reads in the experiment, it can be estimated that at least 2000 reporters (or 200 dose-response curves) could be independently assayed on a single lane if endogenous transcripts were excluded from the assay. The robustness of the data after selective PCR amplification demonstrates the feasibility of such experiments.

The four dose response curves derived from sequencing data and presented in FIGS. 6c and 6d were acquired at a cost of approximately $750/curve. However, several considerations would reduce the cost of sequencing-based assays if deployed in large scale population studies. As cost of sequencing continues to fall, and particularly if a large number of samples is multiplexed on single lane, sample preparation can be expected to dominate the cost of the assay, with sequencing accounting for a small fraction of the overall cost. Although in the present work bar-codes were introduced as part of the Illumina sample preparation pipeline, an equivalent means of distinguishing among samples would be to introduce bar-codes into the library of reporter plasmids. This configuration would permit sample pooling prior to sequencing library preparation, leaving the cost of cell culture and transfection reagents as the major remaining cost of the assay.

HCR-seq constitutes a paradigm shift in the quantitation of DNA repair capacity because of the ability to measure the repair of any lesion that induces transcriptional mutagenesis. This is an important advance because many DNA lesions can be bypassed by human RNA polymerase. As a result, they cannot be detected by a conventional HCR assay without the requirement for reporters specifically engineered to give a functional reporter protein in the presence of the lesion [26]. HCR-seq has no such requirement, so rare or unexpected transcriptional mutagenesis events can be detected. Base misincorporation opposite DNA lesions by RNA polymerase during transcription often mirrors that by DNA polymerase during replication. Thus, most mutagenic lesions have a transcriptional mutagenic signature [27]. The HCRseq strategy should therefore be useful in DNA repair capacity measurements for nearly any pathway. The data in FIG. 7 illustrate the power of this unbiased approach to detect rare events that are specific to transcription of damaged DNA. Because the plasmids are not replicated in the cell, and sequence changes were observed at an elevated rate in repair deficient cells, these are likely to reflect transcriptional mutagenesis events at unrepaired DNA lesions in the transcribed strand.

In addition to the possible clinical applications described above, HCRseq allows for the elucidation of new biological phenomena in the research setting. The observed 6-8 base pair deletions at ApA sequences opposite a site specific CPD are consistent with a recent report that bulky, helix-distorting lesions can be bypassed by human RNA polymerase II, giving rise to rare transcriptional mutagenesis events, including deletions [28]. However, the observation of frequent base misincorporation opposite a CPD by RNA polymerase II appears to be without precedent. A recent study indicated that CPD bypass followed the so-called "A-rule", resulting in error-free bypass [29]. In that study, base misincorporation was observed, however subsequent extension of transcripts beyond a misincorporated base was strongly inhibited. The present data provide evidence of error-prone transcriptional bypass of bulky DNA lesions in human cells followed by completion of the transcript. A lower limit (about 10%) for the frequency of these bypass events can be estimated from the data in FIG. 7. Since it is expected that reporter plasmids that have already been repaired or did not contain a thymine dimer at the time of transfection will be transcribed at a higher rate, and because error-free bypass cannot be distinguished from transcripts arising from repaired plasmid, the rate of bypass may be higher than 10%.

Conclusions

HT-HCR and HCRseq represent powerful new tools for high throughput measurements of human DNA repair capacity. HT-HCR permits the rapid and simultaneous measurement of at least 4 independent repair processes in a single assay. HCR-seq has the potential to measure thousands of repair processes in a single assay, and expands the type of lesions whose repair can be measured to include those that do not block transcription. The use of sample-specific bar-codes permits the simultaneous measurement of repair capacity in multiple individuals, thereby minimizing inter-experimental variability. The use of barcodes with HCR-seq also has the potential to reduce the cost and labor required for DNA repair capacity measurements to a level compatible with large scale epidemiological studies and clinical diagnostic/prognostic applications. Both assays hold an advantage over methods requiring cell lysis because the intact DNA repair machinery of a living cell acts on nuclear DNA, thus increasing the likelihood of recapitulating physiological DNA repair phenotypes. As a research tool, the unbiased HCRseq approach also has the potential to reveal previously unknown mechanisms of DNA repair and damage tolerance.

TABLE 1

Cell lines used in this study.
To facilitate comparison of data, the seven individuals from whom both lymphoblastoid and fibroblast cultures were derived have been assigned indexes α through η.

| Cell Line | Individual | Cell Type | Genotype | NER Phenotype |
| --- | --- | --- | --- | --- |
| GM01630 (α) | Phoebe | Fibroblast | XPA | Severe |
| GM01953 | Rhea | Lymphoblastoid | WT | None |
| GM02246 | Cronus | Lymphoblastoid | XPC | Moderate |

TABLE 1-continued

Cell lines used in this study.
To facilitate comparison of data, the seven individuals from whom both lymphoblastoid and fibroblast cultures were derived have been assigned indexes α through η.

| Cell Line | Individual | Cell Type | Genotype | NER Phenotype |
| --- | --- | --- | --- | --- |
| GM02249 | Mnemosyne | Lymphoblastoid | XPC | Mild |
| GM02253 | Oceanus | Lymphoblastoid | XPD | Severe |
| GM02344 (α) | Phoebe | Lymphoblastoid | XPA | Severe |
| GM02345 | Coeus | Lymphoblastoid | XPA | Severe |
| GM03657 (β) | Hyperion | Lymphoblastoid | WT | None |
| GM03658 (β) | Hyperion | Fibroblast | WT | None |
| GM07752 (γ) | Tethys | Lymphoblastoid | WT | None |
| GM07753 (γ) | Tethys | Fibroblast | WT | None |
| GM14878 (δ) | Theia | Lymphoblastoid | XPC | Very Mild |
| GM14879 (δ) | Theia | Fibroblast | XPC | Very Mild |
| GM21071 (ε) | Themis | Fibroblast | XPB | Severe |
| GM21148 (ε) | Themis | Lymphoblastoid | XPB | Severe |
| GM21677 (ζ) | Crius | Lymphoblastoid | WT | None |
| GM21833 (η) | Iapetus | Lymphoblastoid | WT | None |
| GM23249 (ζ) | Crius | Fibroblast | WT | None |
| GM23251 (η) | Iapetus | Fibroblast | WT | None |

TABLE 2

Combinations of reporter plasmids used in each experiment.
Dose to plasmid is given in units of $J/m^2$.

| Combination | BFP | Cyan | GFP | mOrange | mPlum |
| --- | --- | --- | --- | --- | --- |
| #1 | 600 | 0 | 800 | 200 | 400 |
| #2 | 0 | 200 | 400 | 600 | 800 |
| #3 | 0 | 200 | T<>T[1] | 400 | 800 |

[1]Site specific thymine dimer

TABLE 3

8 bar-coded samples submitted for deep sequencing on a single lane.

| Sample | Cell line | Damage to Plasmid | Barcode | Sequencing Type | Number of Reads aligned to reporters |
| --- | --- | --- | --- | --- | --- |
| A | GM2344 | No | CTACTG | RNA | 501791 |
| B | GM2344 | Yes | GGCAAC | RNA | 141195 |
| C | GM1953 | No | TCGTCA | RNA | 503521 |
| D | GM1953 | Yes | TAGGCT | RNA | 422704 |
| E | GM2344 | No | ATGATA | DNA | 14083169 |
| F | GM2344 | Yes | CAAGTT | DNA | 19129464 |
| G | GM1953 | No | GTCCAG | DNA | 22275922 |
| H | GM1953 | Yes | TGGACC | DNA | 22511231 |

TABLE S1

Cufflinks and Tophat parameters.

| | Value | Description |
| --- | --- | --- |
| Tophat parameter | | |
| min-anchor-length | 6 | TopHat will report junctions spanned by reads with at least this many bases on each side of the junction. Note that individual spliced alignments may span a junction with fewer than this many bases on one side. However, every junction involved in spliced alignments is supported by at least one read with this many bases on each side. This must be at least 3 and the default is 8. |

TABLE S1-continued

Cufflinks and Tophat parameters.

| | Value | Description |
|---|---|---|
| splice-mismatches | 0 | The maximum number of mismatches that may appear in the "anchor" region of a spliced alignment. The default is 0. |
| min-intron-length | 10 | minimum intron size allowed in genome |
| max-intron-length | 1000000 | maximum intron size allowed in genome |
| min-isoform-fraction | 0.0 | The minimum frequency of any isoform to consider. The default is 0.15 |
| max-multihits | 20 | Instructs TopHat to allow up to this many alignments to the reference for a given read, and suppresses all alignments for reads with more than this many alignments. The default is 20 for read mapping. |
| no-novel-juncs | True | Only look for reads across junctions indicated in the supplied GFF or junctions file. |
| segment-length | 20 | Each read is cut up into segments, each at least this long. These segments are mapped independently. The default is 25. |
| library-type | fr-unstranded | library prep used for input reads |
| solexa1.3-quals | True | As of the Illumina GA pipeline version 1.3, quality scores are encoded in Phred-scaled base-64. Use this option for FASTQ files from pipeline 1.3 or later. |
| Cufflinks parameters | | |
| min-intron-length | 10 | minimum intron size allowed in genome |
| max-intron-length | 1000000 | maximum intron size allowed in genome |
| min-isoform-fraction | 0.0 | The minimum frequency of any isoform to consider. The default is 0.15 |
| library-type | fr-unstranded | library prep used for input reads |
| compatible-hits-norm | True | count hits compatible with reference RNAs only |
| multi-read-correct | True | use 'rescue method' for multi-reads (more accurate) |
| frag-bias-correct | True | use bias correction - reference fasta required |

TABLE S2

Read counts for RNA-seq samples and numbers of aligned reads using Tophat.

| | | XPA mut undam | XPA mut dam | Norm undam | Norm dam |
|---|---|---|---|---|---|
| Total reads | | 22903329 | 21345212 | 23454955 | 24408453 |
| Unaligned | | 428195 | 358787 | 448506 | 453861 |
| Aligned to all | Total | 26504278 | 24805211 | 27527409 | 28496167 |
| | Ambiguous | 4495789 | 4250691 | 4992157 | 5018134 |
| | Unique | 22008489 | 20554520 | 22535252 | 23478033 |
| Aligned to human genome | Total | 26002487 | 24664016 | 27023888 | 28073463 |
| | Ambiguous | 4430397 | 4246605 | 4926437 | 4975358 |
| | Unique | 21572090 | 20417411 | 22097451 | 23098105 |
| Aligned to reporter | Total | 501791 | 141195 | 503521 | 422704 |
| | Ambiguous | 126142 | 7612 | 124807 | 81196 |
| | Unique Total | 375649 | 133583 | 378714 | 341508 |
| | BFP | 28462 | 19299 | 28104 | 26471 |
| | AmCyan | 143700 | 90582 | 155397 | 184217 |
| | GFP_615 | 39654 | 12250 | 38082 | 25282 |
| | mOrange | 49208 | 5249 | 46614 | 38222 |
| | mPlum | 114625 | 6203 | 110517 | 67316 |

TABLE S3

RPKM values for the five reporter genes across samples.

| Reporter gene | RPKM values | | | |
|---|---|---|---|---|
| | XPA mut undam | XPA mut dam | Norm undam | Norm dam |
| BFP | 2480.96 | 1792.89 | 2444.02 | 2254.98 |
| AmCyan | 14427.1 | 9816.38 | 15365.9 | 17441.2 |
| GFP_615 | 3281.55 | 1077.19 | 3148.35 | 2057.57 |
| mOrange | 6642.74 | 683.994 | 6356.26 | 5046.36 |
| mPlum | 14995 | 829.241 | 14584.1 | 8869.09 |

TABLE S4

Read counts for RNA-seq samples and numbers of aligned reads using TopHat.

|  |  | XPA mut undam | XPA mut dam | Norm undam | Norm dam |
|---|---|---|---|---|---|
| Total reads |  | 15477805 | 22428323 | 24517460 | 25680796 |
| Unaligned |  | 2541912 | 3488151 | 3461562 | 3618298 |
| Aligned to all | Total | 14097831 | 19153649 | 22299508 | 22546451 |
|  | Ambiguous | 1416044 | 643871 | 1663555 | 872727 |
|  | Unique | 12681787 | 18509778 | 20635953 | 21673724 |
| Aligned to human genome | Total | 14662 | 24185 | 23586 | 35220 |
|  | Ambiguous | 2396 | 3755 | 3676 | 5589 |
|  | Unique | 12266 | 20430 | 19910 | 29631 |
| Aligned to reporter | Total | 14083169 | 19129464 | 22275922 | 22511231 |
|  | Ambiguous | 1413648 | 640116 | 1659879 | 867138 |
|  | Unique Total | 12669521 | 18489348 | 20616043 | 21644093 |
|  | BFP | 1266523 | 6137156 | 2162883 | 3159934 |
|  | AmCyan | 3571988 | 6115952 | 10360183 | 14648713 |
|  | GFP_615 | 1376690 | 3459175 | 908607 | 287825 |
|  | mOrange | 2388861 | 1766014 | 2737414 | 1610236 |
|  | mPlum | 5479030 | 1651015 | 6106623 | 2804324 |

TABLE S5

RPKM values for five reporter genes generated by TopHat and Cufflinks analysis of the DNA sequence data.

| Reporter genes | XPA mut undam | XPA mut dam | Norm undam | Norm dam |
|---|---|---|---|---|
| BFP | 142139 | 501211 | 127941 | 212433 |
| AmCyan | 541422 | 586301 | 862136 | 1103440 |
| GFP_615 | 138125 | 273507 | 46110.2 | 13027.7 |
| mOrange | 154654 | 118996 | 116079 | 102183 |
| mPlum | 587504 | 114037 | 406956 | 244267 |

TABLE S6

Genes with log2 fold change >= 1 when comparing cells transfected with undamaged plasmid to those transfected with damaged plasmids.

| RPKM cutoff | Sample | Gene Name | Chr | Bp | Log2 Fold Change |
|---|---|---|---|---|---|
| RPKM >= 5 | XPA mut | RPL21 | chr13 | 27825691-27830702 | 1.480810166 |
|  |  | DDX39B | chr6_apd_hap1 | 2812683-2821649 | 2.297351567 |
|  |  | GFP_615 | GFP_615 | 0-951 | -1.607104673 |
|  |  | SMN2 | chr5 | 69345349-69373422 | -1.265076988 |
|  |  | SMN2 | chr5 | 70220767-70248842 | -1.282415323 |
|  |  | mOrange | mOrange | 0-942 | -3.279722873 |
|  |  | mPlum | mPlum | 0-912 | -4.176546263 |
|  | Normal | ARRDC3 | chr5 | 90664540-90679149 | 1.420496975 |
|  |  | SCARNA27 | chr6 | 8086640-8086766 | 1.547032054 |
| RPKM >= 1 | XPA mut | OSCP1 | chr1 | 36883506-36916086 | 1.052446063 |
|  |  | RPL21 | chr13 | 27825691-27830702 | 1.480810166 |
|  |  | SELM | chr22 | 31500762-31503551 | 1.269204139 |
|  |  | LOC100505894 | chr5 | 87564698-87732491 | 1.183911485 |
|  |  | HIST1H2BH | chr6 | 26251878-26252303 | 1.097113886 |
|  |  | HIST1H2BN | chr6 | 27806439-27806888 | 1.292384444 |
|  |  | DDX39B | chr6_apd_hap1 | 2812683-2821649 | 2.297351567 |
|  |  | GFP_615 | GFP_615 | 0-951 | -1.607104673 |
|  |  | HIST2H3A | chr1 | 149812258-149812765 | -1.009472345 |
|  |  | HIST2H3A | chr1 | 149824180-149824687 | -1.009472345 |
|  |  | FAM45B | chr10 | 120863628-120897376 | -1.415998178 |
|  |  | PLSCR3 | chr17 | 7293046-7298162 | -1.085829966 |
|  |  | SMN2 | chr5 | 69345349-69373422 | -1.265076988 |
|  |  | SMN2 | chr5 | 70220767-70248842 | -1.282415323 |
|  |  | LEAP2 | chr5 | 132209357-132210582 | -1.210275283 |
|  |  | HIST1H2BO | chr6 | 27861202-27861669 | -1.294428563 |
|  |  | mOrange | mOrange | 0-942 | -3.279722873 |
|  |  | mPlum | mPlum | 0-912 | -4.176546263 |
|  | Normal | C1orf162 | chr1 | 112016603-112021134 | 1.023536205 |
|  |  | ZNF826P | chr19 | 20578625-20607771 | 1.359917941 |
|  |  | IL29 | chr19 | 39786964-39789312 | 1.01622561 |
|  |  | C21orf119 | chr21 | 33765441-33766266 | 1.058253039 |
|  |  | ARRDC3 | chr5 | 90664540-90679149 | 1.420496975 |
|  |  | SPATA24 | chr5 | 138732455-138739776 | 1.170374309 |
|  |  | EEF1E1-MUTED | chr6 | 8013799-8102828 | 1.336028163 |
|  |  | SCARNA27 | chr6 | 8086640-8086766 | 1.547032054 |
|  |  | RPPH1 | chr14 | 20811229-20811570 | -1.018946998 |

TABLE S6-continued

Genes with log2 fold change >= 1 when comparing cells transfected with undamaged plasmid to those transfected with damaged plasmids.

| RPKM cutoff | Sample | Gene Name | Chr | Bp | Log2 Fold Change |
|---|---|---|---|---|---|
| | | PLSCR3 | chr17 | 7293046-7298162 | −2.245649866 |
| | | TMEM238 | chr19 | 55890611-55895627 | −1.080267671 |
| | | EIF4EBP3 | chr5 | 139927250-139929163 | −1.563613927 |
| | | GTF2IP1 | chr7 | 72569025-72621336 | −1.031276973 |
| | | RMRP | chr9 | 35657747-35658015 | −1.351587952 |

TABLE S7

Observed frequency of sequence changes in reporter transcripts at positions corresponding to the site specific CPD.

| | GM01953 | | GM02344 | |
|---|---|---|---|---|
| | Undamaged | Damaged | Undamaged | Damaged |
| Delete ApA opp T< >T | 0.00% | 0.29% | 0.00% | 1.07% |
| AA Del, Randomly Dam[1] | 17.9 | 23.7 | 14.0 | 42.5 |
| 5'A-->G | 0.07% | 1.87% | 0.15% | 8.97% |
| 3'A-->T | 0.00% | 0.34% | 0.00% | 1.89% |

[1]Deletions per million mapped reads

TABLE S8

Observed frequency of sequence changes in reporter transcripts at positions corresponding to the site specific CPD (DNAseq data).

| | GM01953 | | GM02344 | |
|---|---|---|---|---|
| | Undamaged | Damaged | Undamaged | Damaged |
| Delete ApA opp T< >T | 0.00% | 0.09% | 0.00% | 0.44% |
| AA Del, Randomly Dam[1] | 1.4 | 9.5 | 0.0 | 26.8 |
| 5'A-->G | 0.07% | 1.75% | 0.07% | 9.73% |
| 3'A-->T | 0.01% | 0.17% | 0.01% | 1.21% |

[1]Deletions per million mapped reads

Example 2: Construction of Reporter Constructs

Most of the multiple cloning (MCS) of plasmid pmax Cloning was excised to minimize the size of the reporter, leaving only the KpnI and SacI restriction sites (see MCS diagram at bottom of FIG. 15), plus two restriction sites (illustrated in blue) introduced for convenient subcloning of reporter genes of the following general structure: KpnI-NheI-Reporter_Gene-HindIII-SacI. The resulting reporter plasmids lack any mammalian origin of replication, and express no other gene except for the reporter in mammalian cells. This construction was used to characterize DNA repair mechanisms independently DNA replication. However, plasmids that can be replicated in human cells are used to study the repair and tolerance of DNA damage in the context of DNA replication.

Example 3: Multicolor Fluorescent Reporter Strategy

Figure 16:
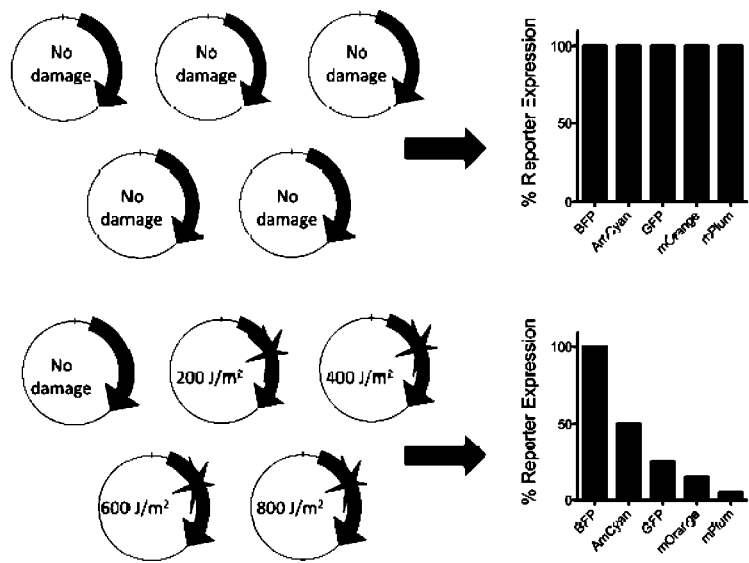
FIG. 16 is a drawing illustrating the multicolor fluorescent reporter strategy. The column graphs show expected data for reporter expression from DNA repair reporter vectors irradiated with UVC at several doses.

Damage induced in DNA by UV-irradiation is known to block transcription. As this damage is repaired, transcription is restored. As shown in FIG. 16, 5 five plasmids encoding separate reporter proteins, BFP (blue), AmCyan (Cyan), GFP (Green), mOrange (Orange) and mPlum (Red) are co-transfected into cells to establish a control level of fluorescent reporter expression from undamaged plasmids, typically at 24 hours (top of FIG. 16). 4 Four reporters are selected as repair capacity reporters, and normalized to a fifth color (in this case BFP), that is included as a transfection control. To measure nucleotide excision repair capacity, a different dose of UVC irradiation ranging from 0-800 J/m2 is delivered to each reporter (in general, either the dose or the type of damage can be varied, depending on the DNA repair pathway to be interrogated). As described, BFP is left undamaged, and its expression level used as a transfection control. The damaged reporters are mixed and co-transfected into cells. After allowing for a period of DNA repair, the level of expression is determined for each reporter and expressed as a percentage of control (undamaged) reporter expression. Expected data are shown in FIG. 16, right panels.

Example 4: Flow Cytometric Detection and Measurement of Reporter Fluorescence

Figure 17:
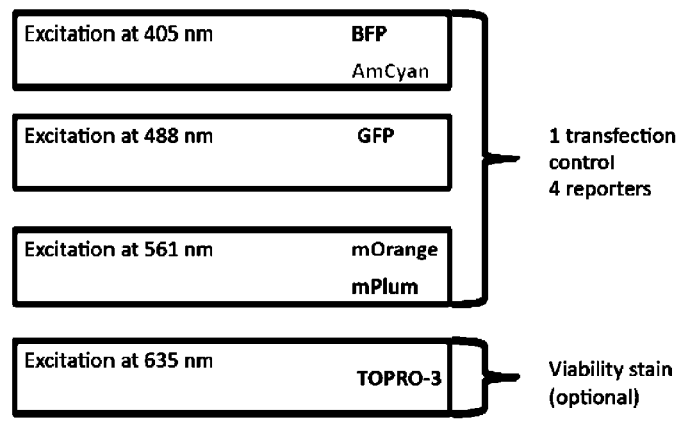
FIG. 17 is a drawing that shows flow cytometric detection and measurement of reporter fluorescence. The wavelength of the laser used to excite fluorophores is given in nm.
Figure 18:
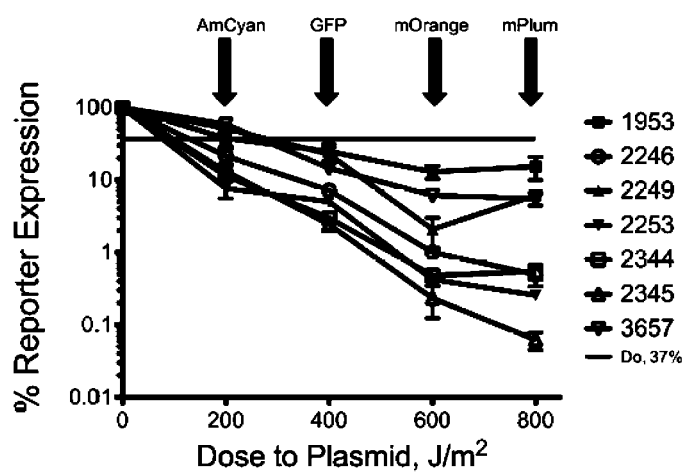
FIG. 18 is a graph of a dose response curve corresponding to the multicolor fluorescent reporter strategy shown in FIG. 16.
Figure 19:
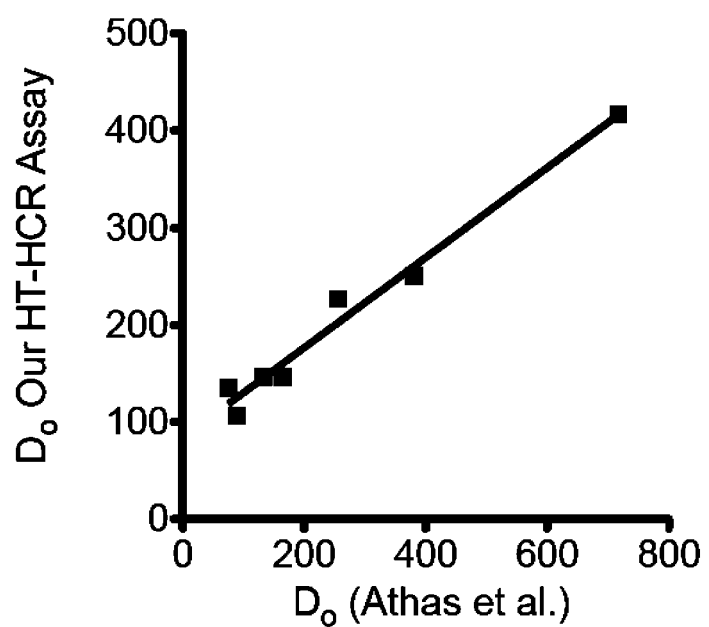
FIG. 19 is a graph showing the correlation between $D_o$ as calculated by Athas et al. and $D_o$ obtained using the developed assay.

As shown in FIG. 17, BFP and AmCyan are excited using a 405 nm laser, and detected in the pacific blue and AmCyan detectors, respectively. GFP is excited at 488 nm and measured in the FITC detector. mOrange and mPlum are excited at 561 nm and detected in the PE and PE-Cy5-5 detectors, respectively. TOPRO®-3, used to exclude dead cells from the analysis, is excited at 634 nm and measured in the APC detector. Using positive and negative controls, a positive region defined as follows is established for each reporter: Cells expressing the reporter fall in this region, and when the reporter is excluded from a transfection in which all other reporters are present, no cells fall in this region. Expression for each reporter is calculated as the percentage of cells appearing in the positive region, multiplied by their mean fluorescence intensity (MFI+) in the appropriate detector.

Example 5: Dose Response Curve Corresponding to the Multicolor Fluorescent Reporter Strategy Seven cell lines previously characterized for their nucleotide excision repair capacity (Athus et al. Cancer Res 1991 51, pp. 5786-5793) were studied using the developed assay. Expression of fluorescent reporter protein from damaged plasmids (AmCyan, 200 J/m2, GFP, 400 J/m2; mOrange 600 J/m2; mPlum, 800 J/m2) was plotted in FIG. 18 as a percentage of expression from the respective undamaged control plasmids. A line corresponding to 37% was drawn in grey; this corresponds to the dose at which there is, on average, one transcription blocking event per reporter. The dose at which the curves shown in FIG. 18 cross this line is defined as $D_o$. This quantity represents a numerical measure of repair capacity with higher numbers indicating a higher repair capacity.

Example 6: Sequencing Based Detection of Reporter Transcripts

Figure 20:
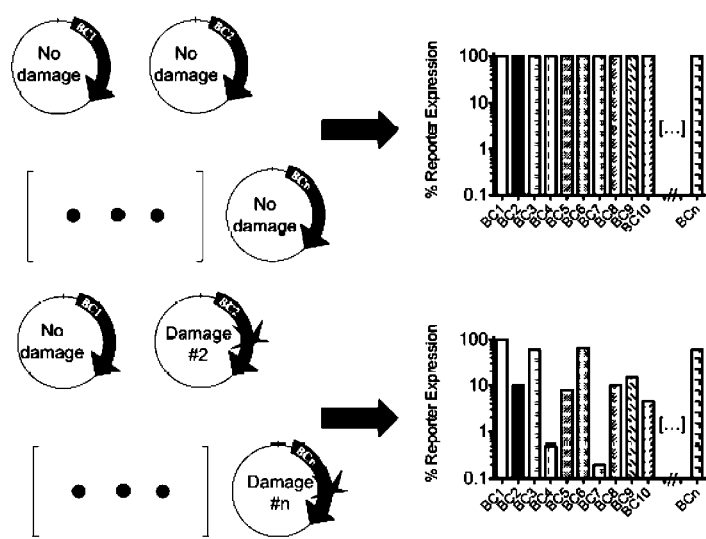
FIG. 20 is an illustration of sequencing based detection of reporter transcripts.
Figure 21:
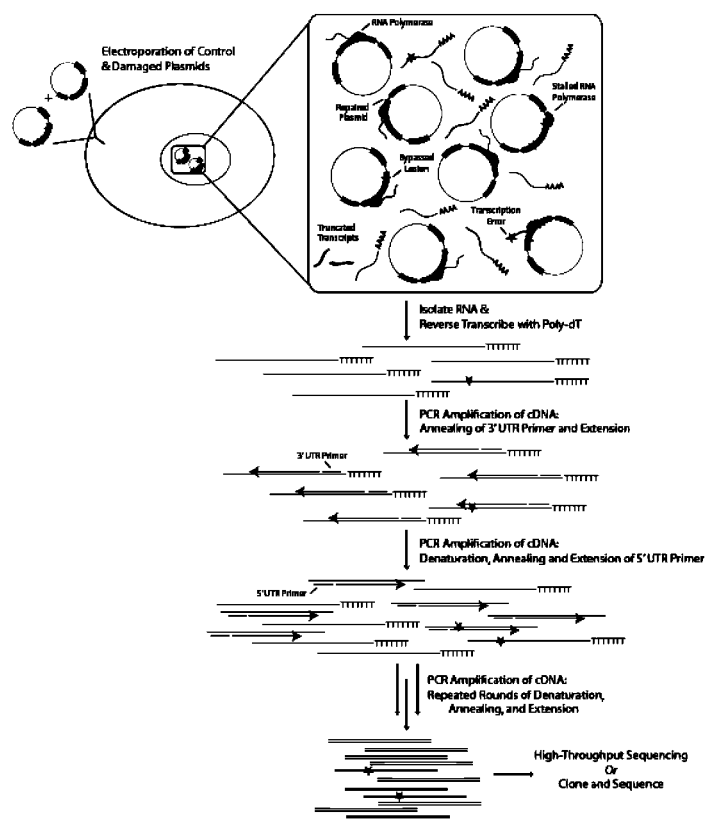
FIG. 21 is an illustration of the methodology for analysis of reporter transcripts by next generation sequencing. Transcripts can be analyzed directly by RNAseq or can be converted to cDNA and selectively amplified to increase the signal-to-noise ratio for DNA sequencing.

A library of plasmids containing short DNA barcodes (BC1, BC2, . . . BCn) within the transcribed region of a reporter gene under the CMV promoter is generated (FIG. 20). Cells are transfected with the library of undamaged, bar-coded plasmids to establish a control level of reporter expression. Transcripts are counted using deep sequencing as seen in FIG. 21. A unique dose or type of DNA damage is introduced into each of the bar-coded plasmids. As with the flow cytometric system described in FIG. 16, one bar-coded reporter (designated in FIG. 20 as BC1) is left undamaged for use as a transfection control. The mixture of damaged plasmids is co-transfected into cells, and after allowing time for DNA repair, transcripts are isolated from the cells, counted, and reported as a percentage of expression from the undamaged control.

Example 7: Methodology for Analysis of Reporter Transcripts by Next Generation Sequencing Cells are harvested, lysed, and their total RNA purified, and then further purified to mRNA using commercially available kits. Reverse transcription of reporter mRNAs to their corresponding cDNAs is achieved with reverse transcriptase, using either a poly-dT oligonucleotide, as shown in FIG. 21, or a reporter-specific oligonucleotide as a primer. Signal to noise is increased by subsequently PCR amplifying the reporter cDNAs with primers specific to the 5' and 3' UTR of the reporter transcripts (see FIG. 15 and FIG. 22). cDNA is then either cloned into plasmid vectors for conventional sequencing or submitted for next generation sequencing. In the case of next generation sequencing, additional barcodes may be appended at this stage to the 5' and 3' ends of cDNAs from replicate transfections, multiple time points or separate samples to enable multiplex sequencing in a single lane. Total reporter expression is measured as the number of sequencing reads that can be unambiguously assigned to the identifying bar-coded region of the reporter. Depending on the type of DNA damage, sequencing reads may be analyzed more deeply as shown FIG. 23. The primers used to amplify cDNA may be placed so as to flank any specific region of interest in the gene, as is needed in the case of site-specific DNA damage. (FIG. 21)

Figure 22:
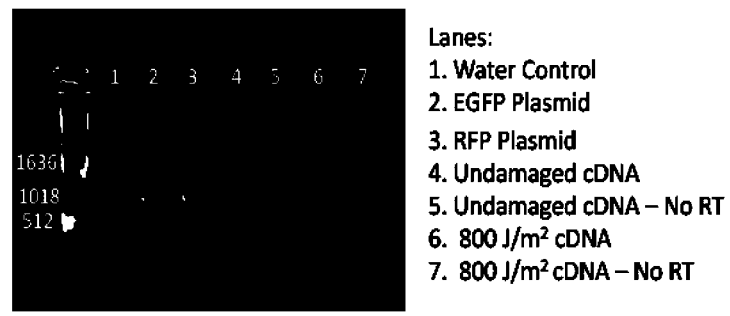
FIG. 22 is an image of a gel purification of cDNA amplified using reporter-specific primers. The gel shows cDNA amplified with the 5' and 3' UTR primers shown in FIG. 15.

Example 8: Gel Purification of cDNA Amplified Using Reporter-Specific Primers In this experiment, the RFP plasmid was either left undamaged or exposed to 800 j/m2 and then co-transfected with EGFP control plasmid into lymphoblastoid cells (FIG. 22). Total RNA was extracted, poly-dT purified, and reverse transcribed with poly-dT primers as described in FIG. 21. The lanes were used as follows: Lanes: 1—Water Control, Lane 2/3—Plasmid Positive Controls, 4/5—cDNA from undamaged HCR, +/− reverse transcription (RT), 6/7—cDNA from 800 j/m2 HCR, +/−. As the UTR primers amplify a region spanning the 136 bp chimeric intron in the pmax vector, plasmid templates were expected to give a slightly longer amplicon. Higher resolution experiments may be used to provide even stronger confirmation for the mass differences seen in the gel. The cDNA generated and amplified by these methods was cloned into plasmids and sequenced (see Table 2).

Figure 23:
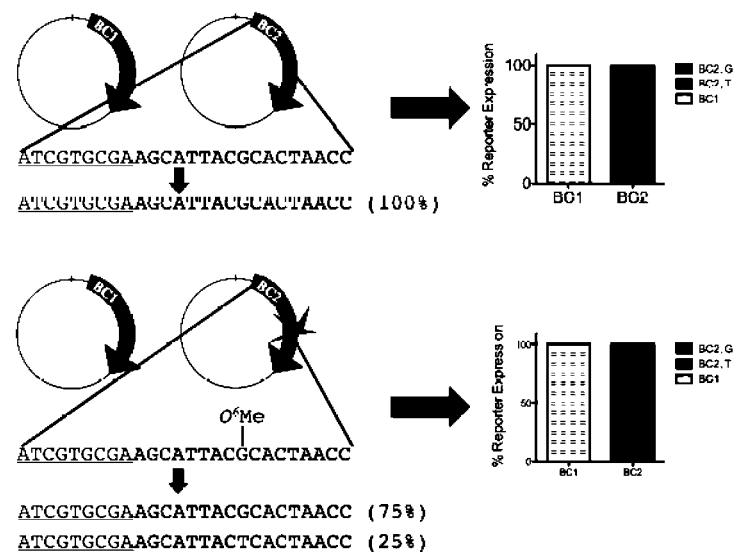
FIG. 23 is an illustration of the utility of single nucleotide resolution transcript analysis. (SEQ ID NO:4 and SEQ ID NO:5). The data in the column graphs are expected data based on the relative abundance of reporter transcripts for the lesion shown.
Figure 24:
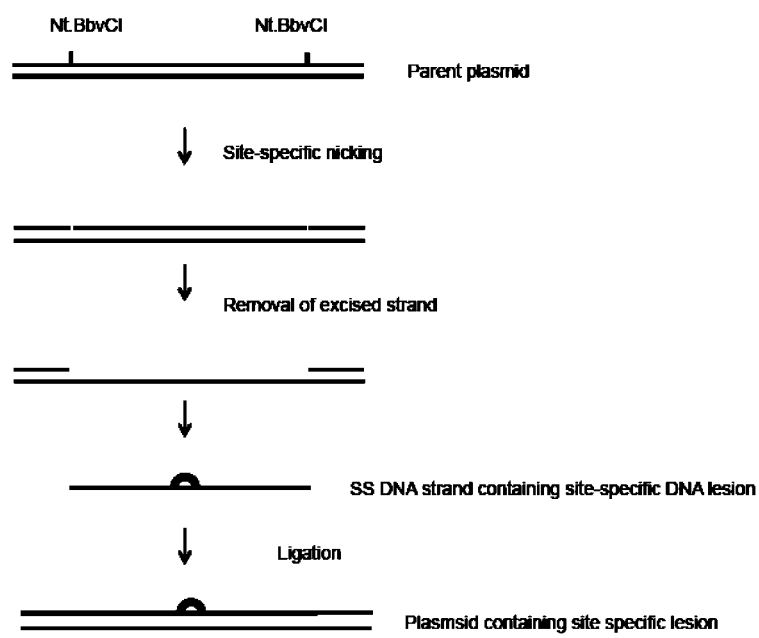
FIG. 24 is an illustration of a method used for the introduction of site-specific DNA lesions into reporter plasmids.
Figure 25:
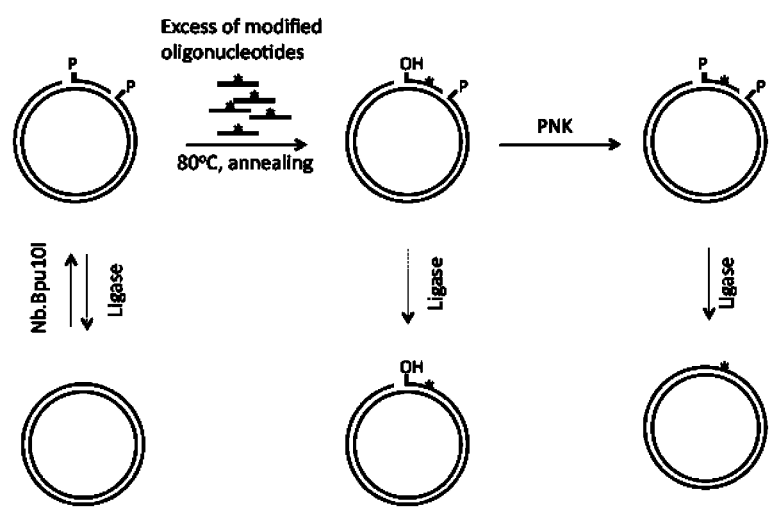
FIG. 25 is an illustration of the introduction of a site-specific thymine dimer into the pmax reporter plasmid.

Example 9: Evaluating the Utility of Single Nucleotide Resolution Transcript Analysis The fidelity of transcription in the presence of a given type of DNA damage may be evaluated from the frequency of errors detected in transcripts associated with a given bar code. In this example, the lesion $O^6$-methylguanine as indicated in red in FIG. 23, is site specifically incorporated into a reporter plasmid, 9 nucleotides downstream from a 9-nucleotide bar code (shown in grey). This lesion results from the miss-incorporation of uracil in mRNA with a frequency of approximately 25% (Dimitri, A., et al., Nucleic Acids Research, 2008. 36(20): p. 6459-6471.) Expected data are shown in the column graphs. During cDNA synthesis, the incorrect uracil is reverse transcribed to T, leading to a mixed population of cDNAs associated with that bar code. This is illustrated in FIG. 23 in the sequences shown with percentages immediately below the diagram of the reporter construct. Repair capacity is estimated from the rate at which the fraction of transcripts containing the correct nucleotide at this position increases. A time course is then carried out, ranging from 0 to up to 96 hours. The fraction of transcripts containing the correct nucleotide at the position of interest is calculated at each time point. Relative abundance of repaired to unrepaired substrate is at least equal to the ratio of correct transcripts to incorrect transcripts. The estimated time-dependent ratio of repaired to unrepaired substrate is used to calculate a relative rate of repair that can be compared among cell lines. This method may be generalized to any DNA lesion that alters the sequence transcribed from the reporter. In this example, where there is no inhibition of transcription, 100% total transcription of the damaged reporter is shown. However, some lesions may be expected to alter both the extent and fidelity of transcription. Both phenomena may be measured simultaneously by this method without modification.

Example 10: Introduction of Site-Specific DNA Lesions into Reporter Plasmids Single strand nicking sites were introduced flanking the position at which the lesion was to be introduced. The plasmid was cut with the nicking enzyme, and the excised strand was displaced by a single stranded oligonucleotide, shown red in FIG. 24, that is complimentary to the single stranded region created in the double-nicked plasmid. The displacing oligonucleotide contained a lesion, indicated in FIG. 24 as a red arch, at the desired position. Following annealing, the oligonucleotide was ligated into the plasmid.

Figure 26:
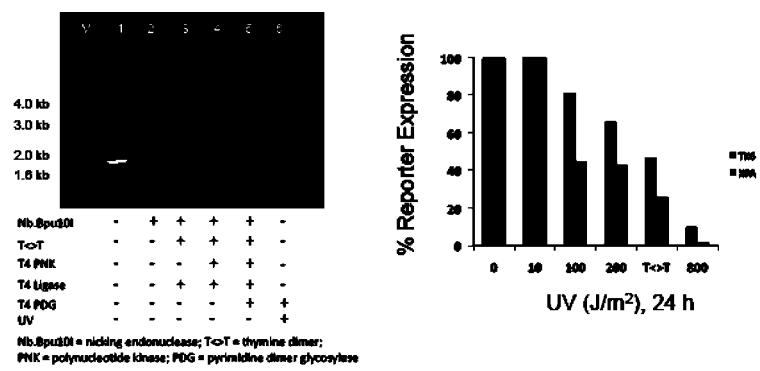
FIG. 26 is an image with a corresponding graph illustrating the verification of a site-specific DNA damage containing reporter.

Example 11: Introduction of a Site-Specific Thymine Dimer into the Pmax Reporter Plasmid Two nicking sites for the Nb.Bpu101 nicking endonuclease were introduced into the pmax GFP reporter. Following cutting, the plasmid was incubated with a large excess of modified oligonucleotides complimentary to the sequence spanned by the nicking sites in the plasmid. The modified oligonucleotides contained a site-specific thymine dimer, indicated as a star (*) in FIG. 25. These oligonucleotides displaced the excised native oligonucleotide. Following polynucleotide kinase treatment, the oligonucleotide was ligated into the plasmid. Successful ligation and functional characterization of the resulting reporter are illustrated in FIG. 26.

Example 12: Verification of a Site-Specific DNA Damage Containing Reporter

Verification of a site specific DNA damage containing reporter was verified by gel electrophoresis. These results can be found in FIG. 26: Uncut reporter plasmid in lane #1 ran at approximately 2 kb. The nicked plasmid in lane #2 ran at close to 4 kb. Ligase failed to yield a closed circular product between the displacing thymine dimer containing oligo (T<>T) and the nicked reporter in the absence of PNK (lane 3). However, in the presence of PNK, the T<>T oligo is successfully ligated into the reporter plasmid (lane #4, 2 kb band). This product can be cut with T4 PDG, a bifunctional glycosylase that creates a single strand break only where pyrimidine dimers are present in DNA. The exclusively nicked DNA in lane 5 confirms that the closed circular product in lane #4 contains the pyrimidine dimer. Randomly induced UV damage also makes the reporter plasmid a substrate for T4 PDG (Lane #6). On the right, we see that Reporter expression is partially blocked in the reporter construct corresponding to lane #4 in the gel. As expected, the XPA cell line, which is deficient in the Nucleotide Excision Repair pathway that acts on thymine dimers, shows more severely reduced fluorescent reporter expression of the site-specific reporter, relative to the undamaged control. We are preparing to make more substrates like this one, with different types of damage, for use in a high throughput sequencing based HCR, as described above in FIGS. 20, 21 and 23.

Figure 27:
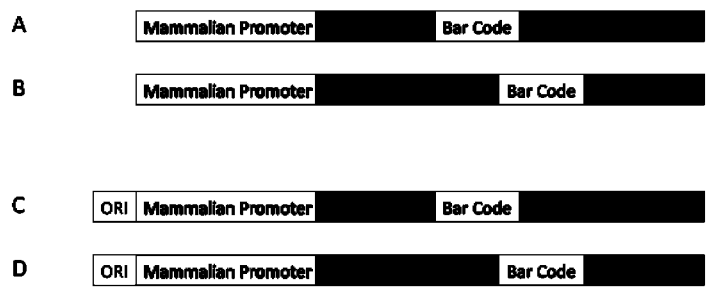
FIG. 27 is an illustration showing the finding that four basic reporter constructions comprise the library of reporters to be used with next generation sequencing. A-D represent DNA sequences in the context of a transiently transfected plasmid reporter.

Example 13: Four Basic Reporter Constructions Comprise the Library of Reporters to be Used with Next Generation Sequencing FIG. 27 shows four basic reporter constructions that comprise the library of reporters to be used with next generation sequencing. All reporters have a mammalian promoter, which could be the CMV promoter where very high expression is desired, or an inducible/repressible promoter that permits adjustable expression. The latter has utility in studying transcription coupled repair of DNA damage. Each reporter has a unique bar code. The bar code identifies the lesion that is present in the reporter, and can also be used to multiplex samples (with a different bar code associated with each subject or cell line being studied). Sequence changes in transcripts in the sequence space indicated as "lesion" report on transcriptional mutagenesis. In Example 1, the entire fluorescent reporter sequence was used as the bar code, and as the sequence space that reported on transcriptional mutagenesis. All reporters contain a lesion, and have in common 5' and 3' PCR amplification sequences (5'Amp and 3'Amp) that are located in such a manner that the resulting amplicon spans both the lesion and the bar code. The lesion may be located 3' (A) or 5' (B) to the bar code. A mammalian origin of replication may be absent (A and B), or present. The latter is useful in studying the repair of lesions in the context of DNA replication.

Figure 28:
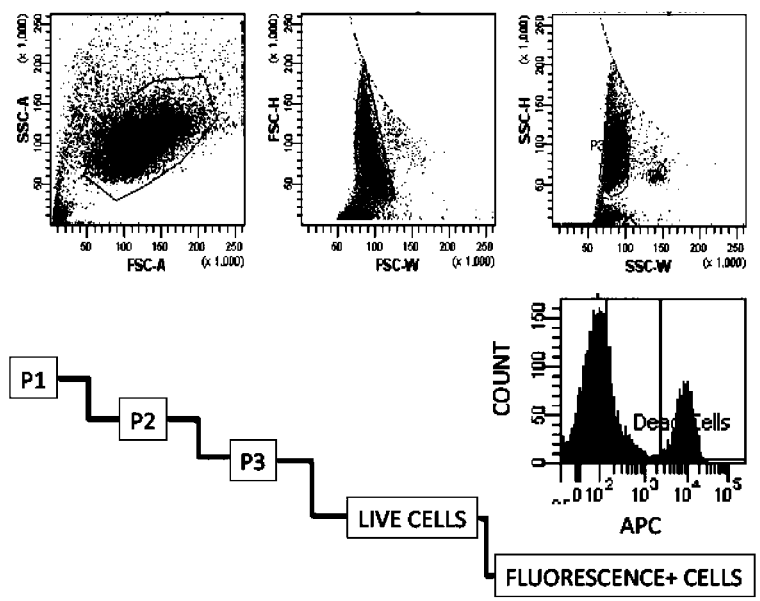
FIG. 28 shows a primary gating scheme for TK6 lymphoblastoid cells.

Example 14: Gating Procedure for 6-Color Flow Cytometric Detection of 5 Fluorescent Reporters and One Dead Cell Stain FIG. 28 shows a primary gating scheme for TK6 lymphoblastoid cells. The population hierarchy is shown at the bottom of the figure; A main population P1 was established in the SSC-A vs FSC-A plot. Nested within P1, a secondary population P2 was established using the FSC-H vs. FSC-W plot. Further nested within this population, a tertiary population P3 was established. P2 and P3 were used to exclude doublets and higher order aggregates of cells. Finally, the cells in P3 were separated into two populations, live and dead. Cells were incubated at room temperature for 5 minutes in 100 nM TOPRO-3. The stain was left in the cell suspension, and fluorescence was measured in the APC channel (Excitation with a 634 nm laser). Dead cells in the higher staining population were unable to exclude the dye. Live cells were analyzed further for their fluorescence in the other five colors, namely the fluorescent reporter proteins tagBFP, AmCyan, EGFP, mOrange, and mPlum. The procedure for identifying cells positive for each of these reporters is given below.

Figure 29:
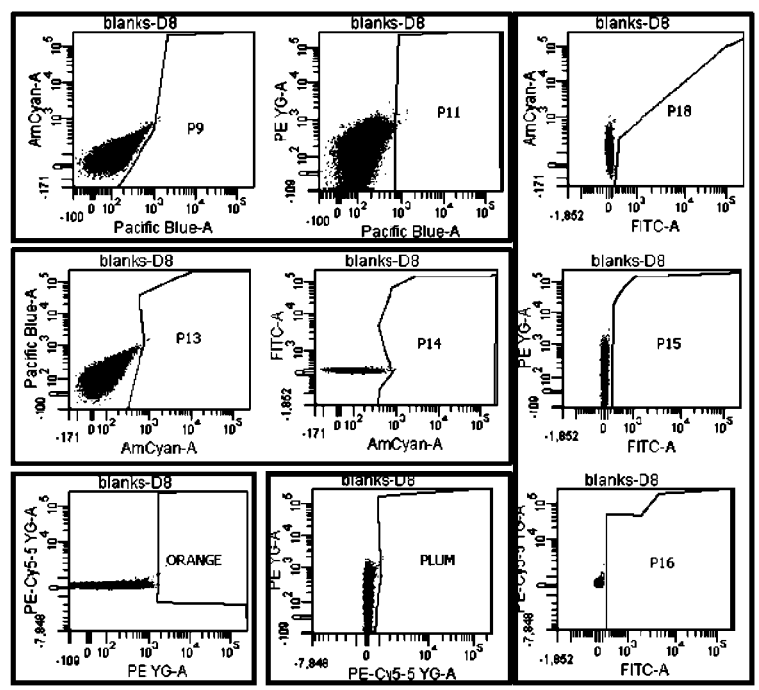
FIG. 29 shows a gating scheme for negative controls (mock transfected cells).

FIG. 29 shows Negative controls (mock transfected cells). Cells that have been subjected to transfection conditions in the absence of exogenous plasmid DNA are used to establish regions in each channel corresponding to cells that are not expressing fluorescent reporters. Gates are drawn so as to exclude at least 99.9% of the untransfected cells. Gates needed to distinguish positive from negative cells are circumscribed in FIG. 29 with boxes in colors that correspond to the color of the respective reporter indicated on the X-axis of each plot (BFP, blue, Pacific blue detector; AmCyan, cyan, AmCyan Detector; mOrange, orange, PE detector; mPlum, red, PE-Cy5-5 detector; GFP, green, FITC detector).

Figure 30:
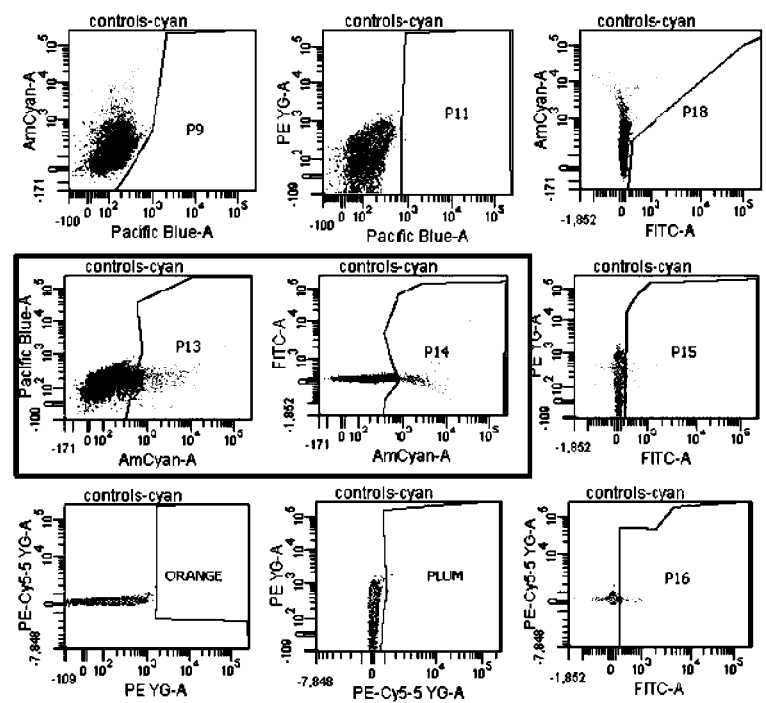
FIG. 30 provides an example of a single color control gating, where single color refers to cells transfected with a single fluorescent reporter plasmid.

FIG. 30 shows an example of a single color control. Cells appearing simultaneously in both P13 and P14 are defined to be positive for AmCyan. (An example showing why multiple gates are needed is seen below for GFP). Compensation has been adjusted so that, as nearly as possible, cells positive for AmCyan have the same MFI for each of the other detectors as do cells negative for AmCyan. Similarly, cells simultaneously in P9 and P11 are positive for BFP, and Cells appearing in all three gates, P15, P16, and P18 are positive for GFP. 3 gates are needed to define GFP positive cells because of spectral overlap. This is seen in gates P15 and P16, where cells positive for AmCyan also appear to be positive for GFP, despite spectral compensation. However, gate P18 excludes the cells responsible for the false positives in P15 and P16. Using this system of gates, when GFP is excluded from a transfection, 99.9% or more of cells are detected as negative for GFP, regardless of the presence of other reporters (not shown). For the reporters described here, 9 gates were the minimum required to establish regions such that at least 99.9% of cells not transfected with a given reporter are excluded from the positive population. A general approach is described below.

Compensation is applied to data as follows: Cells are transfected with each reporter of interest one at a time (single color controls). Two populations, positive and negative, are established for a given reporter. Compensation in that detector is adjusted until the mean fluorescence intensity (MFI) measured for each other detector is the same for both positive and negative populations, as defined above. In other words, the MFI in one detector is independent of whether the cells are positive or negative for a second detector.

Figure 31:
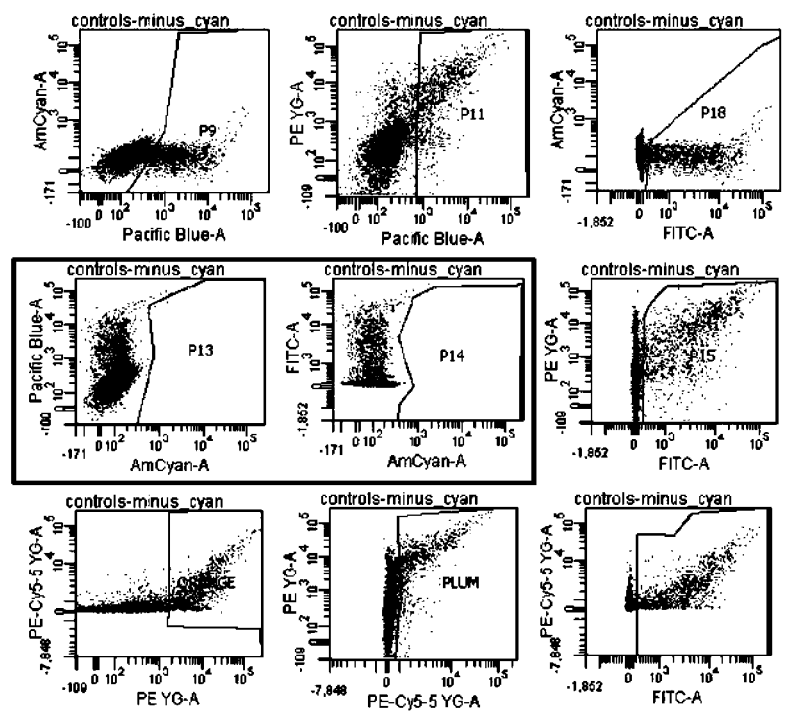
FIG. 31 shows Cyan Excluded from transfection. The number of cells appearing in both P13 and P14 is zero, consistent with the absence of the AmCyan reporter in the transfection. All other reporters are detected.

The general approach to establishing a gating scheme for any set of fluorescent reporters is as follows: Set compensation using single color controls, as described above. To determine the positive region for a given reporter, a plot the reporter of interest (on the horizontal axis), against each of the other reporters (on the vertical axis) that were found to have significant spectral overlap with the reporter of interest. For each single color control, examine the plot of that color against the reporter of interest. Establish a region that excludes false positives in the reporter channel of interest due to reporter expression in the single color control channel. Establish a gate that takes the union "AND" of these gates as the region corresponding to cells positive for the reporter of interest. Repeat this process for each reporter. Then examine the "minus-one" controls, where one reporter is excluded at a time (and all others are present, for example minus Cyan in FIG. 31). Examine the minus-one transfection for the detector of interest, and again adjust all gates to ensure that at least 99.9% of cells are excluded from the positive "union" gate for the detector of interest. Repeat this process for the remaining reporters.

Example 15: Cisplatin and Reporter Expression

Figure 32:
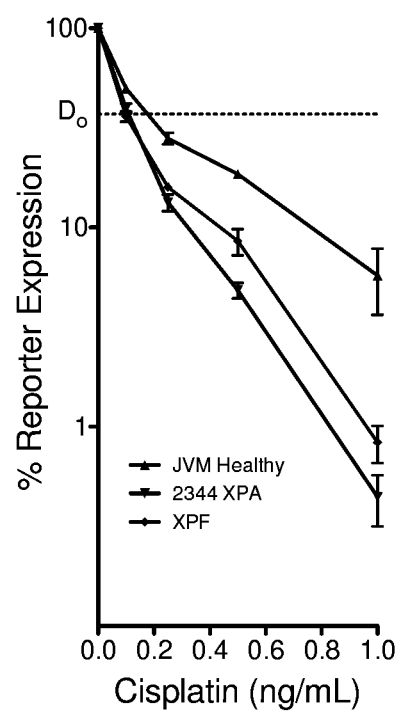
FIG. 32 is a graph showing the dose-dependent inactivation of fluorescent DNA repair reporter plasmids treated with Cisplatin.

The data provided in FIG. 32 show that treatment of DNA repair reporter vectors with Cisplatin suppresses florescent reporter expression in a dose dependent manner. As expected the effect was even more pronounced in cells deficient in nucleotide excision repair and DNA crosslink repair (XPA and XPF).

Example 16: Synthesis of a Substrate with a Site-Specific $O^6$-Methylguanine ($O^6$-MeG)

Figure 33:
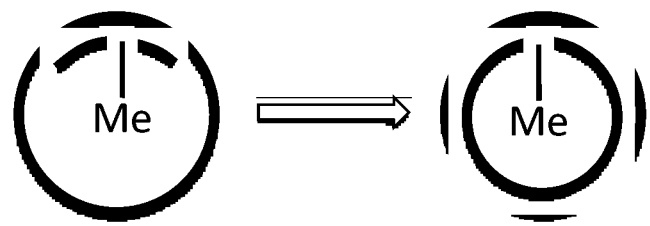
FIG. 33 is an illustration showing the synthesis of a substrate with a site-specific $O^6$-MeG.

FIG. 33 shows a summary of the method for the synthesis of a site-specific $O^6$-MeG using single stranded closed circular DNA and an oligonucleotide containing an $O^6$-MeG residue at a defined position.
1) Prepare mPlum ssDNA (+) strand as described by digest with a nicking endonuclease specific for the (−) strand followed by digest with ExoIII, which removes the (−) strand.
2) Combine single stranded DNA with 4-fold molar excess of 30 nt oligo containing 06-Methylguanine
3) Treat with polynucleotide kinase, heat to 85° C., slow cool to anneal
4) Add dNTPs, T4 DNA polymerase, T4 DNA ligase
5) Incubate 1 hour at 37° C.
(Baerenfaller et al. (2006) Method Enzymol 18, p 285)

Example 17: HCR Assay Using a Substrate with a Site-Specific $O^6$-MeG

Figure 34:
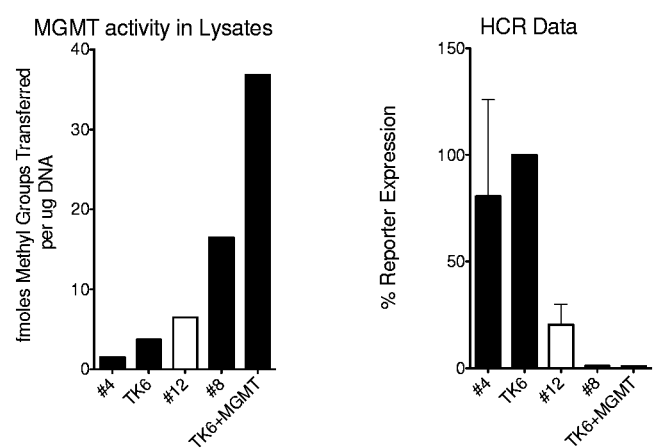
FIG. 34 shows graphs of a DNA repair capacity assay using a fluorescent reporter vector with a site-specific $O^6$-MeG.

FIG. 34 shows an HCR assay using a substrate with a site-specific $O^6$-MeG. The data show an inverse relationship between % reporter expression using the disclosed HCR-assay and MGMT (methyl guanine methyl transferase) activity as measured by an independent method in lysates. As $O^6$-MeG is repaired, transcriptional mutagenesis decreases, resulting in less expression of the wild type mPlum reporter protein.

Figure 35:
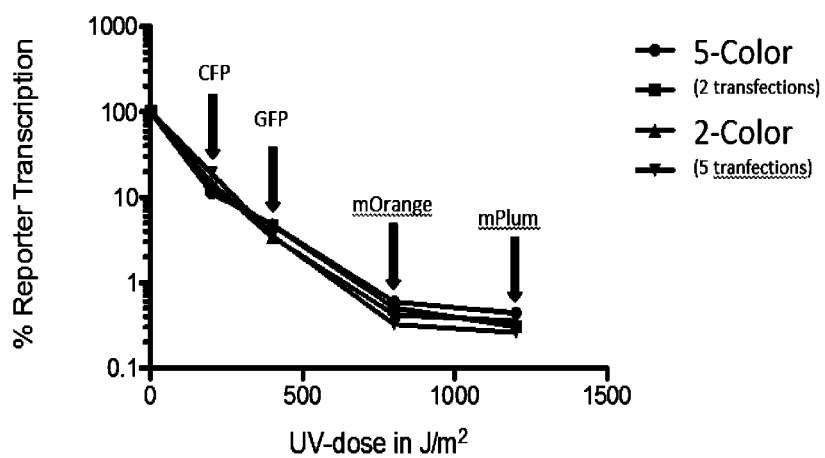
FIG. 35 is a graph comparing 2-color versus 5-color fluorescent reporter HCR of UV-irradiated plasmids. UV HCR: XPA-deficient cell line at 16 hours. The number of colors refers to the number of fluorescent reporters co-transfected into cells. The color of the fluorescent reporter used at each dose in the 5-color experiment is indicated by an arrow. In the 2-color experiment, mCherry was used at all 4 doses in separate transfections.

Example 18: Comparing 2-Color Versus 5-Color Fluorescent Reporter HCR of UV-Irradiated Plasmids FIG. 35 provides a graph comparing 2-color versus 5-color fluorescent reporter HCR of UV-irradiated plasmids. UV HCR: XPA-deficient cell line at 16 hours. In the 2-color experiment, 5 transfections using the plasmids pmax:GFP and pmax:mCherry were necessary:
1. pmax:GFP plus pmax:mCherry at 0 $J/m^2$.
2. pmax:GFP plus pmax:mCherry at 200 $J/m^2$.
3. pmax:GFP plus pmax:mCherry at 400 $J/m^2$.
4. pmax:GFP plus pmax:mCherry at 800 $J/m^2$.
5. pmax:GFP plus pmax:mCherry at 1200 $J/m^2$.

In the 5-color experiment, only two transfections were necessary:
1. pmax:BFP+pmax:AmCyan+pmax:GFP+pmax:mOrange+pmax:mPlum, all at 0 $J/m^2$.
2. pmax:BFP at 0 $J/m^2$+pmax:AmCyan at 200 $J/m^2$+pmax:GFP at 400 $J/m^2$+pmax:mOrange at 800 $J/m^2$+pmax:mPlum at 1200 $J/m^2$.

Example 19: Estimating Recombination Frequency

Figure 36:
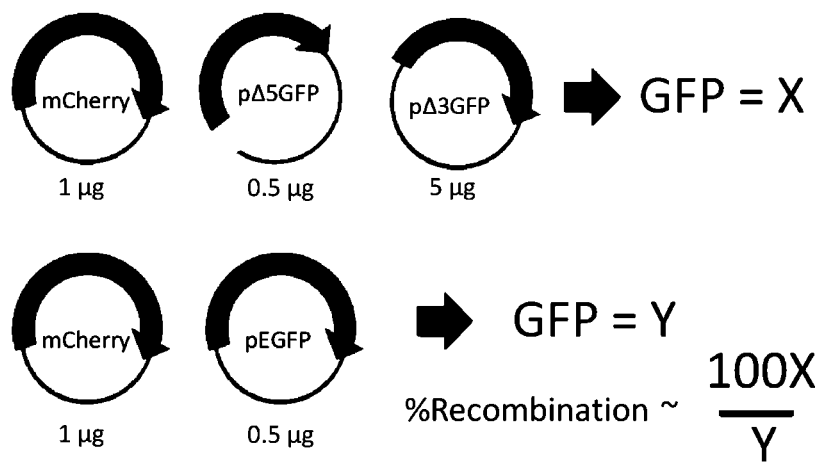
FIG. 36 is an illustration showing the estimation of recombination frequency.

FIG. 36 provides an illustration showing a method of estimation of recombination frequency. In one transfection (top) cells are co-transfected with 1 microgram of pmax:mCherry as to control for transfection efficiency, plus 0.5 micrograms of a 5'-truncated (nonfluorescent) linearized GFP reporter plasmid pD5GFP (see Kiziltepe T. et al, Chemistry & Biology, 2005. 12(3): p. 357-369), plus 5 micrograms of a 3'truncated GFP reporter plasmid. If 100% of the linearized plasmid is repaired by homologous recombination, the expected fluorescence signal is equal to that obtained from a separate co-transfection (bottom) with 0.5 micrograms of full length GFP reporter plasmid plus 1 microgram of pmax:mCherry reporter plasmid.

Example 20: Double Strand Break Induced Recombination

Figure 37:
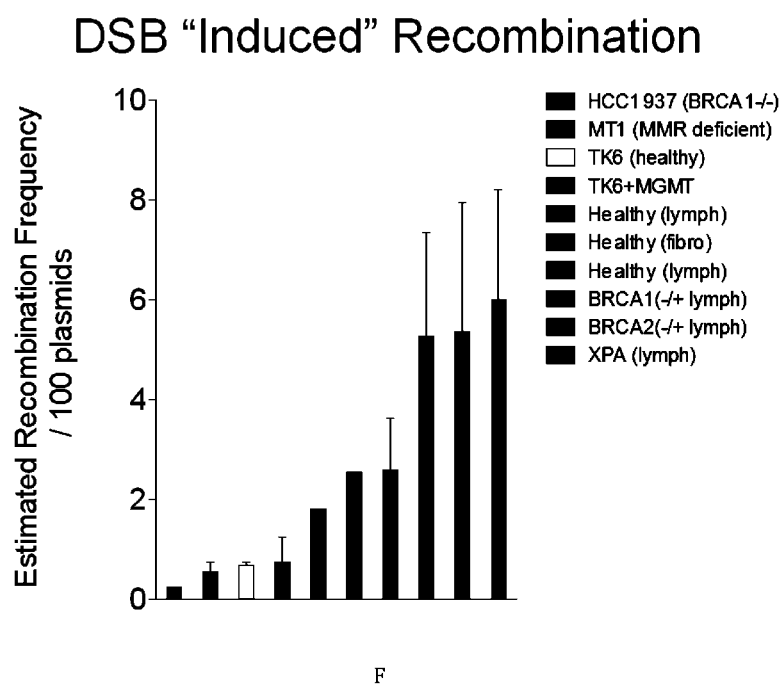
FIG. 37 is a graph showing a 25-fold range of HR repair capacity over several cell lines in DSB (double strand break) "induced" recombination.

FIG. 37 provides a graph showing a 25-fold range of HR repair capacity over several cell lines in DSB "induced" recombination. As expected, a reduced recombination frequency is observed in a cell line deficient for BRCA1.

Example 21: Mismatch Repair Substrate

Figure 38:
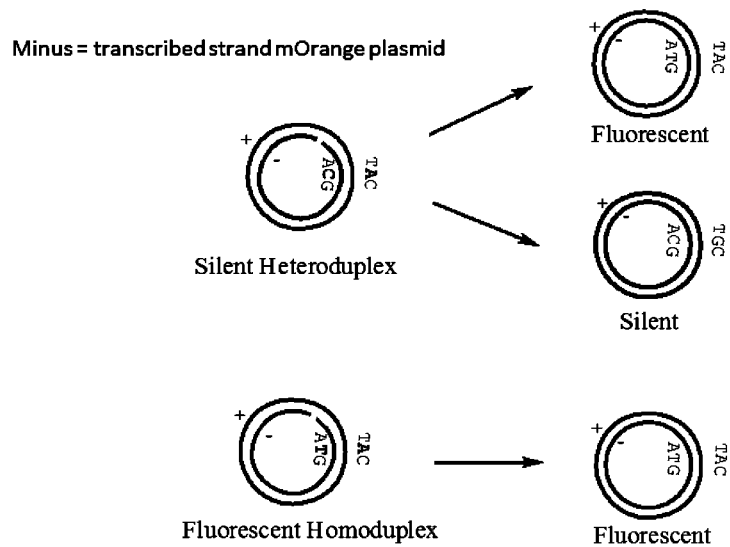
FIG. 38 is an illustration showing the mismatch repair substrate with methods adapted from Zhou, B. S. et al, Anal. Biochem. 388, 167-169, (2009).

FIG. 38 provides an illustration showing a mismatch repair substrate (See also Zhou, B. S. et al, Anal. Biochem. 388, 167-169, (2009)) wherein the sequence in the transcribed strand of the reporter plasmid encodes a non-fluorescent plasmid. Restoration of the wild type sequence in the transcribed strand can result from mismatch repair activity, leading to expression of the wild type (fluorescent) reporter protein mOrange.

Example 22: Multiple Lesions in a Single Plasmid

Figure 39:
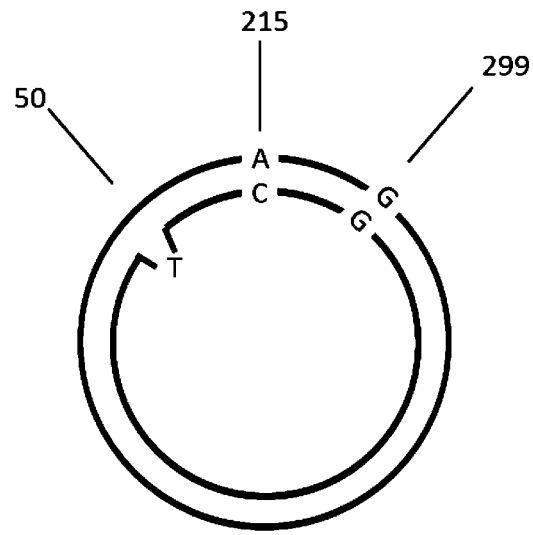
FIG. 39 is an illustration showing multiple lesions in a single plasmid. A single base loop is indicated at position 50, an A:C mismatch is shown at position 215, and a G:G mismatch is shown at position 299. All three lesions are substrates for mismatch repair.

FIG. 39 provides an illustration showing multiple lesions in a single plasmid. A wild type closed circular single stranded DNA comprising the non-transcribed strand of the pmax:mOrange fluorescent reporter plasmid has been annealed to the complementary (transcribed) strand of a plasmid with three mutations, each of which results in a non-fluorescent reporter protein. A single base insertion at position 50 results in a single base loop. Base substitutions at positions 215 and 299 result in A:C and G:G mismatches, respectively. All combinations of the mutations also yield reporter plasmids that express non-fluorescent reporter proteins. Only repair of all three lesions results in fluorescence. This reduces background that may arise from other repair mechanisms (such as BER) that may act locally on some mismatches and loops; the length of mismatch repair tracts is sufficient to repair all three lesions in a single repair event.

Example 23: Mismatch Repair and Multiple Lesions

Figure 40:
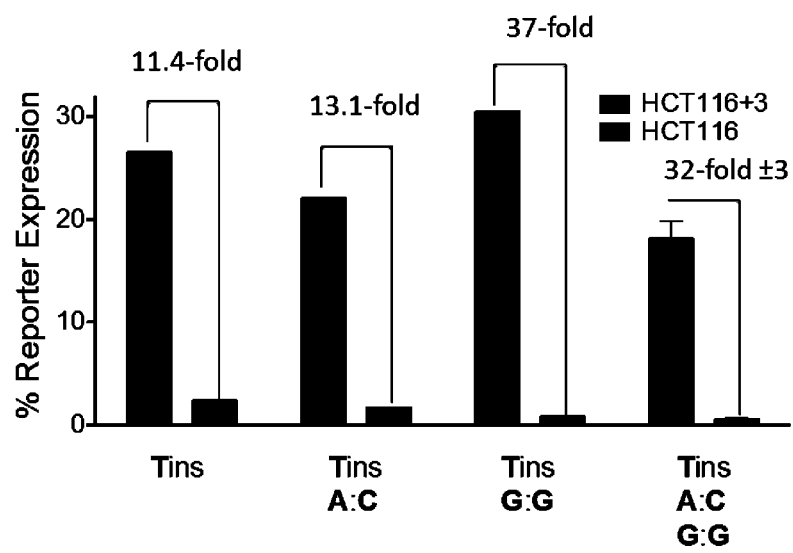
FIG. 40 is a graph showing that the ability to distinguish between the repair capacity of MMR+ and MMR− cells improves with multiple lesions.

FIG. 40 provides a graph showing that the differential between mismatch repair proficient (MMR+) and deficient (MMR−) improves with multiple lesions. HCT116 cells are (MMR−) because they are deficient for the mismatch repair protein MLH1. HCT116+3 cells are complemented with MLH1 expressed from the human chromosome #3, and are therefore MMR+.

Example 24: Alkylation Damage Repair and Transcription Inhibition

Figure 41:
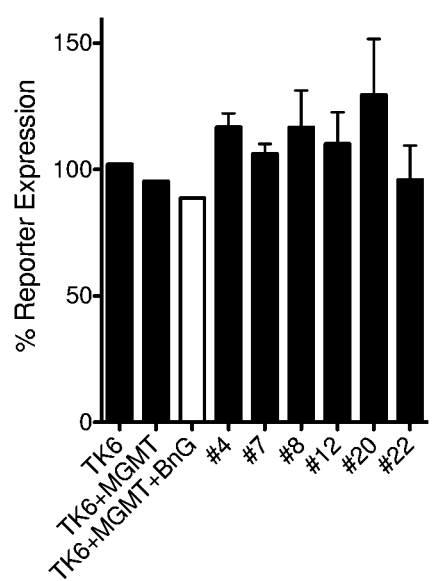
FIG. 41 is a graph showing that the inhibition of transcription is not detected when a reporter plasmid is treated with MNNG, followed by transfection into cells, and a fluorescence assay is performed at 16 hours. In this example a plasmid was treated for 4 hours in 0.8 mM MNNG.

FIG. 41 provides a graph showing that the inhibition of transcription is not detected when a fluorescent reporter plasmid is treated with the alkylating agent MNNG and reporter expression is assayed by flow cytometry 16 hours after transfection. In this example a plasmid was treated for 4 hours in 0.8 mM MNNG (Cell lines #4-22 are Corriell cell lines from apparently healthy individuals). Treatment with MNNG induces several types of alkylation damage in DNA, including $O^6$-MeG. TK6 cells are deficient for MGMT, the enzyme that repairs $O^6$-MeG by direct reversal, and TK6+ MGMT has been complemented with the enzyme to restore repair capacity. $O^6$-benzylguanine (BnG) inactivates MGMT, rendering cells treated with the compound unable to repair $O^6$-MeG (TK6+MGMT+BnG). The lack of significant differences in the extent of reporter expression in these cell lines indicates ordinary host cell reactivation assays are not amenable to measurements of $O^6$-MeG repair capacity.

Example 25: Non Fluorescent mPlum Variant

Figure 42:
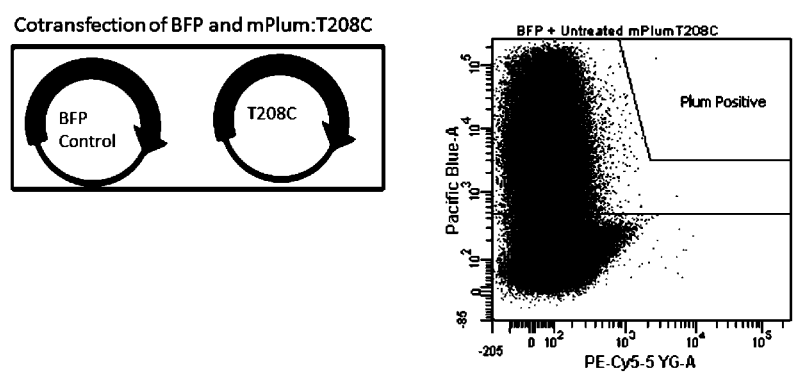
FIG. 42 shows that a point mutation (T208C) results in a non-fluorescent mPlum variant S70P. Of 500,000 cells analyzed—only a single plum positive cell was found.

FIG. 42 shows that a point mutation (T208C) results in a non-fluorescent mPlum variant S70P. Of 500,000 cells analyzed—virtually no plum positive was found.

Example 26: Mutations Induced in mPlum Variant

FIG. 43 is an illustration showing that when $O^6$MeG is present in the transcribed strand, some mRNA will contain U producing wild type mPlum protein. The mutation T208C results in a guanine at the corresponding position in the transcribed strand. Transcripts therefore contain the codon CCC (proline) instead of the wild type UCC (serine). However, since $O^6$MeG is transcribed as "U" instead of "C" with approximately 25% frequency, some transcripts produced from plasmids containing this lesion will have the wild type sequence, and will be translated into fluorescent protein.

Example 27: Assay for $O^6$Methylguanine HCR

Figure 44:
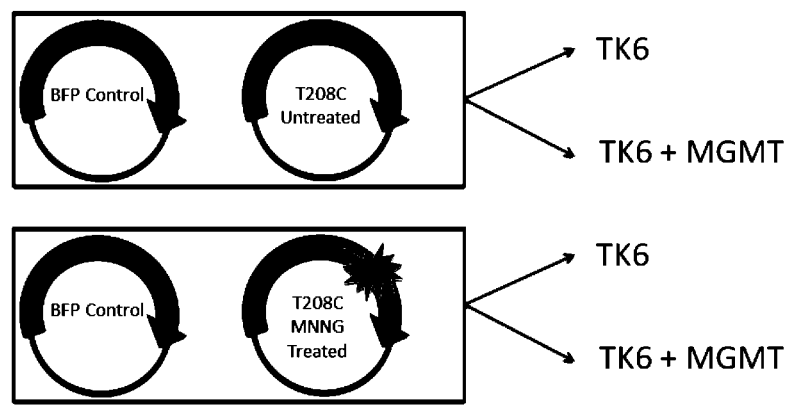
FIG. 44 is an illustration showing an assay for $O^6$Methylguanine HCR.

FIG. 44 is an illustration providing an assay for $O^6$Methylguanine HCR. An increase in fluorescence is expected when the reporter plasmid containing the mPlum: T208C mutation is treated with an agent that induces $O^6$MeG. Cells that are able to repair the lesion will exhibit reduced fluorescence.

Example 28: MNNG Induced Plasmid Induces Plum Positive Variants

Figure 45:
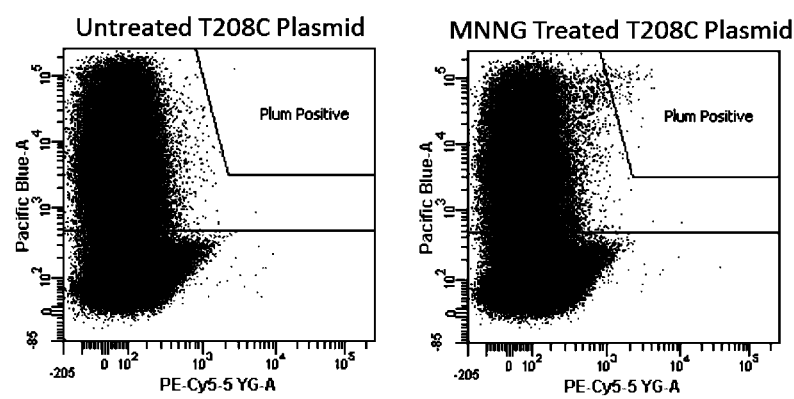
FIG. 45 shows the results for TK6, MGMT-deficient (MGMT=methyl guanine methyl transferase). 500,000 cells were analyzed—a few hundred plum positive TK6 cells are detected following transfection with MNNG treated plasmid, consistent with alkylation induced transcriptional mutagenesis.

FIG. 45 shows the results for TK6, which are MGMT-deficient. 500,000 cells were analyzed at 16 hours post-transfection—only a few hundred plum positive with MNNG treated plasmid because random alkylation produces $O^6$MeG at a low frequency. The method of introducing a site-specific $O^6$MeG (Example 17) is much more efficient and so requires fewer cells.

Example 29: MGMT and Reporter Signal

Figure 46:
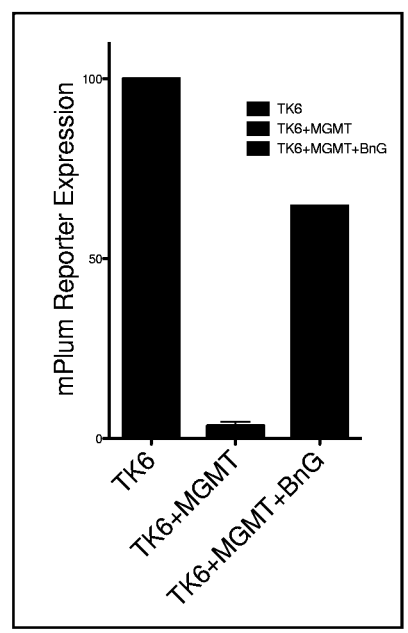
FIG. 46 is a bar graph showing that the lack of signal is MGMT dependent. BnG stands for $O^6$-benzylguanine, which inhibits MGMT.

FIG. 46 is a bar graph showing that the lack of signal is MGMT dependent. Reporter expression has been normalized to that for TK6. As expected, the highest reporter expression is observed in MGMT deficient cells. Cells complemented with MGMT (TK6+MGMT) exhibit at least 25-fold lower reporter expression. As further confirmation that reporter expression is MGMT- and $O^6$MeG-dependent, cells incubated with $O^6$Benzylguanine before and after transfection (TK6+MGMT+BnG) show elevated reporter expression similar to that of the MGMT deficient TK6 cells.

Example 30: Comparison of MGMT Activity

Figure 47:
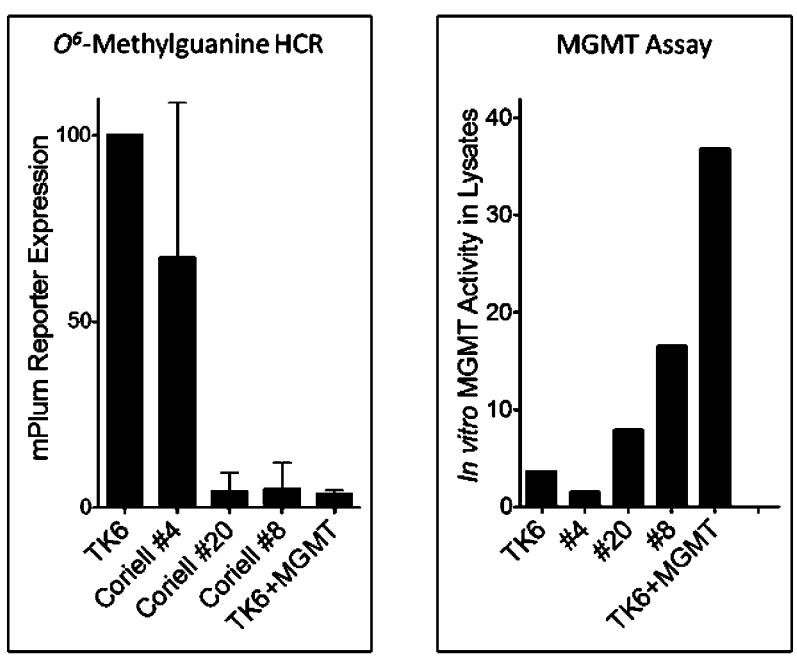
FIG. 47 shows a preliminary comparison with independent characterization of MGMT activity in extracts. (Fry et al Genes. Dev. 2008 (22) p 2621).

FIG. 47 shows a preliminary comparison of reporter expression from mPlum:T208C reporter plasmids randomly alkylated with MNNG with independent characterization of MGMT activity in extracts. (Fry et al Genes. Dev. 2008 (22) p 2621). As expected, and similar to what was observed when cells were assayed using a plasmid with a site-specifically engineered $O^6$MeG lesion (See Example 17), an inverse relationship is observed between the extent of reporter expression and the amount of MGMT activity found in cell lysates.

Example 31: Measurement of NER and HR in Single Assay

Figure 48:
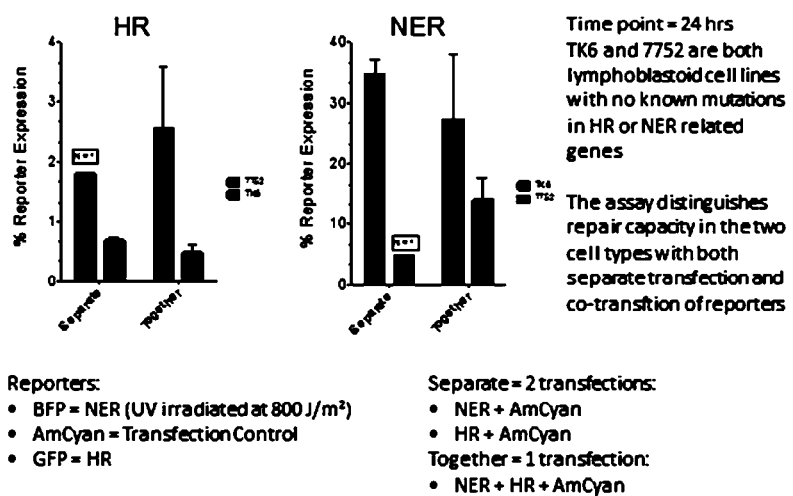
FIG. 48 shows that measurement of NER and HR in a single assay yields the same information as separate measurements. "Separate" refers to an experiment in which plasmid reporters for NER and HR capacity were transfected separately. "Together" refers to an experiment in which the reporters for NER and HR capacity were co-transfected in a single assay.

FIG. 48 shows that measurement of NER and HR in a single assay yields the same information as separate measurements. This experiment demonstrates the ability to measure DNA repair capacity in multiple repair pathways using a single assay and methodology. Multiple fluorescent reporters with different colors corresponding to different repair pathways (for example the mOrange reporter for mismatch repair in Example 23 and the mPlum reporter for direct reversal of alkylation damage in Examples 17 and 30) can be combined in a modular, interchangeable format to assay cells for global DNA repair capacity.

Example 32: HCR and Etheno (ε) Lesions

Figure 49:
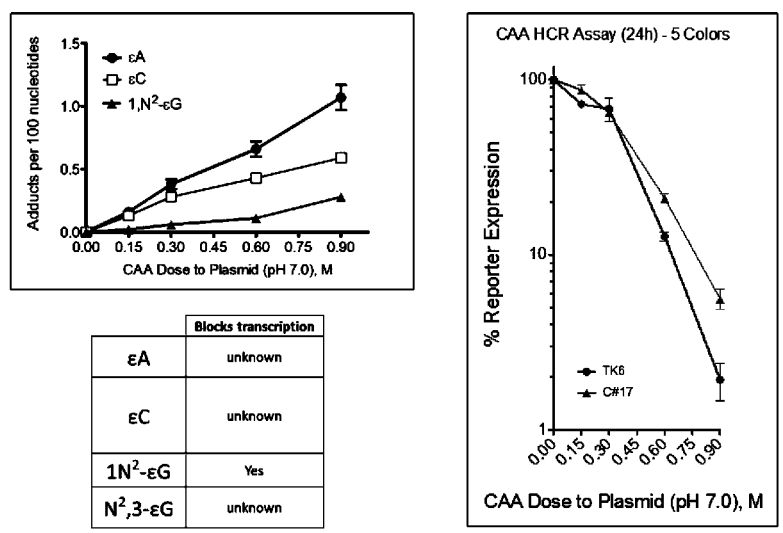
FIG. 49 shows HCR of plasmids containing etheno (ε) lesions. The upper left panel shows mass spectrometric quantitation of etheno adducts in plasmid DNA treated with chloroacetaldehyde (CAA). Dose and cell line dependent inhibition of transcription in plasmids treated with CAA is shown at right.

FIG. 49 shows HCR of plasmids containing etheno (ε) lesions. Mass spectrometric quantitation confirms concentration-dependent induction of etheno adducts in plasmid DNA by chloroacetaldehyde (CAA). A dose-dependent decrease in fluorescent reporter expression is observed, with significant differences between lymphoblastoid cell lines derived from two individuals with no known mutations in the pathways known to repair DNA base etheno adducts, suggesting possible inter-individual variability in repair capacity for DNA lesions induced by CAA.

Example 33: Etheno (ε) Lesions and Base Excision Repair

Figure 50:
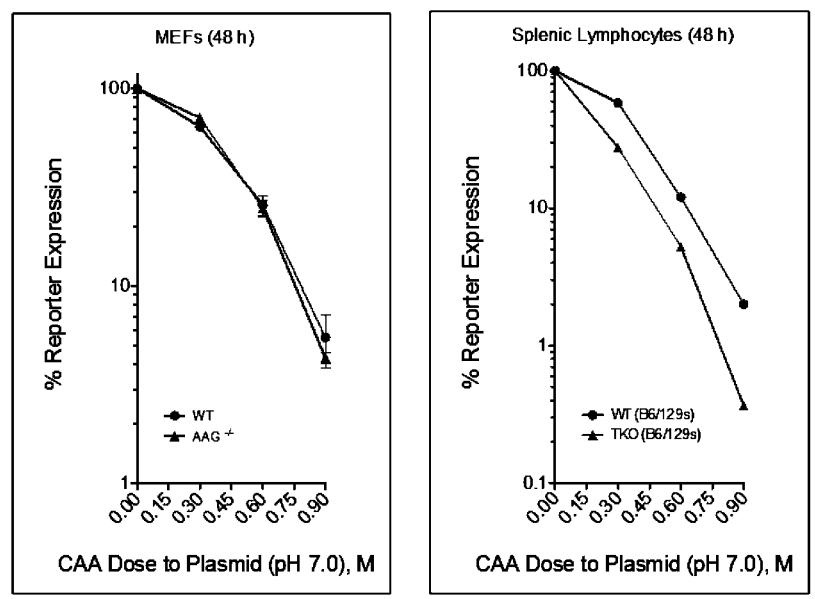
FIG. 50 shows that mouse cells deficient for base excision repair and direct reversal of (ε) lesions (Aag, Alkbh2, Alkbh3 null) exhibit reduced expression of fluorescent reporters that have been damaged with CAA.

FIG. 50 shows that mouse cells deficient in BER and direct reversal for (ε) lesions repair (Aag, Alkbh2, Alkbh3 null) exhibit reduced reporter expression from plasmids damaged with CAA, suggesting that some lesions repaired by these proteins at least partially block transcription.

REFERENCES

1. Ellis, N.C., *Obtaining and Using Genetic Information.* Inherited Cancer Syndromes: Current Clinical Management, ed. N. C. Ellis 2003, New York: Springer.
2. Chin, L. and J. W. Gray, *Translating insights from the cancer genome into clinical practice.* Nature, 2008. 452 (7187): p. 553-563.
3. van't Veer, L. J. and R. Bernards, *Enabling personalized cancer medicine through analysis of gene-expression patterns.* Nature, 2008. 452(7187): p. 564-570.
4. Hanash, S. M., S. J. Pitteri, and V. M. Faca, *Mining the plasma proteome for cancer biomarkers.* Nature, 2008. 452(7187): p. 571-579.
5. Li, C., L.-E. Wang, and Q. Wei, *DNA repair phenotype and cancer susceptibility—A mini review.* International Journal of Cancer, 2009. 124(5): p. 999-1007.
6. Kraemer, K. H., M. M. Lee, and J. Scotto, *DNA-REPAIR PROTECTS AGAINST CUTANEOUS AND INTERNAL NEOPLASIA—EVIDENCE FROM XERODERMA PIGMENTOSUM.* Carcinogenesis, 1984. 5(4): p. 511-514.
7. Ramos, J. M., et al., *DNA repair and breast carcinoma susceptibility in women.* Cancer, 2004. 100(7): p. 1352-1357.
8. Athas, W. F., et al., *Development and field-test validation of an assay for DNA-repair in circulating human lymphocytes.* Cancer Research, 1991. 51(21): p. 5786-5793.
9. Decordier, I., K. V. Loock, and M. Kirsch-Volders, *Phenotyping for DNA repair capacity.* Mutation Research-Reviews in Mutation Research, 2010. 705(2): p. 107-129.
10. Ralhan, R., et al., *Links between DNA double strand break repair and breast cancer: Accumulating evidence from both familial and nonfamilial cases.* Cancer Letters, 2007. 248(1): p. 1-17.
11. Wilson, D. M., et al., *Variation in base excision repair capacity.* Mutation Research-Fundamental and Molecular Mechanisms of Mutagenesis, 2011. 711(1-2): p. 100-112.
12. Evans, R. G. and A. Norman, *Radiation stimulated incorporation of thymidine into DNA of human lymphocytes.* Nature, 1968. 217(5127): p. 455-&.
13. Perry, P. and H. J. Evans, *CYTOLOGICAL DETECTION OF MUTAGEN CARCINOGEN EXPOSURE BY SISTER CHROMATID EXCHANGE.* Nature, 1975. 258(5531): p. 121-125.
14. Parshad, R., K. K. Sanford, and G. M. Jones, *Chromatid damage after G2 phase X-irradiation of cells from cancer-prone individuals implicates deficiency in DNA repair* Proceedings of the National Academy of Sciences of the United States of America-Biological Sciences, 1983. 80(18): p. 5612-5616.
15. Wood, D. K., et al., *Single cell trapping and DNA damage analysis using microwell arrays.* Proceedings of the National Academy of Sciences of the United States of America, 2010. 107(22): p. 10008-10013.
16. Qiao, Y. W., et al., *Rapid assessment of repair of ultraviolet DNA damage with a modified host-cell reactivation assay using a luciferase reporter gene and correlation with polymorphisms of DNA repair genes in normal human lymphocytes.* Mutation Research-Fundamental and Molecular Mechanisms of Mutagenesis, 2002. 509(1-2): p. 165-174.
17. Mendez, P., et al., *A modified host-cell reactivation assay to quantify DNA repair capacity in cryopreserved peripheral lymphocytes.* DNA Repair, 2011. 10(6): p. 603-610.
18. Trapnell, C., et al., *Differential gene and transcript expression analysis of RNA-seq experiments with TopHat and Cufflinks.* Nature Protocols, 2012. 7(3): p. 562-578.
19. Koboldt, D. C., et al., *VarScan 2: Somatic mutation and copy number alteration discovery in cancer by exome sequencing.* Genome Research, 2012. 22(3): p. 568-576.
20. Jagger, J., *Ultraviolet inactivation of biological systems,* in Photochemistry and Photobiology of Nucleic Acids, S. Y. Wang, Editor 1976, Academic Press: New York. p. 147-186.
21. Kitsera, N., et al., *8-Oxo-7,8-dihydroguanine in DNA does not constitute a barrier to transcription, but is converted into transcription-blocking damage by OGG1.* Nucleic Acids Research, 2011. 39(14): p. 5926-5934.
22. Satokata, I., et al., *Identification of splicing mutations of the last nucleotides of exons, a nonsense mutation, and a missense mutation of the XPAC gene as causes of group A xeroderma pigmentosum.* Mutation Research, 1992. 273(2): p. 203-212.
23. Choy, E., et al., *Genetic Analysis of Human Traits In Vitro: Drug Response and Gene Expression in Lymphoblastoid Cell Lines.* Plos Genetics, 2008. 4(11).
24. Davis, A. R. and I. S. Kohane, *Expression differences by continent of origin point to the immortalization process.* Human Molecular Genetics, 2009. 18(20): p. 3864-3875.
25. Stark, A. L., et al., *Heritable and non-genetic factors as variables of pharmacologic phenotypes in lymphoblastoid cell lines.* Pharmacogenomics Journal, 2010. 10(6): p. 505-512.
26. Viswanathan, A., H. J. You, and P. W. Doetsch, *Phenotypic change caused by transcriptional bypass of uracil in nondividing cells.* Science, 1999. 284(5411): p. 159-162.
27. Bregeon, D. and P. W. Doetsch, *Transcriptional mutagenesis: causes and involvement in tumour development.* Nature Reviews Cancer, 2011. 11(3): p. 218-U88.
28. Marietta, C. and P. J. Brooks, *Transcriptional bypass of bulky DNA lesions causes new mutant RNA transcripts in human cells.* Embo Reports, 2007. 8(4): p. 388-393.
29. Walmacq, C., et al., *Mechanism of Translesion Transcription by RNA Polymerase II and Its Role in Cellular Resistance to DNA Damage.* Molecular Cell, 2012. 46(1): p. 18-29.
30. Baerenfaller et al. (2006) Method Enzymol 18, p 285

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A method of determining DNA repair capacity in multiple pathways simultaneously in a cell, the method comprising:
   introducing multiple DNA repair reporter vectors into a cell, wherein the cell has been isolated from a subject, wherein each of the multiple DNA repair reporter vectors comprises a distinct DNA lesion for each pathway and a reporter sequence encoding a distinct fluorescent reporter protein, exposing the cell to conditions to allow transcription of reporter mRNA and translation of the encoded distinct fluorescent reporter protein to take place within the cell and processing the cell to detect a change in a fluorescence signal for each vector and determining the capacity of the cell to process the multiple DNA repair reporter vectors thereby determining the DNA repair capacity in the multiple pathways simultaneously in the cell based on the presence or absence of the fluorescent signal for each vector.

2. The method of claim 1, wherein the method involves determining DNA repair capacity of a subject.

3. The method of claim 2, wherein the cells obtained from the subject are blood cells.

4. The method of claim 1, wherein the cell is further processed to detect a change in the transcribed sequence of the multiple DNA repair reporter vectors that causes a change in fluorescence signal upon DNA lesion processing.

5. The method of claim 1, wherein the cell is further processed to detect a change in the amount of transcribed sequence of the multiple DNA repair reporter vectors that causes a change in fluorescence signal upon DNA lesion processing.

6. The method of claim 1, wherein DNA repair is nucleotide excision repair, homologous recombination, non-homologous end joining, microhomology mediated end joining, direct reversal, base excision repair, mismatch repair or interstrand crosslink repair.

7. The method of claim 1, wherein the distinct fluorescent reporter protein is selected from the following fluorescent proteins: green fluorescent protein (GFP), *Discosoma* sp. Red fluorescent protein (DsRed), enhanced green fluorescent protein (EGFP), enhanced yellow fluorescent protein (EYFP), enhanced cyan fluorescent protein (ECFP), and enhanced blue fluorescent protein (EBFP).

8. The method of claim 1, wherein the fluorescent signal is detected using flow cytometry.

9. A method of determining the propensity of a subject to respond to a cancer treatment regimen, the method comprising:
   introducing multiple DNA repair reporter vectors into cells obtained from a subject, wherein each of the multiple DNA repair reporter vectors comprises a distinct DNA lesion for each of multiple pathways and a sequence encoding a reporter protein, exposing the cell to conditions to allow transcription of the reporter mRNA and translation of reporter protein to take place within the cell,
   wherein the multiple DNA repair reporter vectors comprise one or more lesions of multiple pathways that are representative of a cancer treatment regimen, and
   processing the cell to detect a change in expression of the reporter protein and determining the capacity of the cells to process the multiple DNA repair reporter vectors simultaneously thereby determining the propensity of the subject to respond to the cancer treatment regimen based on the presence or absence of the reporter protein.

10. The method of claim 9, wherein the cells obtained from the subject are cancer cells.

11. The method of claim 10, further comprising comparing the capacity of the cancer cells to process the multiple DNA repair reporter vectors to the capacity of non-cancer cells to process the multiple DNA repair reporter vectors.

12. The method of claim 9, wherein the lesions that are representative of a cancer treatment regimen comprise DNA-crosslinks.

13. The method of claim 9, wherein the lesions that are representative of a cancer treatment regimen comprise DNA lesions that block transcription.

14. The method of claim 9, wherein the lesions that are representative of a cancer treatment regimen comprise DNA lesions that induce transcription errors.

15. The method of claim 9, wherein the lesions that are representative of a cancer treatment regimen comprise DNA alkylation damage.

16. The method of claim 15, wherein the DNA alkylation damage comprises $O^6$-methyl-guanine.

17. The method of claim 15, wherein the DNA alkylation damage comprises $N^7$-methylguanine.

18. The method of claim 9, wherein the reporter protein is a distinct fluorescent protein and the cell is processed to detect a change in a fluorescence signal.

19. The method of claim 9, wherein the sequence encoding the reporter protein is selected from the group consisting of genes encoding proteins which increase or decrease resistance or sensitivity to antibiotics, genes which encode enzymes whose activities are detectable, and genes which detectably affect the phenotype of transformed or transfected cells.

20. The method of claim 19, wherein the genes which encode enzymes whose activities are detectable are selected from β galactosidase, chloramphenicol acetyltransferase, or alkaline phosphatase.

21. A method of determining DNA repair capacity in multiple pathways simultaneously in a cell, the method comprising:
   introducing multiple DNA repair reporter vectors into a cell, wherein the cell has been isolated from a subject, wherein each of the multiple DNA repair reporter vectors comprises a distinct DNA lesion for each pathway and a unique nucleic acid sequence, exposing the cell to conditions to allow transcription of the unique nucleic acid sequence to produce a unique mRNA sequence for each of the multiple DNA repair reporter vectors and
   processing the cell to detect a presence or absence of the unique mRNAs and determining the capacity of the cell to process the multiple DNA repair reporter vectors thereby determining DNA repair capacity in the multiple pathways simultaneously in the cell based on the abundance of the unique mRNAs.

22. The method of claim 21, wherein the multiple DNA repair reporter vectors comprises at least four DNA repair reporter vectors.

23. The method of claim 21, wherein each DNA repair reporter vector of the multiple DNA repair reporter vectors comprises a unique DNA lesion.

24. The method of claim 21, wherein each DNA repair reporter vector of the multiple DNA repair reporter vectors comprises a specific number of DNA lesions.

25. The method of claim 21, wherein each DNA repair reporter vector of the multiple DNA repair reporter vectors comprises a number of DNA lesions corresponding to a specific dose of damaging agent.

26. The method of claim 21, wherein the multiple DNA repair reporter vectors comprise lesions susceptible to processing by nucleotide excision repair, homologous recombination, non-homologous end joining, microhomology mediated end joining, direct reversal, base excision repair, mismatch repair or interstrand crosslink repair.

27. The method of claim 21, wherein processing of DNA damage is detected by a change in the amount of transcribed sequence of the unique mRNAs.

28. The method of claim 21, wherein processing of DNA damage is detected by a change in the transcribed sequence of the unique mRNAs.

29. The method of claim 21, wherein the DNA lesions comprise DNA lesions that are bypassed by RNA polymerase.

30. The method of claim 21, wherein the change in the transcribed sequence or the change in the amount of transcribed sequence is detected using DNA sequencing.

* * * * *